United States Patent
Vadakekuttu et al.

(10) Patent No.: US 10,492,489 B2
(45) Date of Patent: Dec. 3, 2019

(54) WATER DISINTEGRABLE GRANULAR AGRICULTURAL COMPOSITIONS

(71) Applicants: Thankapan Vadakekuttu, Maharashtra (IN); Arun Vitthal Sawant, Maharashtra (IN)

(72) Inventors: Thankapan Vadakekuttu, Maharashtra (IN); Arun Vitthal Sawant, Maharashtra (IN)

(73) Assignee: Arun Vitthal Sawant, Mumbai (IN)

( * ) Notice: Subject to any disclaimer, the term of this patent is extended or adjusted under 35 U.S.C. 154(b) by 0 days.

(21) Appl. No.: 15/976,304

(22) Filed: May 10, 2018

(65) Prior Publication Data
US 2018/0325105 A1   Nov. 15, 2018

(30) Foreign Application Priority Data

May 10, 2017 (IN) .............................. 201721016449
Jun. 21, 2017 (IN) .............................. 201721021720
(Continued)

(51) Int. Cl.
*A01N 25/12* (2006.01)
*C05D 9/00* (2006.01)
(Continued)

(52) U.S. Cl.
CPC ............ *A01N 25/12* (2013.01); *A01N 25/14* (2013.01); *A01N 59/02* (2013.01); *A01N 59/16* (2013.01);
(Continued)

(58) Field of Classification Search
CPC ........ A01N 25/12; A01N 65/03; A01N 25/14; A01N 63/00; C05G 3/0058; C05G 3/02; C05D 9/00
See application file for complete search history.

(56) References Cited

U.S. PATENT DOCUMENTS

| | | | | |
|---|---|---|---|---|
| 7,638,506 B2 * | 12/2009 | Ozaki | ................... | A01N 25/12 424/405 |
| 7,829,499 B2 * | 11/2010 | Yamashita | ............. | A01N 25/12 424/489 |
| 8,273,685 B2 * | 9/2012 | Dairiki | ................... | A01N 25/04 504/124 |

FOREIGN PATENT DOCUMENTS

| | | |
|---|---|---|
| WO | 2008084495 A2 | 7/2008 |
| WO | 2009125435 A2 | 10/2009 |
| WO | 2012131702 A1 | 10/2012 |

OTHER PUBLICATIONS

International Preliminary Report on Patentability issued in corresponding PCT Application No. PCT/IB2018/053251 dated Jul. 4, 2019.

* cited by examiner

*Primary Examiner* — Carlos A Azpuru

(57) ABSTRACT

An agricultural water disintegrable granular composition is disclosed. The granules include at least one water insoluble crop nutrient or algae or pesticidal active ingredient, and one or more agrochemically acceptable excipient, whereby the granules have a bulk density of less than 1.5 gm/ml and hardness of at least 1 Newton. A process of preparing the water disintegrable granular composition including one or more water insoluble crop nutrients or algae or the pesticidal active ingredients is described. A method of crop protection, fortification of the plants or the soil or the plant propagation material or locus thereof with the water disintegrable granular composition comprising water insoluble crop nutrients or algae or the pesticidal active ingredients is described.

25 Claims, 9 Drawing Sheets

(30) Foreign Application Priority Data

Figure 1:

Jul. 11, 2017 (IN) .............................. 201721024425
Sep. 18, 2017 (WO) ................. PCT/IN2017/050408

(51) Int. Cl.
| | |
|---|---|
| *C05G 3/02* | (2006.01) |
| *C05G 3/00* | (2006.01) |
| *A01N 25/14* | (2006.01) |
| *A01N 59/02* | (2006.01) |
| *A01N 59/16* | (2006.01) |
| *A01N 63/00* | (2006.01) |
| *A01N 65/03* | (2009.01) |

(52) U.S. Cl.
CPC .............. *A01N 63/00* (2013.01); *A01N 65/03* (2013.01); *C05D 9/00* (2013.01); *C05G 3/0058* (2013.01); *C05G 3/02* (2013.01)

WATER DISINTEGRABLE GRANULAR AGRICULTURAL COMPOSITIONS

1. CROSS REFERENCE TO THE RELATED APPLICATION(S)

This application claims priority from India Patent Application Nos. 201721016449 filed May 10, 2017; 201721021720 filed Jun. 21, 2017, and 201721024425 filed Jul. 11, 2017, the contents of which are incorporated herein by reference in their entirety.

2. FIELD OF THE INVENTION

The invention relates to an agricultural granular composition. More particularly, the invention relates to a water disintegrable granular composition, which includes at least one agrochemical and one or more agrochemically acceptable excipient. The agrochemical is selected from a crop nutrient or algae or pesticidal active ingredient. The water disintegrable granular composition particularly has a particle size of 0.1 microns to 50 microns, a bulk density of less than 1.5 gm/ml and hardness of at least 1 Newton. Furthermore, the invention relates to a process of preparing the water disintegrable granular composition including one or more water insoluble nutrients or algae or the pesticidal active ingredients. The invention further relates to a method of treating the plants or the soil with the water disintegrable granular composition.

3. DESCRIPTION OF THE RELATED ART

Crop nutrients or fertilizers and pesticides have been applied to the soil for several years. They have been available in well known granular forms, such as prills, water dispersible granules, or wettable powders, pastilles containing bentonite.

A large problem with several crop nutrients or fertilizers, which when applied, rapidly leach through soil, due to either their rapid mobility in the soil or their physical form and characteristics. Leached nutrients may contribute to groundwater contamination in regions with intensive agriculture. In humid climates, some nutrient leaching occurs even under natural vegetation, but agricultural activities can greatly increase leaching losses.

It is estimated in one study of sandy soils that leaching losses of sulphur amounted to 35 kg/ha to 83 kg/ha depending on the various types of sulphur used during application. It is also known that a shortage of sulphur in the soil lowers the utilization of the available soil nitrogen, thereby increasing nitrate leaching (Likkineni and Abrol, 1994).

It is therefore important to provide these nutrients to the plant at the right stage for uptake and more so to make the nutrients available to the crops or the plant throughout the entire crop life cycle while also preventing or reducing leaching of the nutrients after application. One of the greatest challenges in the application of known compositions is providing adequate release of the actives or nutrients, and also ensuring that the active is available for plant uptake over a sustained period in the crop life cycle. Similarly, pesticides when applied to the soil are not available over a sustained period when pests or diseases appear and there is a need for providing the pesticides slowly over a period of time and minimize losses due to pest or disease attack. Moreover, prior art granular pesticide compositions tend to leach away due to their rapid dispersibility whereby the leached pesticides contribute to groundwater contamination in regions with intensive agriculture.

Water dispersible granules as such have been disclosed in U.S. Pat. No. 8,241,387 and WO2012131702 have been known for a very long time. While these granules instantly provide the nutrients, these granules have a poor attrition resistance, and practically no hardness. While these documents discloses granules in the size range of 0.1 mm to 2.5 mm and 0.75 mm to 5 mm, respectively, it is observed that the granules actually do not retain their integrity, including their size and shape, and have no mechanical strength to withstand post production handling, and break down to a fine dust. It has been observed that attrition caused during production, packaging, storage, handling and application of these granules or powders leads to a premature breakdown of these compositions resulting in substantial loss of release control, and excessive nutrient leaching. Furthermore, one of the biggest problems and challenges with these water dispersible granules is their application and dependence on labour. When applied through mechanical applicators (hoppers and drillers), such compositions get released at one location and cannot be distributed uniformly through mechanized means. Farmers typically apply mixtures of fertilizers in a single application. However, due to their form, these water dispersible granules need to be applied separately from other granular fertilizers such as urea. This makes it cumbersome for application and increases the cost of application for the farmer.

Moreover, both powder and granular formulations further tend to leach away, due to their instant and complete dispersibility in water. (See Column C, FIG. 5)

Pellet compositions of crop nutrients are also known, such as those formed with bentonite clay. Brimstone 90, Tiger 90, Growmor, Vitsul, etc. are some of the traditional brands available in the market. However, these pellets have a higher bulk density, high particle size and do not disperse or disintegrate well when applied to the soil. They also, do not provide nutrients when required by the crop. These pellets take a long time to be assimilated in the soil or at times remain as a whole or in the form of residues within the soil even after the crop has been harvested. As a result, they do not provide adequate amount of nutrients to the crop, thereby hampering crop nutrition during the early and growing periods. Furthermore, these compositions are also required to be applied at very high dosages of application. In the end, the use of these traditional pellets results in lower crop yields at high application costs to the farmer.

Furthermore, biological materials such as algae, bacteria and others are useful alternatives to chemical agents for improvement and maintenance of soil nutrients. Granular formulations with exterior coating of biological materials are also known. WO2016113665 discloses pellets with a deformable core, a binder and an exterior coat. The coating comprises two parts—the first coat comprises a biological material, and the second coat comprises a particular dessicant or binder. Thus, this entire granular composition owing to its large particle size and layers of coating, the composition suffers from poor dispersion and suspensibility, and in the end, poor efficacy. It is observed that since they swell when exposed to water, and in fact do not disperse, they cannot deliver the biological adequately to the crop. Hence, formulations of biological materials need to be optimized and their application needs to be improved in order to provide an economical result in terms of yield, plant growth, vitality and vigour to the farmer and also reduce the burden on the environment.

As of today, all prior art compositions of agricultural actives or crop nutrients or biological materials, when applied to the soil, suffer from disadvantages of application, inability to provide adequate nutrition and pest control, throughout the entire crop lifecycle, and losses due to leaching.

There remains a challenge to provide an agrochemical or crop nutrients or biological material or pesticidal actives in a form which provides the nutrient or agrochemical or pesticides for uptake immediately, and also for the entire duration of the crop cycle.

Consequently, making dry agricultural compositions less bulky, less dense, while retaining a large size and maintaining good attrition resistance, for ease of application, even when including a high amount of an insoluble material and yet having good dispersibility or disintegration properties is a great challenge. It is a further challenge to develop a composition which also remains suspended in water over a period of time to facilitate a uniform application on the soil. For e.g., it is observed that over a period of time, prior art compositions of water dispersible granules or broadcast granules or microgranules possess no strength to wear and tear, and do not retain their structure and turn to micron-sized fines during packaging and storage. As a result, these prior art compositions, cannot be applied uniformly in large fields through mechanical applicators.

There is a need to provide dry agricultural compositions, which can be applied through mechanical applicators along with other water soluble fertilizers such as urea and minimize the cost of application. There is also a need to ensure that crop nutrients or algae or pesticidal actives are available to the plant instantly and continuously during the growth stages in the crop lifecycle to provide for adequate plant nutrition, protein synthesis and plant protection. There is also a need to reduce losses due to leaching.

The inventor has surprisingly found for the first time that a composition comprising an agrochemical such as a water insoluble nutrient or algae or pesticides in a dry water disintegrable granular form, with a fine particle size distribution, a well-defined, low bulk density but also a high attrition resistance and hardness, good suspension, dispersion and disintegration properties in water and in the soil, and good wet sieve retention, surprisingly, enables a significant increase not only in the plant yield in terms of grain yield or oil content, but also a marked improvement in the uptake of essential nutrients by the plant along with improved physiological characteristics of the plant such as plant height, root length and improved foliage, and also improved control over soil borne pest and disease, with the application of the composition of the present invention. While prior art compositions provide nutrients instantaneously, they still leach away in the soil and cannot provide the requirements for the fertilizer till the later stages in the crop cycle. Surprisingly it has been observed, that the composition of the present invention makes water insoluble nutrients or algae or pesticides available instantaneously and also over a longer period of the crop cycle, providing an immediate and sustained release of water insoluble nutrients or algae or pesticides providing nourishment and protection to the crop at each and every stage.

4. SUMMARY OF THE INVENTION

The invention relates to an agricultural water disintegrable granular composition which includes at least one agrochemical active; at least one agrochemically acceptable excipient; wherein the composition is in a size range of 0.1 mm to 6 mm and comprises particles in the size range of from 0.1 micron to 50 microns. The composition has a hardness of at least 1 N but has a bulk density of less than 1.5 gm/ml. The composition also demonstrates good physical properties of disintegration, dispersion and suspension, good release properties for the entire crop life cycle. It has been surprisingly determined by the inventor that the composition with the above parameters of bulk density, hardness, and particle size distribution and granule size provide an instantaneous as well as continuous release of agrochemical over the crop cycle. Moreover, the composition exhibits a surprisingly higher field efficacy at significantly reduced dosages of application of the composition.

The invention relates to an agricultural water disintegrable granular composition which includes at least one water insoluble nutrient; at least one agrochemically acceptable excipient; wherein the composition is in a size range of 0.1 mm to 6 mm and comprises particles in the size range of from 0.1 micron to 50 microns. It has been surprisingly observed that composition not only has a hardness of at least 1 N but has a bulk density of less than 1.5 gm/ml.

According to an embodiment, the invention further relates to a process of preparing the water disintegrable granular composition, the process involving milling a blend of at least one water insoluble nutrient and at least one agrochemically acceptable excipient to obtain a wet mix as a slurry. The process further involves drying the wet mix or the slurry to obtain a powder or a granule. The granules obtained are further subjected to least one of agglomeration or pelletization or granulation to obtain the agricultural granular composition of one or more water insoluble nutrients. The agricultural granular composition obtained by the process has a hardness of at least 1N and a bulk density of less than 1.5 gm/ml, are in a size range of 0.1 mm to 6 mm and comprises particles in a size range of from 0.1 micron to 50 microns.

According to an embodiment, the invention further relates to the use of the water disintegrable granular composition of water insoluble nutrients as at least one of a nutrient composition, a fertilizer composition, a plant strengthener composition, a soil conditioner composition and a yield enhancer composition.

According to an embodiment, the invention further relates to a method of improving plant health, the method comprising treating at least one of a plant, a plant propagation material, a seed, seedling or surrounding soil with an agricultural water disintegrable granular composition comprising at least one water insoluble nutrient; and at least one agrochemically acceptable excipient; wherein the granules are in a size range of 0.1 mm to 6 mm, and have an attrition resistance of at least 50% and a hardness of at least 1N.

The invention also relates to an agricultural water disintegrable granular algal composition. More particularly, the invention relates to water disintegrable granular algal composition, comprising at least one algae, and at least one agrochemically acceptable excipient. Even more particularly the invention relates to water disintegrable granular composition comprising at least one algae and at least one agrochemically acceptable excipient wherein the composition is in a size range of 0.1 mm to 6 mm and comprises particles in the size range of from 0.1 micron to 50 microns, has a hardness of at least 1N and a bulk density of less than 1.5 g/ml. The composition also demonstrates good physical properties of disintegration, dispersion and suspension, good release properties for the entire crop life cycle. Moreover, the composition exhibits a surprisingly higher field efficacy at significantly reduced dosages of application of the composition.

According to an embodiment, the invention further relates to a process of preparing the water disintegrable granular composition comprising at least one algae and at least one agrochemically acceptable excipient, the process involving milling a blend of at least one algae and at least one agrochemically acceptable excipient to obtain a wet mix, as a slurry. The process further involves drying the wet mix to obtain the granules. The granules obtained are further subjected to least one of agglomeration or pelletization or granulation to obtain the agricultural granular composition of one or more algae. The agricultural granular composition obtained by the process has a bulk density of less than 1.5 g/ml and a hardness of at least 1N, have particles in the size range of 0.1-50 microns, granule size is in the range of 0.1 mm to 6 mm.

According to an embodiment, the invention further relates to the use of the water disintegrable granular algal composition as at least one of a nutrient composition, a plant strengthener composition, a soil conditioner composition and a yield enhancer composition.

According to an embodiment, the invention further relates to a method of improving plant health, the method comprising treating at least one of a plant, a plant propagation material, a seed, seedling or surrounding soil with the water disintegrable granular algal composition comprising at least one algae; and at least one agrochemically acceptable excipient; wherein the granules have a hardness of at least 1N and a bulk density of less than 1.5 g/ml.

The invention further relates to an agricultural water disintegrable granular composition which includes at least one pesticidal active ingredient; at least one agrochemically acceptable excipient; wherein the composition is in a size range of 0.1 mm to 6 mm and comprises particles in the size range of from 0.1 micron to 50 microns. It has been surprisingly observed that composition not only has hardness of at least 1 N but has a bulk density of less than 1.5 gm/ml.

According to an embodiment, the invention further relates to a process of preparing the agricultural granular composition, the process involving milling a blend of at least one pesticidal active ingredient and at least one agrochemically acceptable excipient to obtain a wet mix in the form of a slurry. The process further involves drying the slurry to obtain a granule. The granules obtained are further subjected to least one of agglomeration or pelletization or granulation to obtain the agricultural granular composition of one or more pesticidal active ingredients. The agricultural granular composition of pesticidal active ingredients obtained by the process has a hardness of at least 1N and a bulk density of less than 1.5 gm/ml, are in a size range of 0.1 mm to 6 mm and comprises particles in a size range of from 0.1 micron to 50 microns.

According to an embodiment, the invention further relates to the use of the agricultural granular composition of at least one pesticidal active ingredient as a plant protectant composition.

According to an embodiment, the invention further relates to a method of plant protection, the method comprising treating at least one of a plant, a plant propagation material, a seed, seedling or surrounding soil with an agricultural water disintegrable granular composition comprising at least one pesticidal active ingredient; and at least one agrochemically acceptable excipient; wherein the granules are in a size range of 0.1 mm to 6 mm, has a bulk density of less than 1.5 g/ml and a hardness of at least 1N.

5. BRIEF DESCRIPTION OF THE DRAWINGS

For a more complete understanding of the invention reference should now be made to the embodiments illustrated in greater detail in the accompanying drawings and described by way of embodiments of the invention.

FIG. 1 illustrates an image of the water disintegrable granular composition of 90% Sulphur water disintegrable granules as per an embodiment of the present invention.

FIG. 2 illustrates a post packaging and transportation image of the water dispersible granular composition of 90% Sulphur as per the teachings of WO2008084495. The image depicts extensive crumbling of the granules into finer particles during manufacture, processing, packaging and transportation, attributed to the poor attrition resistance and poor hardness of these granules.

FIG. 3 illustrates an image of the water disintegrable granular composition of Sulfur 70%+Zinc oxide 15% as per an embodiment of the present invention.

FIG. 4 illustrates an image of the water dispersible granular composition of Sulfur 70%+Zinc oxide 15% as per the teachings of WO2012131702, post packaging and transportation. FIG. 4 also exhibits extensive crumbling of the granules into fine particles as a result of manufacture, processing, packaging and transportation which is caused due to poor attrition and hardness of these granules as can be seen from Table 7.

FIG. 5 illustrates an image of the prior art sulphur 90% bentonite granules (A) in water, granules of sulphur 90% water disintegrable granules according to an embodiment of the invention (B) in water, and prior art sulphur 90% water dispersible granules according to the teachings of WO2008084495 (C), in water, right after initial application (time 0).

FIG. 6 illustrates an image of the prior art sulphur 90% bentonite granules (A) in water, granules of sulphur 90% water disintegrable granules according to an embodiment of the invention (B) in water, and prior art sulphur 90% water dispersible granules according to the teachings of WO2008084495 (C), in water, after 15 mins, without stirring.

FIG. 7 illustrates an image of the prior art sulphur 90% bentonite granules (A) in water, granules of sulphur 90% water disintegrable granules according to an embodiment of the invention (B) in water, and prior art sulphur 90% water dispersible granules according to the teachings of WO2008084495 (C), in water, after 30 mins, without stirring.

FIG. 8 illustrates an image of the prior art sulphur 90% bentonite granules (A) in water, granules of sulphur 90% water disintegrable granules according to an embodiment of the invention (B) in water, and prior art sulphur 90% water dispersible granules according to the teachings of WO2008084495 (C), in water, after 1 hour, without stirring.

FIG. 9 illustrates an image of the prior art sulphur 90% bentonite granules (A) in water, granules of sulphur 90% water disintegrable granules according to an embodiment of the invention (B) in water, and prior art sulphur 90% water dispersible granules according to the teachings of WO2008084495 (C), in water, after 2 hours, without stirring.

FIG. 10 illustrates an image of the prior art sulphur 90% bentonite granules (A) in water, granules of sulphur 90% water disintegrable granules according to an embodiment of the invention (B) in water, and prior art sulphur 90% water dispersible granules according to the teachings of WO2008084495 (C), in water, after 4 hours, without stirring.

Figure 11:
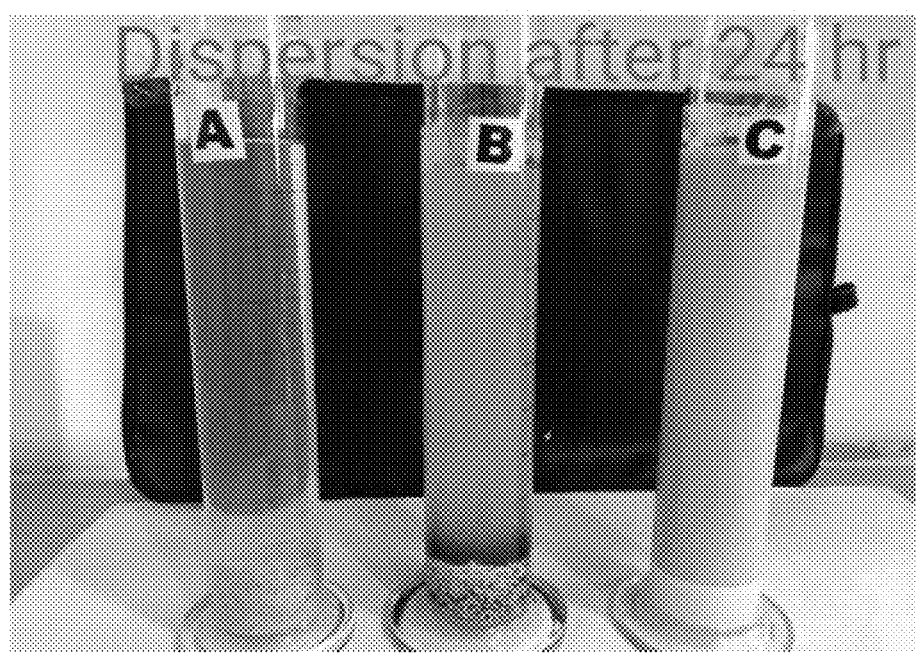

FIG. 11 illustrates an image of the prior art sulphur 90% bentonite granules (A) in water, granules of sulphur 90% water disintegrable granules according to an embodiment of the invention (B) in water, and prior art sulphur 90% water dispersible granules according to the teachings of WO2008084495 (C), in water, after 24 hours, without stirring.

6. DESCRIPTION OF THE INVENTION

In describing the embodiment of the invention, specific terminology is chosen for the sake of clarity. However, it is not intended that the invention be limited to the specific terms so selected and it is to be understood that each specific term includes all technical equivalents that operate in a similar manner to accomplish a similar purpose. For instance, in the context of the present invention, the term "agrochemical active" includes not only a chemical plant nutrient or water insoluble nutrient, or plant protectant or pesticidal active ingredient but also biological material such as algae and bacterial material.

The invention can relate to an agricultural water disintegrable granular composition which includes: at least one water insoluble nutrient and, at least one agrochemically acceptable excipient. The water disintegrable granules are in a size range of 0.1 mm to 6 mm and include particles in a size range of from 0.1 micron to 50 microns.

According to another embodiment, the agricultural granular composition is in a size range of 0.1 mm to 6 mm. According to another embodiment, the agricultural granular composition is in a size range of 0.5 mm to 6 mm. According to another embodiment, the agricultural granular composition has a granule size in the range of 1 mm to 6 mm. According to another embodiment, the agricultural granule size range of 1 mm to 5 mm. According to another embodiment, the agricultural granule size is in the range of 2 mm to 5 mm.

According to an embodiment, the granules comprise particles in a size range of 0.1 microns to 50 microns. According to an embodiment, the granules comprise particles in a size range of 0.1 microns to 40 microns. According to an embodiment, the granules comprise particles in a size range of 0.1 microns to 30 microns. According to an embodiment, the granules comprise particles in a size range of 0.1 microns to 20 microns. According to an embodiment, the granules comprise particles in a size range of 0.1 microns to 15 microns. According to an embodiment, the granules comprise particles in a size range of 0.1 microns to 10 microns.

According to an embodiment, the water insoluble nutrient includes a water insoluble fertilizer or a micronutrient. According to an embodiment, the water insoluble nutrient comprises a mixture of one or more water insoluble fertilizers and one or more of micronutrients or their salts or derivatives or complexes thereof. According to an embodiment, the water insoluble fertilizer is at least one of a single nutrient fertilizers, multi-nutrient fertilizers, binary fertilizers, compound fertilizers, organic fertilizers, derivatives or mixtures thereof. However, those skilled in the art will appreciate that it is possible to utilize other fertilizers known in the art, without departing from the scope of the invention. According to an embodiment, the water insoluble fertilizer is one or more of nitrogen, phosphorous and potassium fertilizers or sulphur fertilizers, such as elemental sulphur.

According to an embodiment, the water insoluble nutrient includes but is not limited to Boron, Calcium, Chlorine, Chromium, Cobalt, Copper, Fluorine, Iodine, Iron, Magnesium, Manganese, Molybdenum, Phosphorous, Potassium, Selenium, Silicon, Sodium, Zinc, in their elemental form or salts or derivatives of these elements.

According to an embodiment, the water insoluble nutrient includes one or more of elemental boron, Boron carbide, Boron nitride, Aluminum oxide, Aluminum dodecaboride, aluminum hydroxide, bauxite, calcitic limestone, Calcium oxalate, Chromium oxide, Cobalt oxide, Cobalt sulphide, Cobalt molybdate, Cobalt carbonate, Copper oxalate, Copper oxide, Copper Sulphide, Copper hydroxide, Cupric sulphide, Copper phosphate, Copper molybdate, Fluorine oxide, Fluorine molybdate, Iron oxide, Iron sulphide, Magnesium oxide, Magnesium hydroxide, Magnesium phosphate tribasic, Magnesium molybdate, Magnesium carbonate, Manganese oxide, Manganese molybdate, Molybdenum acetate, Molybdenum disulphide, Selenium sulphide, Silicon nitride, Zinc sulphide, Zinc oxide, Zinc carbonate, Zinc phosphate, Zinc molybdate, basic slag, elemental chromium, chromium phosphate, iron sucrate, cobalt phosphide, cobalt cyanide, elemental nickel, nickel oxide, nickel oxyhydroxide, nickel carbonate, nickel chromate, nickel hydroxide, millerite, nickel selenide, nickel phosphide, elemental copper, insoluble copper cyanide, chalcocite, copper selenide, copper phosphide, covellite, copper arsenate, elemental silver, elemental zinc, zinc chromate, zinc pyrophosphate, tin hydroxide, tin oxide and tin sulfide, their salts, derivatives and combinations thereof. However, those skilled in the art will appreciate that it is possible to use other water insoluble nutrients without departing from the scope of the present invention.

According to an embodiment, the water insoluble nutrient can be a vitamin, such as, but not limited to Vitamin A, Vitamin B, Vitamin C, Vitamin D, Vitamin E and Vitamin K. However, those skilled in the art will appreciate that it is possible to use other vitamins without departing from the scope of the present invention.

According to an embodiment, the water insoluble nutrient is present in a concentration range of at least 0.1% by weight of the total composition. According to an embodiment, the water insoluble nutrient is present in a concentration range of at least 1% by weight of the total composition. According to an embodiment, the water insoluble nutrient is present in a concentration range of at least 5% by weight of the total composition. According to another embodiment, the water insoluble nutrient is present in an amount of at least 10%. According to another embodiment, the water insoluble nutrient is present in an amount of at least 20%. According to another embodiment, the water insoluble nutrient is present in an amount of at least 30%. According to another embodiment, the water insoluble nutrient is present in an amount of at least 40%. According to another embodiment, the water insoluble nutrient is present in an amount of at least 50%. According to another embodiment, the water insoluble nutrient is present in an amount of at least 60%. According to another embodiment, the water insoluble nutrient is present in an amount of at least 70%. According to yet another embodiment the composition comprises at least 80% by weight of the water insoluble nutrient. According to another embodiment the composition comprises at least 90% by weight of the water insoluble nutrient. According to another embodiment the composition comprises at least 95% by weight of the water insoluble nutrient.

The invention also relates to an agricultural water disintegrable granular composition which includes at least one algae and at least one agrochemically acceptable excipient. The water disintegrable granules are in a size range of 0.1 mm to 6 mm and include particles in a size range of from 0.1 micron to 50 microns.

According to another embodiment, the agricultural water disintegrable granular composition is in a size range of 0.1 mm to 6 mm. According to another embodiment, the agricultural granular composition is in a size range of 0.5 mm to 6 mm. According to another embodiment, the agricultural granular composition has a granule size in the range of 1 mm to 6 mm. According to another embodiment, the agricultural granule size range of 1 mm to 5 mm. According to another embodiment, the agricultural granule size is in the range of 2.5 mm to 5 mm.

According to an embodiment, the granules comprise particles in a size range of 0.1 microns to 50 microns. According to an embodiment, the granules comprise particles in a size range of 0.1 microns to 40 microns. According to an embodiment, the granules comprise particles in a size range of 0.1 microns to 30 microns. According to an embodiment, the granules comprise particles in a size range of 0.1 microns to 20 microns. According to an embodiment, the granules comprise particles in a size range of 0.1 microns to 15 microns. According to an embodiment, the granules comprise particles in a size range of 0.1 microns to 10 microns.

According to another embodiment, the algae can be microalgae, salt water algae or freshwater algae or species, derivatives or mixtures thereof.

According to further embodiment, the algae can be at least one belonging to the group selected from green algae, red algae, golden algae, brown algae, golden-brown algae, blue algae or blue-green algae, Asian tuen shaped flat algaes or sea weeds or their derivatives, species and mixtures thereof.

According to still further embodiment, the algae can be at least one selected from the division, but not limited to Cyanobacteria (*Cyanophyta*), Ochrophytes, Glaucophytes, Pyrrophytes, Rhodophytes, Chrysophyta, Raphidophytes, Eustigmatophytes, Synurophytes, Silicoflagellates, Sarcinochrysophyceae, Heterokonts, Cryptophytes, Haptophytes, Euglenophytes, Chlorophytes, Charophytes, Land Plants, Embrophyta Or Chlorarachniophytes or their derivatives, species and mixtures thereof. However, those skilled in the art will appreciate that it is possible to utilize any other algae known in the art from other division, without departing from the scope of the invention.

According to further embodiment, the algae can be at least one selected from the family, but not limited to Bryopsidaceae, Acrotylaceae, Areschougiaceae, Phaeophyceae, Cystocloniaceae, Dicranemataceae, Hypneaceae, Raphidiophyceae, Eustigmatophyceae Dumontiaceae, Caulerpaceae, Codiaceae, Halimedaceae, Udoteaceae, Anadyomenaceae, Polyphysaceae, Siphonocladaceae, Valoniaceae, Ulvaceae, Chordariaceae, Punctariaceae, Dictyotaceae, Ectocarpaceae, Rhodymeniaceae, Gelidiaceae, Cystoseiraceae, Sargassaceae, Sporochnaceae, Sphacelariaceae, Scytosiphonaceae, Sarcinochrysophyceae, Alariaceae, Gracilariaceae, Rhizophyllidaceae, Porphyridiaceae, Acrochaetiaceae, Bonnemaisoniaceae, Ceramiaceae, Dasyaceae, Rhodomelaceae, Delesseriaceae, Phacelocarpaceae, Halymeniaceae, Liagoraceae, Chrysomonadales, Chrysocapsales, Chrysosphaerales, Chrysotrichales, Heterokontae, Diatomeae, Galaxauraceae, Plocamiaceae, Champiaceae, Sebdeniaceae, Lomentariaceae, Peyssonneliaceae, Nizymeniaceae, Kallymeniaceae, Corallinaceae, Nemastomataceae, Xanthophyceae or their derivatives, species and mixtures thereof. However, those skilled in the art will appreciate that it is possible to utilize any other algae known in the art from other family, without departing from the scope of the invention.

According to still further embodiment, the algae can be at least one belonging to the genus selected from, but not limited to *Spirulina* Sp., *Nitzschia* Sp., *Navicula* Sp., *Ahnfeltia* Sp., *Anikstrodesmis* Sp., *Arthrospira* Sp., *Nannochloris* Sp. *Asteromenia* Sp., *Botryocladia* Sp., *Chlorella* Sp., *Haematococcus* Sp., *Dunaliella* Sp., *Selenasirum* Sp., *Nannochhropsis* Sp., *Scenedesm* Sp., *Graciaria* Sp., *Oscillatoria* Sp., *Phormidium* Sp., *Nemastoma* Sp., *Amphora* Sp., *Oehromonas* Sp. *Cyanidioschyzon* Sp., *Caulerpa* Sp., *Dictyosphaeria* Sp., *Haliptilon* Sp., *Atracto phora* Sp., *Valonia* Sp., *Boodlea* Sp., *Gelidiella* Sp., *Ceratodictyon* Sp., *Pneophyllum* Sp., *Kallymenia* Sp., *Predaea* Sp, *Siphonocladus* Sp., *Cladophoropsis* Sp., *Amphiplexia* Sp., *Lemanea* Sp., *Mesophyllum* Sp., *Palmaria* Sp., *Cladosiphon* Sp., *Schmitzia* Sp., *Colpomenia* Sp., *Cryptophycees* Sp., *Metagoniolithon* Sp., *Hydrolithon* Sp., *Hypoglossum* Sp., *Seirospora* Sp., *Jania* Sp., *Florideophyceae* Sp., *Metamastophora* Sp., *Amphiroa* Sp., *Acanthophora* Sp., *Chondrus* Sp., *Cottoniella* Sp., *Pleonosporium* Sp., *Ditria* Sp., *Endosiphonia* Sp., *Doxodasya* Sp., *Drewiana* Sp., *Dictyomenia* Sp., *Antithamnion* Sp., *Platysiphonia* Sp., *Heterodoxia* Sp., *Dasyclonium* Sp., *Chondria* Sp., *Haraldiophyllum* Sp., *Aglaothamnion* Sp., *Struvea* Sp., *Sarcomenia* Sp., *Acrothamnion* Sp., *Martensia* Sp., *Lejolisia* Sp., *Haloplegma* Sp., *Griffithsia* Sp., *Glaphrymenia* Sp, *Dasya* Sp., *Acrosorium* Sp., *Spyridia* Sp., *Hemineura* Sp., *Wrangelia* Sp., *Trithamnion* Sp., *Dasyphila* Sp., *Claudea* Sp., *Corallophila* Sp., *Perischelia* Sp., *Monosporus* Sp., *Carpothamnion* Sp., *Guiryella* Sp., *Gattya* Sp., *Mastocarpus* Sp., *Anotrichium* Sp., *Centroceras* Sp., *Ceramium* Sp., *Caulerpa* Sp., *Vanvoorstia* Sp., *Euptilocladia* Sp., *Titanophora* Sp., *Tanakaella* Sp., *Asparagopsis* Sp., *Lithophyllum* Sp., *Acrochaetium* Sp., *Euptilota* Sp., *Audouinella* Sp., *Botryococcus* Sp., *Actmanthes* Sp., *Ahnfeltiopsis* Sp., *Agmenemum* Sp., *Cochlodinium* Sp., *Amphiprora* Sp., *Anftistrodesnms* Sp., *Ammsirodesnms* Sp., *Borodinetta* Sp., *Carteria* Sp., *Stylonema* Sp., *Chaetoceros* Sp., *Chlamydomas* Sp., *Chlorococcuni* Sp., *Chlorogoni* Sp., *Chroomonas* Sp., *Chrysosphaera* Sp., *Ciicosphaera* Sp., *Cryptothecodinium* Sp., *Cryptomonas* Sp., *Cyclotella* Sp., *Dimaliella* Sp., *Eremosphaera* Sp., *Ellipsoidon* Sp., *Euglena* Sp., *Franceia* Sp., *Gloeocapsa* Sp., *Fragilaria* Sp., *Gleocapsa* Sp., *Gloeothamnion* Sp., *Cyanospira* Sp., *Hymenomonas* Sp., *Bockrysis* Sp., *Hochrysis* Sp., *Lepocinclis* Sp., *Stauroneis* Sp., *Micraclinium* Sp., *Chrysymenia* Sp., *Micractinhnn* Sp., *Monaraphidium* Sp., *Nannochloris* Sp., *Navicida* Sp., *Porphyridium* Sp., *Nizymania* Sp., *Scenedesmus* Sp., *Synechoccus* Sp. *Navicul* Sp., *Nephrochloris* Sp., *Odontella* Sp., *Muriellopsis* Sp., *Tschia* Sp., *Nitzschia* Sp., *Isochrysis* Sp., *Phaedactylum* Sp., *Lyngbya* Sp., *Aphanizomenonflos* Sp., *Ochromonas* Sp., *Oocyst* Sp., *Bacillariophyceae* Sp., *Pamchlorelta* Sp., *Peyssonnelia* Sp., *Pascheria* Sp., *Pavlova* Sp., *Phaeodactyhan* Sp., *Cylindrospermum* Sp., *Tolypothrix* Sp., *Hapalosiphon* Sp., *Cylindrotheca* Sp., *Anacystis* Sp., *Ertilissima* Sp., *Aulosira* Sp., *Phortmdium* Sp., *Platytnonas* Sp., *Pleurochrysis* Sp., *Leptolyngbya* Sp., *Neochloris* Sp., *Prototheca* Sp., *Pseudochlorella* Sp., *Hormotilopsis* Sp., *Gyrodinium* Sp., *Ellipsoidion* Sp., *Pyramimonas* Sp., *Pyrobotrys* Sp., *Sarcinoid* Sp., *Aminariaceae* Sp., *Schizochytrmm* Sp., *Spirogyra* Sp., *Stichococcus* Sp., *Synechococcus* Sp., *Synechocystisf* Sp., *Tagetes* Sp., *Tetraedron* Sp., *Tetraselmis* Sp., *Thalassiosira* Sp., *Viridiella* Sp., *Alaria* Sp., *Saccharina* Sp., *Coelarthrum* Sp., *Nereocystis* Sp., *Laminaria* Sp., *Por-* phyra Sp., Phaeocystis Sp., Aphanocapsa Sp., Phacelocarpus Sp., Ulva Sp., Himanthalia Sp., Cyanothece Sp., Ascophyllum Sp., Focus Sp., Kappaphycus Sp., Betaphycus Sp., Gelidium Sp., Planktothricoides Sp., Prochlorococcus Sp., Prochloron Sp., Prochlorothrix Sp., Blastophysa Sp., Pedinomonas Sp., Resultor Sp., Marsupiomonas Sp., Chlorokybus Sp., Coleochaete Sp., Awadhiella Sp., Prymnesiophycees Sp., Radioramus Sp., Conochaete Sp., Choristocarpaceae Sp., Lithothamnion Sp., Phymatolithion Sp., Discosporangiaceae Sp., Ishigeaceae Sp., Petrodermataceae Sp., Syringodermataceae Sp., Portieria Sp., Onslowiaceae Sp., Dictyotaceae Sp., Lithodermataceae Sp., Eustigmatophyte Sp., Phaeostrophionaceae Sp., Amphidinum Sp., Sphacelodermaceae Sp., Micractinium Sp., Sargassum Sp., Curdiea Sp., Stypocaulaceae Sp., Coelothrix Sp., Cladostephaceae Sp., Sphacelariaceae Sp., Fucus Sp., Asterocladaceae Sp., Lessoniaceae Sp., Ascoseiraceae Sp., Cutleriaceae Sp., Eklonia Sp., Arthrocladiaceae Sp., Desmarestiaceae Sp., Acinetosporaceae Sp., Adenocystaceae Sp., Chlamydomonas Sp., Cladophora Sp., Prasinophyceae Sp., Chordariaceae Sp., Chordariopsidaceae Sp., Gelidiopsis Sp., Agmenellum Sp., Desmodesmus Sp., Ectocarpaceae Sp., Mesosporaceae Sp., Halydris Sp., Myrionemataceae Sp., Pylaiellaceae Sp., Bifurcariopsidaceae Sp., Chlorococcum Sp., Durvillaeaceae Sp., Fucaceae Sp., Glossomastix Sp., Himanthaliaceae Sp., Iridaea Sp., Hormosiraceae Sp., Notheiaceae Sp., Sargassaceae Sp., Acrosiphonia Sp., Seirococcaceae Sp., Goniochloris Sp., Gloeothece Sp., Emiliana Sp., Codium Sp., Akkesiphycaceae Sp., Alariaceae Sp., Monochrysis Sp., Palma Sp., Chordaceae Sp., Acetabularia Sp., Phaffia Sp., Costariaceae Sp., Platymonia Sp., Pseudochordaceae Sp., Nemodermataceae Sp., Neoralfsiaceae Sp., Mphora Sp., Rhodymenia Sp., Ralfsiaceae Sp., Analipus Sp., Chnoosporaceae Sp., Egregia Sp., Scytosiphonaceae Sp., Chaetomorph Sp., Scytothamnaceae Sp., Gymnogongrus Sp., Asperococcus Sp., Bryopsis Sp., Rhizoclonium Sp., Gloiocladia Sp., Ecklonia Sp, Girgatina Sp., Hymenocladia Sp., Lomentaria Sp., Schizochytrium Sp., Aphanotece Sp., Splachnidiaceae Sp., Sporochnaceae Sp., Plocamium Sp., Constantinea Sp., Cryptosiphonia Sp., Webervanboassea Sp., Lessoniopsis Sp., Chondracanthus Sp., Halosiphonaceae Sp., Dictyopteris Sp., Farlowia Sp., Anadyomene Sp., Apelvetia Sp., Endocladia Sp., Heterokontophyta Sp., Coralline Sp., Thraustochytrium Sp., Osmundea Sp., Callophyllis Sp. M Calliarthron Sp., Monoraphidium Sp., Penicillus Sp., Meristotheca Sp., Wrack Sp., Cosmocladium Sp., Calothrix Sp., Polysiphonia Sp., Prionitis Sp., Leathesia Sp., Polyneura Sp., Pelvetiopsis Sp., Chlamidonomas Sp., Neorhodomela Sp., Microdictyon Sp., Masonophycaceae Sp., Melobesia Sp., Dinoflagellate Sp., Delesseria Sp., Phyllariaceae Sp., Postelsia Sp., Microcladia Sp., Stschapoviaceae Sp., Dilsea Sp., Halimeda Sp., Chroococus Sp., Tilopteridaceae Sp., Phaeodactylum Sp., Semnocarpoa Sp., Champia Sp., Erythrophyllum Sp., Chodium Sp., Paonia Sp., Ulothrix Sp., Heterochordariaceae Sp., Gracilaria Sp., Rivularia Sp., Phromidium Sp., Stypopodium Sp., Erythrocladia Sp., Bracchiomonas Sp., Coradophylum Sp., Cyanophyta Sp., Dysmorphococcus Sp., Cystoseira Sp., Dilophus Sp., Gloiotrichus Sp., Liagora Sp., Eisenia Sp., Ganonema Sp., Hennedya Sp., Codiophyllum Sp., Ecklonia Sp., Distromium Sp., Sparlingia Sp., Gastrocelonium Sp., Claviclonium Sp., Pelvetia Sp., Mazzaella Sp., Lobophora Sp., Pterocladia Sp., Scinaia Sp., Galaxaura Sp., Gloiopeltis Sp., Scillatoria Sp., Hypnea Sp., Hormophysa Sp., Dotyophycus Sp., Opuntiella Sp., Nannochloropsis. Sp., Myriodesma Sp., Tricleocarpa Sp., Trichogloea Sp., Yamadaella Sp., Sebdenia Sp., Gelinaria Sp., Prymnesium Sp., Herposiphonia Sp., Jeannerettia Sp., Kuetzingia Sp., Laurencia Sp., Lenormandiopsis Sp., Halymenia Sp., Eucheuma Sp., Erythroclonium Sp., Achnanthes Sp., Rhodopeltis Sp., Dudresnaya Sp., Halosaccion Sp., Zonaria Sp., Areschougia Sp., Hincksia Sp., Osmundaria Sp., Placophora Sp., Lophocladia Sp., Macrocystis Sp., Callophycus Sp., Microcoleus Sp., Epiphloea Sp., Acrosymphyton Sp., Cryptonemia Sp., Enteromorpha Sp., Neurymenia Sp., Lophosiphonia Sp., Microcystis Sp., Protokuetzingia Sp., Leveillea Sp., Caulocystis Sp., Hydroclathrus Sp., Scaberia Sp., Rosenvingea Sp., Schizothrix Sp., Rhodella Sp., Spirocladia Sp., Acrochaetium Robustum Bergesen, Tolypiocladia Sp., Tylotus Sp., Dicranema Sp., Pachydictyon Sp., Austronereia Sp., Sporochnus Sp., Craspedocarpus Sp., Solieria Sp., Encyothalia Sp., Nanococcus Sp., Gracilaria Sp., Grateloupia Sp., Hildenbrandiasp., Amphiroa Sp., Cheilosporum Sp., Corallina Sp., Hydrolithonsp., Hydrolithonsp., Jania Sp., Lithophyllumsp., Catenella Sp., Chondracanthus Sp., Hypnea Flagelliformissp., Ahnfeltiopsis Sp., Champia Sp., Gastroclonium Sp., Gelidiopsis Sp., Gaylielaflaccidasp., Aglaothamnion Sp., Crouania Sp., Ptilothamnion Sp., Dasya Sp., Caloglossa Sp., Aloglossa Sp., Erythroglossum Sp., Martensia Fragilissp., Bostrychia Sp., Chondria Sp., Herposiphonia Sp., Laurencia Obtusesp., Neosiphonia Sp., Polysiphonia Sp., Vaucheria Sp., Feldmannia sp., Hinksia Sp., Ralfsiasp., Sphacelaria Sp., Canistrocarpus Sp., Dictyota Sp., Padina Sp., Spatoglossum Sp., Spatoglossum Sp., Stoechospermum Sp., Chnoospora Sp., Iyengaria Sp., Gayralia Sp., Chaetomorpha Sp., Cladophora Sp., Cladophoropsis Sp., Phyllodictyon Sp., Valoniopsis Sp., Bryopis Sp., Caulerpa Sp., Avrainvillea Sp., Chlorodesmis Sp., or derivatives and mixtures thereof. However, those skilled in the art will appreciate that it is possible to utilize any other genus of algae known in the art, without departing from the scope of the invention. The algae are commercially manufactured and available through various companies.

According to another embodiment, the algae can be at least one species selected from, but not limited to: Anabena cylindrical, Bryopsis australis, Bryopsis minor, Botryococcus braunii, Actmanthes orientalis, Amphiprora hyaline, Amphora coffeiformis, Petrocelis Sp., Amphora cqffeifoiinis Var. linea, Chlorideila simplex, Apelvetia canaliculata, Caulerpa taxifolia, Amphora cqffeiformis Var. punctata, Amphora cqffeiformis Var. taylori, Ulva paschima bast, Cladophora goensis bast, Laurencia spectabilis, Gymnogongrus crenulatus, Opuntiella californica, Gymnogongrus griffithsiae, Achnanthes orientalis, Cladosiphon filum, Goniochloris sculpta, Ecklonia cava, Osmundea spectabilis, Neorhodomela larix, Asperococcus bullosus, Caulerpa cactoides, Gelidium micropterum, Caulerpa cliftonii, Caulerpa cupressoides, Caulerpa fergusonii, Caulerpa lentillifera, Caulerpa mexicana, Ahnfeltia plicata, Caulerpa obscura, Caulerpa racemosa, Caulerpa racemosa Var. corynephora, Caulerpa racemosa Var. laetivirens, Caulerpa racemosa Var. lamourouxii, Caulerpa racemosa Var. peltata, Caulerpa serrulata, Caulerpa simpliciuscula, Asteromenia peltata, Botryocladia skottsbergii, Ceratodictyon spongiosum, Chrysymenia kaernbachii, Chrysymenia ornata, Coelarthrum cliftonii, Coelothrix irregularis, Gelidiopsis variabilis, Gloiocladia halymenioides, Pterocladia capillacea, Prymnesium parvum, Gloiocladia indica, Gloiocladia rubrispora, Gloiosaccion brownii, Gelidium pusillum, Hymenocladia usnea, Phymatolithion calcereum, Lithothamnion calcareoum, Herposiphonia secunda, Herposiphonia secunda F. tenella, Heterostroma nereidiis, Jeannerettia lobata, Jeannerettia pedicellata, Kuetzingia canaliculata, Laurencia brongniartia, Laurencia cruciata, Laurencia filiformis, Laurencia majuscula, Laurencia papillosa, Lenormandiopsis latifolia, Leveillea jungermannioides, Lophocladia harveyi, Lophosiphonia prostrata, Neurymenia fraxinifolia, Osmundaria spiralis, Placophora binderi, Polysiphonia decipiens, Polysiphonia gracilis, Protokuetzingia australasica, Spirocladia barodensis, Tolypiocladia glomerulata, Amphiroa anceps, Amphiroa foliacea, Amphiroa gracilis, Haliptilon roseum, Hydrolithon farinosum, Hydrolithon onkodes, Jania pulchella, Lithophyllum bermudense, Mesophyllum engelhartii, Mesophyllum erubescens, Mesophyllum funafutiense, Metagoniolithon radiatum, Metagoniolithon stelliferum, Metamastophora flabellata, Pneophyllum fragile, Gelidium austral, Pterocladia lucida, Gelidiella pannosa, Amphiplexia hymenocladioides, Claviclonium ovatum, Hennedya crispa, Areschougia ligulata, Callophycus serratus, Callophycus oppositifolius, Erythroclonium sonderi, Eucheuma denticulatum, Eucheuma gelatinum, Eucheuma speciosum, Meristotheca papulosa, Solieria robusta, Craspedocarpus venosus, Dicranema revolutum, Tylotus obtusatus, Acrosymphyton taylorii, Dudresnaya capricornica, Rhodopeltis borealis, Hypnea spinella, Hypnea valentiae, Stylonema alsidii, Audouinella saviana, Asparagopsis armata, Asparagopsis taxiformis, Acrothamnion preissii, Aglaothamnion cordatum, Anotrichium tenue, Antithamnion antillanum, Antithamnion armatum, Antithamnion hanovioides, Carpothamnion gunnianum, Centroceras clavulatum, Ceramium filicula, Ceramium flaccidum, Ceramium isogonum, Ceramium macilentum, Ceramium mazatlanense, Ceramium puberulum, Ceramium sherpherdii, Ceramium sympodiale, Corallophila huysmansii, Dasyphila preissii, Drewiana nitella, Euptilocladia spongiosa, Euptilota articulata, Gattya pinnella, Griffithsia ovalis, Guiryella repens, Haloplegma preissii, Lejolisia aegagropila, Monosporus indicus, Perischelia glomulifera, Pleonosporium caribaeum, Seirospora orientalis, Spyridia filamentosa, Tanakaella itonoi, Trithamnion gracilissimum, Wrangelia plumosa, Dasya lyengarii, Dasya pilosa, Acrosorium decumbens, Claudea elegans, Cottoniella filamentosa, Haraldiophyllum erosum, Hemineura frondosa, Heterodoxia denticulata, Hypoglossum caloglossoides, Hypoglossum revolutum, Martensia australis, Martensia fragilis, Platysiphonia corymbosa, Platysiphonia delicata, Platysiphonia marginalis, Sarcomenia delesserioides, Acanthophora dendroides, Acanthophora spicifera, Chondria curdieana, Chondria dangeardii, Chondria lanceolata, Dasyclonium flaccidum, Dasyclonium incisum, Dictyomenia sonderi, Dictyomenia tridens, Ditria expleta, Doxodasya bolbochaete, Endosiphonia spinuligera, Rhodymenia leptophylla, Rhodymenia sonderi, Webervanboassea splachnoides, Glaphrymenia pustulosa, Kallymenia cribrogloea, Kallymenia cribrosa, Nemastoma damaecornis, Predaea laciniosa, Predaea weldii, Titanophora weberae, Nizymania conferta, Peyssonnelia capensis, Peyssonnelia inamoena, Phacelocarpus alatus, Portieria hornemannii, Curdiea obesa, Gracilaria canaliculata, Gracilaria preissiana, Gracilaria textorii, Codiophyllum flabelliforme, Erythrocladia irregularis, Cryptonemia kallymenioides, Epiphloea bullosa, Gelinaria ulvoidea, Halymenia floresia, Sebdenia flabellata, Porphyra crispate kjellman, Gracilaria corticata, Gracilaria foliifera, Gracilaria verrucosa, Grateloupia filicina, Grateloupia filicina F. horrida, Grateloupia lithophila, Peyssonnelia obscura, Hildenbrandia rubra, Amphiroa anceps, Amphiroa fragilissima, Amphiroa rigida, Cheilosporum spectabile, Corallina officinalis, Hydrolithon farinosum, Hydrolithon reinboldii, Jania rubens, Lithophyllum orbiculatum, Catenella caespitose, Chondracanthus acicularis, Hypnea flagelliformis, Hypnea musciformis, Hypnea spinella, Hypnea valentiae, Ahnfeltiopsis pygmaea, Champia compressa, Champia parvula, Gastroclonium compressum, Gelidiopsis variabilis, Antithamnion cruciatum, Ceramium cimbricum, Ceramium cruciatum, Gayliella flaccida, Aglaothamnion tenuissimum, Crouania attenuata, Ptilothamnion speluncarum, Wrangelia argus, Dasya ocellata, Caloglossa leprieurii, Aloglossa ogasawaraensis, Erythroglossum lusitanicum, Hypoglossum hypoglossoides, Acanthophora muscoides, Bostrychia radicans, Bostrychia tenella, Chondria armata, Chondria capillaries, Herposiphonia secunda, Laurencia obtuse, Neosiphonia ferulacea, Polysiphonia atlantica. Polysiphonia denudate, Vaucheria longicaulis, Feldmannia indica, Feldmannia irregularis, Hinksia mitchelliae, Ralfsia verrucosa, Sphacelaria rigidula, Canistrocarpus cervicornis, Canistrocarpus crispatus, Canistrocarpus magneanus, Dictyopteris australis, Dictyota bartayresiana, Dictyota ceylanica, Dictyota ciliolate, Dictyota dichotoma, Dictyota divaricata, Dictyota dumosa, Padina antillarum, Padina australis, Padina boryana, Padina gymnospora, Padina pavonica, Spatoglossum asperum, Spatoglossum variabile, Stoechospermum polypodioides, Chnoospora minima, Colpomenia sinuosa, Iyengaria stellata, Rosenvingea orientalis, Sargassum cinctum, Sargassum cinereum, Sargassum crassifolium, Sargassum glaucescens, Sargassum ilicifolium, Sargassum plagiophyllum, Sargassum polycystum, Sargassum prismaticum, Sargassum swartzii, Sargassum tenerrimum, Sargassum vulgare, Gayralia oxysperma, Ulva clathrata, Ulva compressa, Ulva conglobata, Ulva flexuosa, Ulva intestinalis, Ulva rigida, Ulva taeniata, Chaetomorpha antennina, Chaetomorpha linum, Chaetomorpha spiralis, Cladophora bombayensis, Cladophora coelothrix, Cladophora glomerata, Cladophora lehmanniana, Cladophora prehendens, Cladophora prolifera, Cladophora rhizoclonioidea, Cladophora saracenica, Cladophora socialis, Cladophora vagabunda, Rhizoclonium tortuosum, Boodlea composite, Cladophoropsis sundanensis, Phyllodictyon anastomosans, Valoniopsis pachynema, Bryopis hypnoides, Bryopsis pennata, Bryopsis plumose, Caulerpa peltata, Caulerpa racemosa, Caulerpa scalpelliformis, Caulerpa sertularioides, Caulerpa verticillata, Avrainvillea erecta, Chlorodesmis hildebrandtii, Dotyophycus abbottiae, Ganonema farinosa, Gloiotrichus fractalis, Liagora setchellii, Trichogloea requienii, Yamadaella, Galaxaura marginata, Galaxaura obtusata, Galaxaura rugosa, Scinaia tsinglanensis, Tricleocarpa cylindrica, Plocamium preissianum, Champia compressa, Champia pravula, Champia zostericola, Lomentaria corallicola, Lomentaria monochlamydea, Semnocarpoa minuta, Caulerpa webbiana, Caulerpa racemosa Var. turbinata neorhodomela oregona, Odonthalia floccose, Odonthalia floccosa forma comosa, Odonthalia washingtoniensis, Ecklonia kurome, Mastocarpus jardinii, Acetabularia calyculus, Halimeda cuneata, Padina sp., Porphyra suborbiculata, Porphyra vietnamensis, Cladophoropsis herpestica, Siphonocladus tropicus, Struvea plumosa rhodella maculate, Polysiphonia hendryi, Ecklonia stoloifera, Microcladia borealis, Microdictyon umbilicatum, Ecklonia maxima, Ecklonia radiate, Nereocystis luetkeana, Penicillus nodulosus, Ecklonia bicyclis and Ecklonia arborea, Eisenia bicyclis, Eisenia arboraea, Halosaccion glandiforme, Amphora coffeiformis Var. tenuis, Dictyosphaeria cavernosa, Dictyopteris muelleri, Dictyopteris plagiogramma, Dictyota ciliolata, Dictyota dichotoma, Dictyota dichotoma Var intricata, Dictyota furcellata, Dictyota mertensii, Dictyota naevosa, Dilophus crinitus, Dilophus fastigiatus, Dilophus robustus, Distromium flabellatum, Lobophora variegata, Pachydictyon paniculatum, Sargassum boryi, Sargassum decurrens, Sargassum distichum, Sargassum fallax, Sargassum ligulatum, Sargassum linearifolium, Sargassum podacanthum, Sargassum spinuligerum, Sargassum tristichum, Padina boergesenii, Padina elegans, Padina sanctae-crucis, Padina tenuis, Stypopodium australasicum, Stypopodium flabelliforme, Zonaria turneriana, Hincksia mitchelliae, Caulocystis uvifera, Cystoseira trinodis, Hormophysa cuneiformis, Myriodesma quercifolium, Scaberia agardhii, Ecklonia radiata, Hydroclathrus clathratus, Sphacelaria biradiata, Sphacelaria novae-hollandiae, Sphacelaria rigidula, Austronereia australis, Encyothalia cliftonii, Sporochnus comosus, Dictyosphaeria versluysii, Amphora delicatissima, Amphora delicatissima Var. capitata, Cosmocladium perissum, Anabaena, Anadyomene brownie, Anftistrodesmus, Ammsirodesnms falcatus, Dilsea californica, Gigartina agardhii, Delesseria decipiens, Polyneura latissima, Mastocarpus papillatus, Cryptosiphonia woodii, Porphyra pseudolanceolata, Melobesia mediocris, Boekelovia hooglandii, Codium duthieae, Codium geppiorum, Codium laminarioides, Codium lucasii, Codium spongiosum Plocamium cartilagineum, Farlowia mollis, Hypnea musciformis, Meristotheca senegalensis, Sparlingia pertussa, Meristotheca papulosa, Halydris siliquosa, Rhodymenia pertussa, Botryococcus brmmii, Botryococcus sudeticus, Erythrophyllum delesserioides, Gigartina papillata, Bracteococcus minor, Egregia menziesii, Laminaria sinclairii, Bracteococcus medionucleats, Lessoniopsis littoralis, Carteria, Chaetoceros gracilis, Ectocarpus sp., Valonia macrophysa, Gloiopeltis furcata, Bossiella sp., Constantinea simplex, Colpomenia bullosa, Ahnfeltiopsis linearis, Colpomenia peregrine, Endocladia muricata, Callithamnion pikeanum, Choetoceros muejleri, Calliarthron tuberculosum, Choetoceros mueeri Var. subsalsum, Chlamydomas perigratmlata, Chlorella anitrata, Chlorella antarctica, Chloreuaureoviridis, Chlamydomonas rheinhardii, Neochloris oleoabundans, Emiliana huxleyi, Chlamydomonas sajao, Gigartina exasperate, Chondracanthus exasperates, Chlamydomonas moewusii, Candida, Chlorella capsulate, Nanococcus vulgaris, Pelvetiopsis limitata, Chlorella desiccate, Chlorella ellipsoidea, Postelsia palmaeformis, Chlorelia etmrsonii, Sargassum muticum, Chlorella fusco, Eklonia maxima, Chlorella fusca Var. vacuolate, Ceramium rubrum, Chlorella glucolropha, Leathesia marina, Chlorella infiisionum, Analipus japonicas, Chlorella infimon M Var. actophija, Desmodesmus asymmetricus, Chlorella infustomtm Var. attxenophila, Chlorella kessleri, Chlorella lobaphord, Chlorella luieoviridis, Chlorella luieoviridis Var. aureovmdts, Ralfsia fungiformis, Ceramium codicola, Chlorella hiteavmdis var, hitescens, Chlorella riniata, Chlorella minttssima, Chlorella mutabilis, Chlorella nocturna, Chlorella ovalis, Costaria costata, Desmarestia ligulata, Fucus vesiculosus, Fucus serratus, Chlorella parva, Chlorella pyrenoidosa, Chlorella phoiophila, Chlorella pringsheimii, Chlorella protothecoides, Chlorella protat ecoides Var. acidicola, Chlorella regularis, Prionitis sternbergii, Chlorella regularis Var. minima, Chlorella regularis Var. umbricata, Chlorella reisiglii, Chlorella saecharophila, Chlorella saecharophila Var. ellipsoidea, Chlorella salina, Chlorella simplex, Chlorell sorokmiana, Chlorella sphaerica, Chlorella stigmatophora, Chlorella variellii, Chlorella vulgaris, Codium setchellii, Corallina vancouveriensis, Chlorella vulgaris Fo. tertia, Chlorella vulgaris Var. autotrophica, Chlorella vulgaris Var. viridis, Chlorella vulgaris Var. vulgaris, Chlorella vulgaris Var vulgaris Fo. tertia, Chlorella vulgaris Var. vulgaris Fo. viridis, Chlorella xamhella, Chlorella zofingiensis, Chlorella irebouxioides, Chlorococcum infusiovum, Chlorogoni N, Crypthecodinium cohnii, Cyclotella cryptica, Cyclotejla meneghiniana, Dimaliella hardawil, Dunaliella bioculata, Dimaliella granulate, Dunaliella maritime, Dunaliella minuta, Dimaliella parva, Dunaliella peircei, Dunaliella primolecta, Bossiella plumose, Dunaliella salina, Dimaliella terricoia, Dunaliella tertiolecta, Dunaliella viridis, Dunaliella tertioiecta, Eremosphaera viridis, Euglena gracilis, franceia sp., Fragilari crotonensis, Haematococcus pluvialis, Bockrysis Off. galbana, Hochrysis galbana, Lepocinclis, Micraclinium, Micractinhnn, Monaraphidium Mh T M, Nannochloropsis salina, Navicida accepiata, Navicula biskanterae, Navicula pseudotenelloides, Porphyridium cruentum, Porphyridium parvum, Scenedesmus dimorphus, Navicul pellicidosa, Navicida saprophtla, Odontella aurita, Tschia communis, Nitzschia alexandrine, Nitzschia clostenum, Nitzschia communis, Nitzschia D sipata, Nitzschia frustuhmi, Nitzschia hantzschiana, Nitzschia inconspicua, Nitzschia intermedia, Cladophora columbiana, Nitzschia microcephala, Nitzschia pusilla, Isochrysis galbana, Phaedactylum, Lyngbya majuscule, Aphanizomenonflos, Nitzschia pusilla E iptica, Nitzschia pusilla monoensis, Palmaria mollis, Rhodymenia palmata F. mollis, Nitzschia quadrangular, Oocystis pusilla, Oscillatoria limnetica, Acrosiphonia coalita, Oscillatoria subbrevis, Pamchlorelta kessleri, Pascheria acidophila, Phaeodactyhan tricomutwn, Tolypothrix tenuis, Hapalosiphon fontinalis, Ertilissima, Aulosira fphagus, Phortmdium, Pleurochrysis camerae, Pleurochrysis dentate, Pleurochrysis carterae, Prototheca wickerhamii, Prototheca stagnora, Prototheca ponoricensis, Prototheca moriformis, Prototheca zopfii, Pseudochlorella aquatica, Pyrobotrys, Rhodococcus opaciis, Sarcinoid chrysophyte, Scenedesmus annatus, Scenedesmus obliquus, Scenedesmus quadricauda, Schizochytrmm, Spirulina platensis, Spirulina maxima, Synechocystisf, Tagetes erecta, Tagetes Pat La, Tetraedron, Tetrasehnis suecica, Codium fragile, Thalassiosira weissflogii, Viridiella fridericiana, Palmaria palmate, Alaria esculenta, Saccharina latissima, Saccharina sessilis, Saccharina dentigera, Laminaria saccharina, Porphyra umbilicalis, Alaria marginata, Ulva lactuca, Ulva armoricana, Laminaria digitata, Himanthalia elongata, Ascophyllum nodosum, Laminaria longicruris, Scytosiphon dotyi, Scytosiphon lomentaria, Porphyra yezoensis, Focus vesiculosus, Kappaphycus alvarezii, Betaphycus gracilaria, Gelidium pterocladia, Soranthera ulvoidea, Chondrus crispus, Mastocarpus stellatus, Gracilaria edulis, Lithiothamne, Phaeostrophion irregulare, Enteromorpha intestinalis, Enteromorpha compressa, Psedoanabeana NIVA CYA 3, Nostoc sp. MACC 661, Macrocystis pyrifera, Asparagopsis armata, Mazzaella flaccida Iridaea flaccid, Mazzaella oregona, Iridaea oregona, Iridaea heterocarpa, Mazzaella parksii, Iridaea cornucopiae, Mazzaella splendens, Iridaea cordata, or Marl or derivatives or mixtures thereof. However, those skilled in the art will appreciate that it is possible to utilize any other species known in the art, without departing from the scope of the invention. The algae are commercially manufactured and available through various companies.

According to yet another embodiment, the algae can be Spirulina, Arthrospira, Chlorella, Anabaena, Scenedesmus, Aphanizomenon, Dunaliella, Phymatolithion, Lithothamnium, Ascophyllum or their derivatives, species and mixtures thereof. According to further embodiment, algae can be Spirulina plantensis, Spirulina maxima, Anabaena cylindrica, Scenedesmus obliquus, Ascophyllum nodosum, Phymatolithion calcereum, Lithothamnium calcereum, Aphanizomenon flos-aquae, Dunaliella salina or derivatives, species and mixtures thereof. However, those skilled in the art will appreciate that it is possible to utilize any other species of *Spirulina, Arthrospira, Anabaena, Scenedesmus, Ascophyllum, Aphanizomenon, Dunaliella, Phymatolithion, Lithothamnium* or different algaes known in the art, without departing from the scope of the invention. The algae are commercially manufactured and available through various companies.

According to an embodiment, the algae is present in a concentration range of at least 0.1%. According to another embodiment, the algae is present in the range of at least 1% by weight of the total composition. According to another embodiment, the algae is present in a concentration range of at least 5% by weight of the total composition. According to another embodiment, the algae is present in the range of at least 10% by weight of the total composition. According to further embodiment, the algae is present in the range of at least 20% by weight of the total composition. According to further embodiment, the algae is present in the range of at least 30% by weight of the total composition. According to further embodiment, the algae is present in the range of at least 40% by weight of the total composition. According to further embodiment, the algae is present in the range of at least 50% by weight of the total composition. According to further embodiment, the algae is present in the range of at least 60% by weight of the total composition. According to further embodiment, the algae is present in the range of at least 70% by weight of the total composition. According to yet another embodiment the composition comprises algae in the range of at least 80% by weight of the total composition. According to another embodiment the composition comprises algae in the range of at least 90% by weight of the total composition. According to yet another embodiment the composition comprises at least 95% by weight of the algae.

The invention further relates to an agricultural water disintegrable granular composition which includes at least one pesticidal active ingredient and at least one agrochemically acceptable excipient. The water disintegrable granules including the pesticidal active ingredient are in a size range of 0.1 mm to 6 mm and include particles in a size range of from 0.1 micron to 50 microns.

According to another embodiment, the agricultural water disintegrable granular composition is in a size range of 0.1 mm to 6 mm. According to another embodiment, the agricultural granular composition is in a size range of 0.5 mm to 6 mm. According to another embodiment, the agricultural granular composition has a granule size in the range of 1 mm to 6 mm. According to another embodiment, the agricultural granule size range of 1 mm to 5 mm. According to another embodiment, the agricultural granule size is in the range of 2.5 mm to 5 mm.

According to an embodiment, the granules comprise particles in a size range of 0.1 microns to 100 microns. According to an embodiment, the granules comprise particles in a size range of 0.1 microns to 80 microns. According to an embodiment, the granules comprise particles in a size range of 0.2 microns to 50 microns. According to an embodiment, the granules comprise particles in a size range of 0.2 microns to 50 microns. According to an embodiment, the granules comprise particles in a size range of 0.2 microns to 40 microns. According to an embodiment, the granules comprise particles in a size range of 0.2 microns to 30 microns. According to an embodiment, the granules comprise particles in a size range of 0.2 microns to 20 microns. According to an embodiment, the granules comprise particles in a size range of 0.2 microns to 15 microns. According to an embodiment, the granules comprise particles in a size range of 0.2 microns to 10 microns.

According to another embodiment, the pesticidal active comprises at least one of antifoulants, attractants, insecticides, fungicides, herbicides, nematicides, pheromones, defoliants, acaricides, plant growth regulators, algicides, antifeedants, avicides, bactericides, bird repellents, biopesticides, biocides, chemosterilants, safeners, insect attractants, insect repellents, insect growth regulators, mammal repellents, mating disrupters, desiccants, disinfectants, molluscicides, antimicrobials, miticides, ovicides, fumigants, plant activators, rodenticides, synergists, virucides, repellents, microbial pesticides, plant incorporated protectants or salts, derivatives and mixtures therefor.

According to another embodiment, the pesticidal actives include but are not limited to one or more of abamectin, abamectin-aminomethyl, abscisic acid, ACC, acephate, acetamiprid, acethion, acetochlor, acetofenate, acetophos, acetoprole, acibenzolar, acifluorfen, aclonifen, ACN, acrep, acrinathrin, acrylonitrile, acynonapyr, acypetacs, afidopyropen, afoxolaner, alanap, alanycarb, albendazole, aldicarb, aldicarb sulfone, aldimorph, aldoxycarb, aldrin, allethrin, d-trans-allethrin, allicin, allidochlor, allosamidin, alloxydim, allyl alcohol, allyxycarb, alorac, alpha-bromadiolone, alpha-cypermethrin, alpha-endosulfan, alphamethrin, altretamine, aluminium phosphide, aluminum phosphide, ametoctradin, ametridione, ametryn, ametryne, amibuzin, amicarbazone, amicarthiazol, amidithion, amidochlor, amidoflumet, amidosulfuron, aminocarb, aminocyclopyrachlor, aminopyralid, 4-aminopyridine, aminotriazole, amiprofos-methyl, amiprophos, amiprophos-methyl, amisulbrom, amiton, amitrole, ammonium sulfamate, amobam, amorphous silica gel, amorphous silicon dioxide, ampropylfos, AMS, anabasine, ancymidol, anilazine, anilofos, anisuron, anthraquinone, antu, apholate, aramite, arprocarb, arsenous oxide, asomate, aspirin, asulam, athidathion, atraton, atrazine, aureofungin, avermectin, AVG, aviglycine, azaconazole, azadirachtin, azafenidin, azamethiphos, azidithion, azimsulfuron, azinphos-ethyl, azinphosethyl, azinphos-methyl, azinphosmethyl, aziprotryn, aziprotryne, azithiram, azobenzene, azocyclotin, azothoate, azoxystrobin, bachmedesh, barbanate, barium hexafluorosilicate, barium polysulfide, barium silicofluoride, barthrin, basic copper carbonate, basic copper chloride, basic copper sulfate, BCPC, beflubutamid, benalaxyl, benalaxyl-M, benazolin, bencarbazone, benclothiaz, fenridazon-propyl, bendiocarb, bendioxide, benefin, benfluralin, benfuresate, benodanil, benoxacor, benoxafos, benquinox, bensulfuron, bensulide, bentaluron, bentazon, bentazone, benthiavalicarb, benthiazole, benthiocarb, bentranil, benzadox, benzalkonium chloride, benzamacril, benzamizole, benzamorf, benzene hexachloride, benzfendizone, benzimine, benzipram, benzobicyclon, benzoepin, benzofenap, benzofluor, benzohydroxamic acid, benzomate, benzophosphate, benzothiadiazole, benzovindiflupyr, benzoximate, benzoylprop, benzpyrimoxan, benzthiazuron, benzyladenine, benzyl benzoate, berberine, beta-cyfluthrin, beta-cypermethrin, bethoxazin, BHC, gamma-BHC, bialaphos, bicyclopyrone, bifenox, bifenthrin, kappa-bifenthrin, bifujunzhi, bilanafos, binapacryl, bingqingxiao, bioallethrin, S-bioallethrin, bioethanomethrin, biopermethrin, bioresmethrin, biphenyl, bisazir, bismerthiazol, bi smerthiazol-copper, bisphenylmercury methylenedi(x-naphthalene-y-sulphonate), bispyribac, bistrifluron, bisultap, bitertanol, bithionol, bixafen, blasticidin-S, borax, Bordeaux mixture, boric acid, boscalid, BPCMS, BPPS, brassinolide, brassinolide-ethyl, brevicomin, brodifacoum, brofenprox, brofenvalerate, broflanilide, brofluthrinate, bromacil, bromadiolone, alpha-bromadiolone, bromchlophos, bromethalin, bromethrin, bromfenvinfos, bromoacetamide, bromobonil, bromobutide, bromociclen, bromocyclen, bromo-DDT, bromofenoxim, bromofos, bromomethane, bromophos, bromophos-ethyl, bromopropylate, bromothalonil, bromoxynil, brompyrazon, bromuconazole, bronopol, BRP, BTH, bucarpolate, bufencarb, buminafos, bupirimate, buprofezin, Burgundy mixture, busulfan, butacarb, butachlor, butafenacil, butam, butamifos, butane-fipronil, butathiofos, butenachlor, butene-fipronil, butethrin, buthidazole, buthiobate, buthiuron, butifos, butocarboxim, butonate, butopyronoxyl, butoxycarboxim, butralin, butrizol, butroxydim, buturon, butylamine, butylate, butylchlorophos, butylene-fipronil, cacodylic acid, cadusafos, cafenstrole, calciferol, calcium arsenate, calcium chlorate, calcium cyanamide, calcium cyanide, calcium polysulfide, calvinphos, cambendichlor, camphechlor, camphor, d-camphor, captafol, carbam, carbamorph, carbanolate, carbaril, carbaryl, carbasulam, carbathion, carbendazim, carbendazol, carbetamide, carbofenotion, carbofuran, carbon disulfide, carbon tetrachloride, carbonyl sulfide, carbophenothion, carbophos, carboxazole, carboxide, carboxin, carfentrazone, carpropamid, carvacrol, carvone, CAVP, CDAA, CDEA, CDEC, cellocidin, CEPC, ceralure, cerenox, cevadilla, Cheshunt mixture, chinalphos, chinalphos-methyl, chiral-axyl, chitosan, chlobenthiazone, chlomethoxyfen, chloro-IPC, chloralose, chloramben, chloramine phosphorus, chloramphenicol, chloraniformethan, chloranil, chloranocryl, chlorantraniliprole, chlorazifop, chlorazine, chlorbenside, chlorbenzuron, chlorbicyclen, chlorbromuron, chlorbufam, chlordane, chlordecone, chlordimeform, chlorempenthrin, chloretazate, chlorethephon, chlorethoxyfos, chloreturon, chlorfenac, chlorfenapyr, chlorfenazole, chlorfenethol, chlorfenidim, chlorfenprop, chlorfenson, chlorfensulphide, chlorfenvinphos, chlorfenvinphos-methyl, chlorfluazuron, chlorflurazole, chlorflurecol, chlorfluren, chlorflurenol, chloridazon, chlorimuron, chlorinate, chlormephos, chlormequat, chlormesulone, chlormethoxynil, chlornidine, chlornitrofen, chloroacetic acid, chlorobenzilate, chlorodinitronaphthalenes, chlorofenizon, chloroform, α-chlorohydrin, chloromebuform, chloromethiuron, chloroneb, chlorophacinone, chlorophos, chlorophthalim, chloropicrin, chloropon, chloroprallethrin, chloropropylate, chlorothalonil, chlorotoluron, chloroxifenidim, chloroxuron, chloroxynil, chlorphonium, chlorphoxim, chlorphthalim, chlorprazophos, chlorprocarb, chlorpropham, chlorpyrifos, chlorpyrifos-methyl, chlorquinox, chlorsulfuron, chlorthal, chlorthiamid, chlorthiophos, chlortoluron, chlozolinate, chltosan, cholecalciferol, choline chloride, chromafenozide, cicloheximide, cimectacarb, cimetacarb, cinerin I, cinerin II, cinerins, cinmethylin, cinosulfuron, cintofen, ciobutide, cisanilide, cismethrin, clacyfos, clefoxydim, clenpirin, clenpyrin, clethodim, climbazole, cliodinate, cloethocarb, clofencet, clofenotane, clofenvinfos, clofibric acid, clofop, clomazone, clomeprop, clonitralid, cloprop, cloproxydim, clopyralid, cloquintocet, cloransulam, closantel, clothianidin, clotrimazole, cloxyfonac, cloxylacon, clozylacon, CMA, CMMP, CMP, CMU, codlelure, colecalciferol, colophonate, copper acetate, copper acetoarsenite, copper arsenate, copper carbonate, basic, copper hydroxide, copper naphthenate, copper oleate, copper oxychloride, copper 8-quinolinolate, copper silicate, copper sulfate, copper sulfate, basic, copper zinc chromate, coumachlor, coumafene, coumafos, coumafuryl, coumaphos, coumatetralyl, coumethoxystrobin, coumithoate, coumoxystrobin, 4-CPA, 4-CPB, CPMC, CPMF, 4-CPP, CPPC, credazine, cresol, cresylic acid, crimidine, crotamiton, crotoxyfos, crotoxyphos, crufomate, cryolite, cue-lure, cufraneb, cumyleron, cumyluron, cuprobam, cuprous oxide, curcumenol, CVMP, cyanamide, cyanatryn, cyanazine, cyanofenphos, cyanogen, cyanophos, cyanthoate, cyan-traniliprole, cyanuric acid, cyazofamid, cybutryne, cyclafuramid, cyclanilide, cyclaniliprole, cyclethrin, cycloate, cycloheximide, cycloprate, cycloprothrin, cyclopyrimorate, cyclosulfamuron, cycloxydim, cycluron, cyenopyrafen, cyflufenamid, cyfluthrin, beta-cyfluthrin, cyhalodiamide, cyhalofop, cyhalothrin, gamma-cyhalothrin, lambda-cyhalothrin, cyhexatin, cymiazole, cyometrinil, cypendazole, cypermethrin, alpha-cypermethrin, beta-cypermethrin, theta-cypermethrin, zeta-cypermethrin, cyperquat, cyphenothrin, cyprazine, cyprazole, cyproconazole, cyprodinil, cyprofuram, cypromid, cyprosulfamide, cyromazine, cythioate, cytrex, 1,3-D, 2,4-D, 3,4-DA, daimuron, dalapon, daminozide, dayoutong, 2,4-DB, 3,4-DB, DBCP, d-camphor, DCB, DCIP, DCPA (USA), DCPA (Japan), DCPTA, DCU, DDD, DDPP, DDT, pp'-DDT, DDVP, 2,4-DEB, debacarb, decafentin, decamethrin, decarbofuran, deet, dehydroacetic acid, deiquat, delachlor, delnav, deltamethrin, demephion, demephion-O, demephion-S, demeton, demeton-methyl, demeton-O, demeton-O-methyl, demeton-S, demeton-S-methyl, demeton-S-methylsulphon, demeton-S-methyl sulphone, DEP, 2,4-DEP, depalléthrine, derris, 2,4-DES, desmedipham, desmetryn, desmetryne, d-fanshiluquebingjuzhi, diafenthiuron, dialifor, dialifos, di-allate, diallate, diamidafos, dianat, diatomaceous earth, diatomite, diazinon, dibrom, 1,2-dibromoethane, dibutyl phthalate, dibutyl succinate, dicamba, dicapthon, dichlobenil, dichlobentiazox, dichlofenthion, dichlofluanid, dichlone, dichloralurea, dichlorbenzuron, dichlorfenidim, dichlorflurecol, dichlorflurenol, dichlormate, dichlormid, o-dichlorobenzene, ortho-dichlorobenzene, p-dichlorobenzene, para-di chlorobenzene, 1,2-dichloroethane, dichloromethane, dichlorophen, 3,6-dichloropicolinic acid, 1,2-dichloropropane, 1,3-dichloropropene, dichlorprop, dichlorprop-P, dichlozolin, dichlozoline, diclobutrazol, diclocymet, diclofop, diclomezine, dicloran, dicloromezotiaz, diclosulam, dicofol, dicophane, dicou-marol, dicresyl, dicrotophos, dicryl, dicumarol, dicyclanil, dicyclonon, dieldrin, dienochlor, dietham-quat, diethatyl, diethion, diethion, diethofencarb, diethiolate, diethon, diethyl pyrocarbonate, di-ethyltoluamide, difenacoum, difenoconazole, difenopenten, difenoxuron, difenzoquat, difethialone, diflovidazin, diflubenzuron, diflufenican, diflufenicanil, diflufenzopyr, diflumetorim, dikegulac, dilor, dimatif, dimefluthrin, dimefox, dimefuron, dimehypo, dimepiperate, dimetachlone, dimetan, dimethacarb, dimethachlone, dimethachlor, dimethametryn, dimethenamid, dimethenamid-P, dimethipin, dimethirimol, dimethoate, dimethomorph, dimethrin, dimethyl carbate, dimethyl disulfide, dimethyl phthalate, dimethylvinphos, dimetilan, dimexano, dimidazon, dimoxystrobin, dimpylate, dimuron, dinex, diniconazole, diniconazole-M, R-diniconazole, dinitramine, dinitrophenols, dinobuton, dinocap, dinocap-4, dinocap-6, dinocton, dinofenate, dinopenton, dinoprop, dinosam, dinoseb, dinosulfon, dinotefuran, dinoterb, dinoterbon, diofenolan, dioxabenzofos, dioxacarb, dioxathion, dioxation, diphacin, diphacinone, diphenadione, diphenamid, diphenamide, diphenylamine, diphenyl sulfone, diphenylsulphide, diprogulic acid, dipropalin, dipropetryn, dipterex, dipymetitrone, dipyrithione, diquat, disosultap, disparlure, disugran, disul, disulfiram, disulfoton, ditalimfos, dithicrofos, dithioether, dithiometon, dithiopyr, diuron, dixanthogen, d-limonene, DMDS, DMPA, DNOC, dodemorph, dodicin, dodine, dofenapyn, doguadine, dominicalure, doramectin, 2,4-DP, 3,4-DP, DPC, drazoxolon, DSMA, d-trans-allethrin, d-trans-resmethrin, dufulin, dymron, EBEP, EBP, ebufos, α-ecdysone, β-ecdysone, ecdysterone, echlomezol, EDB, EDC, EDDP, edifenphos, eglinazine, emamectin, EMPC, empenthrin, enadenine, endosulfan, alpha-endosulfan, endothal, endothall, endothion, endrin, enestroburin, enilconazole, enoxastrobin, ephirsulfonate, EPN, epocholeone, epofenonane, epoxiconazole, eprinomectin, epronaz, epsilon-metofluthrin, epsilon-momfluorothrin, EPTC, erbon, ergocalciferol, erlujixiancaoan, esdépalléthrine, esfenvalerate, ESP, esprocarb, etacelasil, etaconazole, etaphos, etem, ethaboxam, ethachlor, ethalfluralin, ethametsulfuron, ethaprochlor, ethidimuron, ethiofencarb, ethiolate, ethion, ethiozin, ethiprole, ethirimol, ethoate-methyl, ethobenzanid, ethofumesate, ethohexadiol, ethoprop, ethoprophos, ethoxyfen, (3-ethoxypropyl)mercury bromide, ethoxyquin, ethoxysulfuron, ethychlozate, ethylan, ethyl-DDD, ethylene, ethylene dibromide, ethylene dichloride, ethylene oxide, ethyl formate, ethylicin, ethylmercury acetate, ethylmercury bromide, ethylmercury chloride, ethylmercury 2,3-dihydroxypropyl mercaptide, ethylmercury phosphate, N-(ethylmercury)-p-toluenesulfonanilide, N-(ethylmercury)-p-toluenesulphonanilide, ethyl pyrophosphate, etinofen, ETM, etnipromid, etobenzanid, etofenprox, etoxazole, etridiazole, etrimfos, étrimphos, eugenol, EXD, famphur, fenac, fenamidone, fenaminosulf, fenaminstrobin, fenamiphos, fenapanil, fenarimol, fenasulam, fenazaflor, fenazaquin, fenbuconazole, fenbutatin oxide, fenchlorazole, fenchlorphos, fenclofos, fenclorim, fenethacarb, fenfluthrin, fenfuram, fenhexamid, fenidin, fenitropan, fenitrothion, fenizon, fenjuntong, fenobucarb, fenolovo, fenoprop, fenothiocarb, fenoxacrim, fenoxanil, fenoxaprop, fenoxaprop-P, fenoxasulfone, fenoxycarb, fenpiclonil, fenpicoxamid, fenpirithrin, fenpropathrin, fenpropidin, fenpropimorph, fenpyrazamine, fenpyroximate, fenquinotrione, fenridazon, fenson, fensulfothion, fenteracol, fenthiaprop, fenthion, fenthion-ethyl, fentiaprop, fentin, fentrazamide, fentrifanil, fenuron, fenuron-TCA, fenvalerate, ferimzone, ferric phosphate, ferrous sulfate, fipronil, flamprop, flamprop-M, flazasulfuron, flocoumafen, flometoquin, flonicamid, florasulam, florpyrauxifen, fluacrypyrim, fluazaindolizine, fluazifop, fluazifop-P, fluazolate, fluazuron, flubendiamide, flubenzimine, flubrocythrinate, flucarbazone, flucetosulfuron, fluchloralin, flucofuron, flucycloxuron, flucythrinate, fludioxonil, fluenethyl, fluenetil, fluensulfone, flufenacet, flufenerim, flufenican, flufenoxuron, flufenoxystrobin, flufenprox, flufenpyr, flufenzine, flufiprole, fluhexafon, fluindapyr, flumethrin, flumetover, flumetralin, flumetsulam, flumezin, flumipropyn, flumorph, fluometuron, fluopicolide, fluopyram, fluorbenside, fluoridamid, fluoroacetamide, fluoroacetic acid, fluorochloridone, fluorodifen, fluoroglycofen, fluoroimide, fluoromide, fluoromidine, fluoronitrofen, fluoroxypyr, fluothiuron, fluotrimazole, fluoxastrobin, flupoxam, flupropacil, flupropadine, flupropanate, flupyradifurone, flupyrsulfuron, fluquinconazole, fluralaner, flurazole, flurecol, flurenol, fluridone, flurochloridone, fluromidine, fluroxypyr, flurprimidol, flursulamid, flurtamone, flusilazole, flusulfamide, flutenzine, fluthiacet, fluthiamide, flutianil, flutolanil, flutriafol, fluvalinate, tau-fluvalinate, fluxametamide, fluxapyroxad, fluxofenim, folpel, fomesafen, fonofos, foramsulfuron, forchlorfenuron, formaldehyde, formparanate, fosamine, fosetyl, fosmethilan, fospirate, fosthiazate, fosthietan, frontalin, fthalide, fuberidazole, fucaojing, fucaomi, ethoxyfen-ethyl, fumarin, funaihecaoling, fuphenthiourea, furalane, furalaxyl, furamethrin, furametpyr, furan tebufenozide, furathiocarb, furcarbanil, furconazole, furconazole-cis, furethrin, furfural, furilazole, furmecyclox, furophanate, furyloxyfen, gamma-BHC, gamma-cyhalothrin, gamma-HCH, genit, gibberellic acid, gibberellin A3, gibberellins, gliftor, glitor, glucochloralose, glufosinate, glufosinate-P, glyodin, glyoxime, glyphosate, glyphosine, gossyplure, grandlure, griseofulvin, guanoctine, guazatine, halacrinate, halauxifen, halfenprox, halofenozide, halosafen, halosulfuron, haloxydine, HCA, HCB, HCH, gamma-HCH, hemel, hempa, HEOD, heptafluthrin, heptenophos, heptopargil, herbimycin, herbimycin A, heterophos, hexachlor, hexachloran, hexachloroacetone, hexachlorobenzene, hexachlorobutadiene, hexachlorophene, hexaconazole, hexaflumuron, hexafluoramin, hexafurate, hexalure, hexamide, hexazinone, hexylthiofos, hexythiazox, HHDN, holosulf, homobrassinolide, huanjunzuo, hydramethylnon, hydrargaphen, hydrated lime, hydrogen cyanamide, hydrogen cyanide, hydroprene, S-hydroprene, hydroxyisoxazole, 4-hydroxyphenethyl alcohol, 8-hydroxyquinoline sulfate, hymexazol, hyquincarb, IAA, IBA, IBP, icaridin, imazalil, imazamethabenz, imazamox, imazapic, imazapyr, imazaquin, imazethapyr, imazosulfuron, imibenconazole, imicyafos, imidacloprid, imidaclothiz, iminoctadine, imiprothrin, inabenfide, indanofan, indaziflam, indoxacarb, inezin, infusorial earth, iodobonil, iodocarb, iodofenphos, iodomethane, iodosulfuron, iofensulfuron, ioxynil, ipazine, IPBC, IPC, ipconazole, ipfencarbazone, ipfentrifluconazole, iprobenfos, iprovalicarb, iprymidam, ipsdienol, ipsenol, IPSP, IPX, isamidofos, isazofos, isobenzan, isocarbamid, isocarbamide, isocarbophos, isocil, isodrin, isofenphos, isofenphos-methyl, isofetamid, isoflucypram, isolan, isomethiozin, isonoruron, isopamphos, isopolinate, isoprocarb, isoprocil, isopropalin, isopropazol, isoprothiolane, isoproturon, isopyrazam, isopyrimol, isothioate, isotianil, isouron, isovaledione, isoxaben, isoxachlortole, isoxadifen, isoxapyrifop, isoxathion, isuron, ivermectin, ixoxaben, izopamfos, izopamphos, japonilure, japothrins, jasmolin I, jasmolin II, jasmonic acid, jiahuangchongzong, coumethoxystrobin, jiecaowan, jiecaoxi, Jinganmycin A, jodfenphos, juvenile hormone I, juvenile hormone II, juvenile hormone III, kadethrin, kappa-bifenthrin, kappa-tefluthrin, karbutilate, karetazan, kasugamycin, kejunlin, kelevan, ketospiradox, kieselguhr, kinetin, kinoprene, S-kinoprene, kiralaxyl, kresoxim-methyl, kuicaoxi, lactofen, lambda-cyhalothrin, lancotrione, latilure, lead arsenate, lenacil, lepimectin, leptophos, lime sulfur, d-limonene, lindane, lineatin, linuron, lirimfos, litlure, looplure, lufenuron, clacyfos, lvfumijvzhi, lythidathion, M-74, M-81, MAA, magnesium phosphide, malathion, maldison, maleic hydrazide, malonoben, MAMA, mancopper, mancozeb, mandestrobin, mandipropamid, matrine, mazidox, MCC, MCP, 1-MCP, MCPA, 2,4-MCPA, MCPA-thioethyl, MCPB, 2,4-MCPB, MCPP, mebenil, mecarbam, mecarbinzid, mecarphon, mecoprop, mecoprop-P, medimeform, medinoterb, medlure, mefenacet, mefenoxam, mefenpyr, mefentrifluconazole, mefluidide, megatomoic acid, melissyl alcohol, melitoxin, MEMC, menazon, MEP, mepanipyrim, meperfluthrin, mephenate, mephosfolan, mepiquat, mepronil, meptyldinocap, mercaptodimethur, mercaptophos, mercaptophos thiol, mercaptothion, mercuric chloride, mercuric oxide, mercurous chloride, merphos, merphos oxide, mesoprazine, mesosulfuron, mesotrione, mesulfen, mesulfenfos, mesulphen, metacresol, metaflumizone, metalaxyl, metalaxyl-M, R-metalaxyl, metaldehyde, metam, metamifop, metamitron, metaphos, metaxon, metazachlor, metazosulfuron, metazoxolon, metcamifen, metconazole, metepa, metflurazon, methabenzthiazuron, methacrifos, methalpropalin, metham, methasulfocarb, methazole, methfuroxam, methibenzuron, methidathion, methiobencarb, methiocarb, methiopyrisulfuron, methiotepa, methiozolin, methiuron, methocrotophos, metholcarb, methometon, methomyl, methoprene, S-methoprene, methoprotryn, methoprotryne, methoquin-butyl, methothrin, methoxychlor, 2-methoxyethylmercury chloride, methoxyfenozide, methoxyphenone, methyl apholate, methyl bromide, methyl eugenol, methyl iodide, methyl-isofenphos, methyl isothiocyanate, methyl parathion, methylacetophos, methylchloroform, 1-methylcyclopropene, methyldithiocarbamic acid, methyldymron, methylene chloride, methylmer-captophos, methylmercaptophos oxide, methylmercaptophos thiol, methylmercury benzoate, methylmercury dicyandiamide, methylmercury pentachlorophenoxide, methylneodecanamide, methylnitrophos, methyltriazothion, metiozolin, metiram-zinc, metobenzuron, metobromuron, metofluthrin, epsilon-metofluthrin, metolachlor, S-metolachlor, metolcarb, metometuron, metominostrobin, metosulam, metoxadiazone, metoxuron, metrafenone, metriam, metribuzin, metrifonate, metriphonate, metsulfovax, metsulfuron, mevinphos, XMC, mieshuan, milbemectin, milbemycin oxime, milneb, mimanan, mipafox, MIPC, mirex, MNAF, moguchun, molinate, molosultap, monalide, monalide, momfluorothrin, epsilon-momfluorothrin, monisuron, monoamitraz, monochloroacetic acid, monocrotophos, monolinuron, monomehypo, monosulfiram, monosulfuron, monosultap, monuron, monuron-TCA, morfamquat, moroxydine, morphothion, morzid, moxidectin, MPMC, MSMA, MTMC, α-multistriatin, muscalure, myclobutanil, myclozolin, myricyl alcohol, NAA, NAAm, nabam, naftalofos, naphthalene, naphthaleneacetamide, α-naphthaleneacetic acids, naphthalic anhydride, naphthalophos, 1-naphthol, naphthoxyacetic acids, naphthylacetic acids, naphthylindane-1,3-diones, naphthyloxyacetic acids, naproanilide, napropamide, napropamide-M, natamycin, NBPOS, neburea, neburon, nendrin, neonicotine, nichlorfos, niclofen, niclosamide, nicobifen, nicosulfuron, nicotine, nicotine sulfate, nifluridide, nikkomycins, NIP, nipyraclofen, nipyralofen, nitenpyram, nithiazine, nitralin, nitrapyrin, nitrilacarb, nitrofen, nitrofluorfen, nitrostyrene, nitrothal-isopropyl, nobormide, nonanol, norbormide, norea, nor-flurazon, nornicotine, noruron, novaluron, noviflumuron, NPA, nuarimol, nuranone, OCH, octa-chlorodipropyl ether, octhilinone, 2-(octylthio)ethanol, o-dichlorobenzene, ofurace, omethoate, o-phenylphenol, orbencarb, orfralure, orthobencarb, ortho-dichlorobenzene, orthosulfamuron, oryctalure, orysastrobin, oryzalin, osthol, osthole, ostramone, ovatron, ovex, oxabetrinil, oxadiargyl, oxadiazon, oxadixyl, oxamate, oxamyl, oxapyrazon, oxapyrazone, oxasulfuron, oxathiapiprolin, oxaziclomefone, oxine-copper, oxine-Cu, oxolinic acid, oxpoconazole, oxycarboxin, oxydemeton-methyl, oxydeprofos, oxydisulfoton, oxyenadenine, oxyfluorfen, oxymatrine, oxytetracycline, oxythioquinox, PAC, paclobutrazol, paichongding, pallethrine, PAP, para-dichlorobenzene, parafluron, paraquat, parathion, parathion-methyl, parinol, Paris green, PCNB, PCP, PCP-Na, p-dichlorobenzene, PDJ, pebulate, pédinex, pefurazoate, pelargonic acid, penconazole, pencycuron, pendimethalin, penfenate, penflufen, penfluron, penoxalin, penoxsulam, pentachlorophenol, pentachlorophenyl laurate, pentanochlor, penthiopyrad, pentmethrin, pentoxazone, perchlordecone, perfluidone, permethrin, pethoxamid, PHC, phenamacril, phenamacril-ethyl, phenaminosulf, phenazine oxide, phenisopham, phenkapton, phenmedipham-ethyl, phenobenzuron, phenothiol, phenothrin, phenproxide, phenthoate, 8-phenylmercurioxyquinoline, phenylmercuriurea, phenylmercury acetate, phenylmercury chloride, phenylmercury derivative of pyrocatechol, phenylmercury nitrate, phenylmercury salicylate, 2-phenylphenol, phosacetim, phosalone, phosametine, phosazetim, phosazetin, phoscyclotin, phosdiphen, phosethyl, phosfolan, phosfolan-methyl, phos-glycin, phosnichlor, phosphamide, phosphamidon, phosphine, phosphinothricin, phosphocarb, phosphorus, phostin, phoxim, phoxim-methyl, phthalide, phthalophos, phthalthrin, picarbutrazox, picaridin, picloram, picolinafen, picoxystrobin, pimaricin, pindone, piperalin, piperazine, piperonyl butoxide, piperonyl cyclonene, piperophos, piproctanly, piproctanyl, piprotal, pirimetaphos, pirimicarb, piriminil, pirimioxyphos, pirimiphos-ethyl, pirimiphos-methyl, pival, pivaldione, plifenate, PMA, PMP, polybutenes, polycarbamate, polychlorcamphene, polyethoxyquinoline, polyoxin D, polyoxins, polyoxorim, polythialan, potassium arsenite, potassium azide, potassium cyanate, potassium ethylxanthate, potassium naphthenate, potassium polysulfide, potassium thiocyanate, pp'-DDT, prallethrin, precocene I, precocene II, precocene III, pretilachlor, primidophos, primisulfuron, probenazole, prochloraz, proclonol, procyazine, procymidone, prodiamine, profenofos, profluazol, profluralin, profluthrin, profoxydim, profurite-aminium, proglinazine, prohexadione, prohydrojasmon, promacyl, promecarb, prometon, prometryn, prometryne, promurit, pronamide, propachlor, propafos, propamidine, propamocarb, propanil, propaphos, propaquizafop, propargite, proparthrin, propazine, propetamphos, propham, propiconazole, propidine, propisochlor, propoxur, propoxycarbazone, propyl isome, propyrisulfuron, propyzamide, proquinazid, prosuler, prosulfalin, prosulfocarb, prosulfuron, prothidathion, prothiocarb, prothioconazole, prothiofos, prothoate, protrifenbute, proxan, prymidophos, prynachlor, psoralen, psoralene, pydanon, pydiflumetofen, pyflubumide, pymetrozine, pyracarbolid, pyraclofos, pyraclonil, pyraclostrobin, pyraflufen, pyrafluprole, pyramat, pyrametostrobin, pyraoxystrobin, pyrasulfotole, pyraziflumid, pyrazolate, pyrazolynate, pyrazon, pyrazophos, pyrazosulfuron, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridaphenthione, pyridinitril, pyrifenox, pyrifluquinazon, pyriftalid, pyrimetaphos, pyrimethanil, pyrimicarbe, pyrimidifen, pyriminobac, pyriminostrobin, pyrimiphos-éthyl, pyrimiphos-methyl, pyrimisulfan, pyrimitate, pyrinuron, pyriofenone, pyriprole, pyripropanol, pyriproxyfen, pyrisoxazole, pyrithiobac, pyrolan, pyroquilon, pyroxasulfone, pyroxsulam, pyroxychlor, saijunmao, quassia, quinacetol, quinalphos, quinalphos-methyl, quinazamid, quinclorac, quinconazole, quinmerac, quinoclamine, quinofumelin, quinomethionate, quinonamid, quinothion, quinoxyfen, quintiofos, quintozene, quizalofop-P, quwenzhi, quyingding, rabenzazole, rafoxanide, R-diniconazole, rebemide, reglone, renofluthrin, renriduron, rescalure, resmethrin, d-trans-resmethrin, rhodethanil, rhodojaponin-III, ribavirin, rimsulfuron, rizazole, R-metalaxyl, rodethanil, ronnel, rotenone, ryania, sabadilla, saflufenacil, saijunmao, copper salt of bismerthiazol, salicylanilide, salifluofen, sanguinarine, santonin, sarolaner, S-bioallethrin, schradan, scilliroside, sebuthylazine, secbumeton, sedaxane, selamectin, semiamitraz, sesamex, sesamolin, sesone, sethoxydim, sevin, S-hydroprene, shuangjiaancaolin, siduron, siglure, silafluofen, silatrane, silica aerogel, silica gel, silthiofam, silthiopham, silthiophan, silvex, simazine, simeconazole, simeton, simetryn, simetryne, sintofen, S-kinoprene, slaked lime. SMA, S-methoprene, S-metolachlor, sodium arsenite, sodium azide, sodium chlorate, sodium cyanide, sodium fluoride, sodium fluoroacetate, sodium hexafluorosilicate, sodium naphthenate, sodium orthophenylphenoxide, sodium pentachlorophenate, sodium pentachlorophenoxide, sodium o-phenylphenoxide, sodium polysulfide, sodium silicofluoride, disodium tetraborate, sodium tetrathiocarbonate, sodium thiocyanate, solan, sophamide, spinetoram, spinosad, spirodiclofen, spiromesifen, spirotetramat, spiroxamine, stirofos, streptomycin, strychnine, sulcatol, sulcofuron, sulcotrione, sulfallate, sulfentrazone, sulfiram, sulfluramid, sulfodiazole, sulfometuron, sulfosate, sulfosulfuron, sulfotep, sulfotepp, sulfoxaflor, sulfoxide, sulfoxime, sulfur, sulfuric acid, sulglycapin, sulphosate, sulprofos, sultropen, swep, 2,4,5-T, tau-fluvalinate, tavron, tazimcarb, 2,4,5-TB, 2,3,6-TBA, TBTO, TBZ, TCA, TCBA, TCMTB, TCNB, TDE, tebuconazole, tebufenozide, tebufenpyrad, tebufloquin, tebupirimfos, tebutam, tebuthiuron, tecloftalam, tecnazene, tecoram, tedion, teflubenzuron, tefluthrin, kappa-tefluthrin, tefuryltrione, tembotrione, temefos, temephos, tepa, TEPP, tepraloxydim, teproloxydim, terallethrin, terbacil, terbucarb, terbuchlor, terbufos, terbumeton, terbuthylazine, terbutol, terbutryn, terbutryne, terraclor, terramicin, terramycin, tetcyclacis, tetrachloroethane, tetrachlorvinphos, tetraconazole, tetradifon, tetradisul, tetrafluron, tetramethrin, tetramethylfluthrin, tetramine, tetranactin, tetraniliprole, tetrapion, tetrasul, thallium sulfate, thallous sulfate, thenylchlor, theta-cypermethrin, thiabendazole, thiacloprid, thiadiazine, thiadifluor, thiamethoxam, thiameturon, thiapronil, thiazafluron, thiazfluron, thiazone, thiazopyr, thicrofos, thicyofen, thidiazimin, thidiazuron, thiencarbazone, thifensulfuron, thifluzamide, thimerosal, thimet, thiobencarb, thiocarboxime, thiochlorfenphim, thiochlorphenphime, thiocyanatodinitrobenzenes, thiodan, thiodiazole-copper, thiodicarb, thiofanocarb, thiofanox, thiofluoximate, thiohempa, thiomersal, thiometon, thionazin, thiophanate, thiophanate-ethyl, thiophanate-methyl, thiophos, thioquinox, thiosemicarbazide, thiosultap, thiotepa, thioxamyl, thiuram, thuringiensin, tiabendazole, tiadinil, tiafenacil, tiaojiean, TIBA, tifatol, tiocarbazil, tioclorim, tioxazafen, tioxymid, TMTD, tirpate, tolclofos-methyl, tolfenpyrad, tolprocarb, tolpyralate, tolylfluanid, tolylmercury acetate, tomarin, topramezone, toxaphene, 2,4,5-TP, 2,3,3-TPA, TPN, tralkoxydim, tralocythrin, tralomethrin, tralopyril, d-trans-allethrin, d-trans-resmethrin, transpermethrin, tretamine, tri-allate, triacontanol, triadimefon, triadimenol, triafamone, triallate, triamiphos, triapenthenol, triarathene, triarimol, triasulfuron, triazbutil, triaziflam, triazophos, triazothion, triazoxide, tribasic copper chloride, tribasic copper sulfate, tribenuron, tribufos, tributyltin oxide, tricamba, trichlamide, trichlopyr, trichlormetaphos-3, trichloronat, trichloronate, trichlorotrinitrobenzenes, trichlorphon, triclopyr, triclopyricarb, tricresol, tricyclazole, tricyclohexyltin hydroxide, tridemorph, tridiphane, trietazine, trifenmorph, trifenofos, trifloxystrobin, trifloxysulfuron, trifludimoxazin, triflumezopyrim, triflumizole, triflumuron, trifluralin, triflusulfuron, trifop, trifopsime, trihydroxytriazine, 2,3,5-tri-iodobenzoic acid, 2,3,5-triiodobenzoic acid, trimedlure, trimethacarb, trimeturon, trinexapac, triphenyltin, triprene, tripropindan, triptolide, tritac, trithialan, triticonazole, tritosulfuron, trunc-call, tuoyelin, uniconazole, uniconazole-P, urbacide, uredepa, valerate, validamycin, validamycin A, valifenalate, valone, vamidothion, vangard, vaniliprole, vernolate, vitamin D3, warfarin, xiaochongliulin, xinjunan, fenaminstrobin, XMC, xylachlor, xylenols, xylylcarb, xymiazole, yishijing, zarilamid, zeatin, zengxiaoan, zeta-cypermethrin, zinc naphthenate, zinc phosphide, zinc thiazole, zinc thiozole, zinc trichlorophenate, zinc trichlorophenoxide, zineb, zolaprofos, zoocoumarin, zoxamide, pyrametostrobin, zuomihuanglong, 1-MCP, 1-methylcyclopropene, 1-naphthol, 1,2-dichloropropane, 1,3-D, 1,3-dichloropropene, 2iP, 2-methoxyethylmercury chloride, 2-(octylthio)ethanol, 2-phenylphenol, 2,3,3-TPA, 2,3,5-triiodobenzoic acid, 2,3,6-TBA, 2,4-D, 2,4-DB, 2,4-DEB, 2,4-DEP, 2,4-DES, 2,4-DP, 2,4-MCPA, 2,4-MCPB, 2,4,5-T, 2,4,5-TB, 2,4,5-TP, (3-ethoxypropyl)mercury bromide, 3,4-DA, 3,4-DB, 3,4-DP, 3,6-dichloropicolinic acid, 4-aminopyridine, 4-CPA, 4-CPB, 4-CPP, 4-hydroxyphenethyl alcohol, 8-hydroxyquinoline sulfate, 8-phenylmercurioxyquinoline, or salts, derivatives and mixtures therefore. However, the above lists of pesticides are exemplary and not meant to limit the scope of the invention. Those skilled in the art will appreciate that it is possible to use other pesticidal actives without departing from the scope of the present invention.

According to an embodiment, the water disintegrable granular composition, comprises microcapsules, wherein the microcapsules comprise the pesticidal active ingredient. Thus, according to an embodiment, the pesticidal active can be encapsulated within a polymeric shell wall. According to an embodiment, the polymeric shell wall is a polyurea shell wall.

According to another embodiment, the water disintegrable granular composition comprising the water insoluble nutrient or algae or the pesticidal active ingredient of the invention exhibits a reduced bulk density compared to known granules, which facilitates faster disintegration of the granules and also prevents settling of the composition in water. Bulk density of the water disintegrable granules of the invention can be defined as the mass of many particles comprised in the granules divided by the total volume they occupy.

According to an embodiment, the bulk density of the water disintegrable granules comprising the water insoluble material or algae or the pesticidal active, is less than 1.5 gms/ml. According to an embodiment, the water disintegrable granules have a bulk density of less than 1.4 g/ml. According to another embodiment, the water distintegrable granules have a bulk density of less than 1.3 g/ml. According to an embodiment the bulk density of the water disintegrable granules is preferably less than 1.2 gms/ml. The bulk density of the granules are measured by standard methods such as the CIPAC handbook test, MT 186.

According to another embodiment, the water disintegrable granular composition of the invention exhibits an improved true density compared to known granules. True Density is the density of the granules itself and is defined as the weight of the granules divided by the true volume of the granules. According to an embodiment, the water disintegrable granular composition has a true density of less than 2.5 g/ml. According to another embodiment, the water disintegrable granular composition has a true density of less than 2.4 g/ml. The true density of the granules are measured by a method as described below:

Apparatus Required:

Le chatelier Flask—250 mL capacity with marking 0-1 mL below bulb and 18-24 mL above the bulb.

Kerosene or n-Hexane

Procedure:

1.1 Fill the Le chatelier Flask with kerosene or n-Hexane in between 0-1 ml marking and allow to equilibrate at room temperature in Water bath. Note down the exact constant volume while flask is in water bath (V1).

1.2 Wipe out and clean the flask from outside, place it on weighing balance and tare it along with stopper.

1.3 Pour gently sample in the flask from top untill solvent reaches in between 20-24 mL markings. Note down the sample weight which was added (to the nearest 0.01 g) (W).

1.4 Again put the flask on water bath at room temperature and wait until constant reading for the volume observed. Note down the exact constant volume while flask in water bath (V2).

1.5 Calculate the true densities (g/ml).

1.6 CALCULATION:

$$\text{True density } TD = \frac{W}{V2-V1} \text{g/mL}$$

Figure 2:
Figure 3:
Figure 4:

Attrition resistance determines the resistance of a granular material to wear. The water disintegrable granular composition has good attrition resistance. The Samples can be tested for attrition as per the CIPAC Handbook specified test, "MT 178—Attrition resistance of granules". To carry out the test, prior to the test, the granule is sieved on a 125 im sieve in order to remove fine particles. A known amount of this dust-free granule is transferred to a glass bottle and is then subjected to a rolling movement with an equal amount of glass beads. After rolling for a specified period, the attrition resistance is determined by sieving again on a 125 im sieve and weighing the material retained on the sieve. According to another embodiment, the water disintegrable granular composition of the invention comprising the water insoluble material or algae or the pesticidal active exhibits an improved attrition resistance compared to known granules. It can be seen from FIG. 2 showing Sulphur water dispersible granules as per the teachings of WO2008084495, post packaging and transportation and FIG. 4 which is an image of the water dispersible granular composition (410) of Sulfur 70%+Zinc oxide 15% as per the teachings of WO2012131702, that the granules crumble to very fine particle size pursuant to manufacturing, processing, packaging or transportation leading to loss of release control, and nutrient leaching with these water dispersible granular forms as compared to the water disintegrable granular compositions of the invention. According to an embodiment, the attrition resistance of the water disintegrable granular composition is at least 50%. According to an embodiment, the attrition resistance of the water disintegrable granular composition is at least 60%. According to an embodiment, the attrition resistance exhibited by the water disintegrable granular composition is at least 70%. According to an embodiment, the attrition resistance of the water disintegrable granular composition is at least 80%. According to an embodiment, the attrition resistance of the granules is at least 90%. According to another embodiment, the water disintegrable granular composition exhibits an attrition resistance of at least 95%. According to an embodiment, the water disintegrable granular composition exhibits an attrition resistance at least 98%. According to an embodiment, the water disintegrable granular composition exhibits an attrition resistance at least 99%. The attrition resistance of the granules can be determined using a standard CIPAC test.

The agricultural water disintegrable granular composition comprising the water insoluble nutrient or the algae or the pesticidal active ingredient surprisingly possesses good hardness. The hardness would depend on other materials also used in conjunction with the water insoluble nutrient or the algae or the pesticidal active ingredient. For example, the hardness of the granules is on the lower side or less than 5N, when organic matter or materials such as humic acid or fulvic acid are also present within the composition. According to an embodiment, the hardness exhibited by the granules is at least 1 Newton. According to an embodiment, the hardness of the water disintegrable granular composition is at least 3 Newton. According to an embodiment, the hardness of the water disintegrable granular composition is at least 5 Newton. According to an embodiment, the hardness of the granules is at least 10 Newton. According to an embodiment, the hardness of the water disintegrable granular composition is at least 15 Newton. According to an embodiment, the hardness exhibited by the granules is at least 20 Newton. According to an embodiment, the hardness of the granules is at least 30 Newton. According to another embodiment, the hardness exhibited by the granules is at least 40 Newton. According to another embodiment, the hardness exhibited by the granules is at least 50 Newton. The hardness exhibited by the granules can be estimated by hardness testers such as the ones provided by Shimadzu, Brinell Hardness (AKB-3000 Model), Mecmesin, Agilent, Vinsyst, Ametek and Rockwell.

According to an embodiment, the water disintegrable granules comprising the water insoluble material or algae or the pesticidal active exhibit superior properties of disintegration. Disintegration can be defined as the complete breakdown exhibited by the granules on coming in contact with soil moisture or water. The Samples can be tested for disintegration time as per the CIPAC Handbook, "MT 187 for Disintegration of tablets". To carry out the test in one entire water disintegrable granule is added to a defined volume of CIPAC standard water and mixed by gentle stirring for the specified disintegration time of the tablet. The suspension is then passed through a 2000 μm sieve. The absence of a residue on the screen indicates complete disintegration of the tablet According to an embodiment, the disintegration time exhibited by the water disintegrable granules is less than 200 minutes. The disintegration is typically higher for those granules which are subjected to granulation for a longer time, in, the pan granulator and/or the pin agglomerator. It can be higher also, if the pan granulator is driven at a high speed (higher rotations per minute). Granules may be subjected to a longer granulation time in the fluid bed dryer, pin agglomerator and pan granulator, in order to give more compact, smooth-surfaced, almost spherical granules, which will release the agrochemical over a longer period of time. Thus it is possible to deliver compositions for providing nutrtion or crop protection, based on a specific plant, and address sustained crop protection and nutrition, based on the crop cycle. According to an embodiment, the disintegration time exhibited by the water disintegrable granules is less than 150 minutes. According to an embodiment, the disintegration time exhibited by the water disintegrable granules is less than 120 minutes. According to an embodiment, the disintegration time exhibited by the water disintegrable granules is less than 100 minutes. According to an embodiment, the disintegration time exhibited by the water disintegrable granules is less than 90 minutes. According to an embodiment, the disintegration time exhibited by the water disintegrable granules is less than 80 minutes. According to an embodiment, the disintegration time exhibited by the water disintegrable granules is less than 70 minutes. According to an embodiment, the disintegration time exhibited by the water disintegrable granules is less than 60 minutes. According to an embodiment, the disintegration time exhibited by the water disintegrable granules is less than 50 minutes. According to an embodiment, the disintegration time exhibited by the water disintegrable granules is less than 40 minutes. According to an embodiment, the disintegration time exhibited by the water disintegrable granules is less than 30 minutes. According to an embodiment, the disintegration time exhibited by the water disintegrable granules is less than 20 minutes. According to an embodiment, the disintegration time exhibited by the water disintegrable granules is less than 10 minutes. According to an embodiment, the disintegration time exhibited by the water disintegrable granules is less than 6 minutes. The disintegration time is estimated by disintegration testing equipments such as the ones provided by Electrolab Edutec, Arentek and Shimadzu.

According to an embodiment, the water disintegrable granules granules comprising the water insoluble material or algae or the pesticidal active exhibit superior wet sieve retention values.

The wet sieve retention value gives an estimate of the amount of non-dispersible material in the granular compositions that are applied as dispersions in water. The lower the wet sieve retention value, better is the dispersibility of the granular composition.

The Samples can be tested for wet sieve retention as per the CIPAC Handbook, "MT 185 Wet Sieve Test". A sample of the formulation is dispersed in water or allowed to completely disperse in water and the suspension formed is transferred to the sieve and washed. The amount of the material retained on the sieve is determined by drying and weighing.

According to an embodiment, the water disintegrable granules have a wet sieve retention value on a 75 micron sieve of less than 30%. According to an embodiment, the water disintegrable granules have a wet sieve retention value on a 75 micron sieve of less than 20%. According to an embodiment, the water disintegrable granules have a wet sieve retention value on a 75 micron sieve of less than 10%. According to an embodiment, the water disintegrable granules have a wet sieve retention value on a 75 micron sieve of less than 7%. According to an embodiment, the water disintegrable granules have a wet sieve retention value on a 75 micron sieve of less than 5%. According to an embodiment, the water disintegrable granules have a wet sieve retention value on a 75 micron sieve of less than 2%.

According to an embodiment, the water disintegrable granules comprising the water insoluble material or algae or the pesticidal active exhibit superior dispersibility. It can be seen from Table 5 that these water dispersible granular forms as per the embodiment of the invention exhibits a higher dispersibililty as compared to the water disintegrable granules of the invention leading to rapid uptake by the plants and thereby reducing their availability over a sustained period of the crop life cycle. Dispersibility can be defined as the ability of the granules to disperse on addition to water. The water disintegrable granules can be tested for dispersibility as per the CIPAC Handbook, "MT 174 Test for Dispersibility". A known amount of granule sample is added to a defined volume of water and mixed by stirring to form a suspension. After standing for a short period, the top nine-tenths are drawn off and the remaining tenth dried and determined gravimetrically. The method is virtually a shortened test of suspensibility and is appropriate for establishing the ease with which a granule disperses uniformly in water.

According to an embodiment, the water disintegrable granules have a dispersibility of at least 10%. According to an embodiment, the water disintegrable granules have a dispersibility of at least 20%. According to an embodiment, the water disintegrable granules have a dispersibility of at least 30%. According to an embodiment, the water disintegrable granules have a dispersibility of at least 40%. According to an embodiment, the water disintegrable granules have a dispersibility of at least 50%. According to an embodiment, the water disintegrable granules have a dispersibility of at least 60%. According to an embodiment, the water disintegrable granules have a dispersibility of at least 70%. According to an embodiment, the water disintegrable granules have a dispersibility of at least 80%. The wide range of dispersibility can be due to the composition being subjected to a longer granulation period, and also based on the percentage of nutrient, algae or pesticide, loaded in the composition. For example, granules which have been subjected to longer period of granulation in the pan granulator, or are subject to a faster rotation in the pan granulator, can become more, smooth compact and disperse more slowly than granules which are subject to a short period of granulation and where the pan granulator is driven at a lower speed (low rotations per minute).

According to an embodiment, it is desired that the granules of the composition disperse slowly, so as to release the agrochemical over a period of time. According to an embodiment, for shorter duration crop or for crops where the requirements are in the first 15 days of the crop life cycle, it may be desired that the granules have a higher dispersibility.

According to an embodiment, the water disintegrable granules comprising the water insoluble material or algae or the pesticidal active exhibit good suspensibility. Suspensibility can be defined as the amount of active ingredients (water insoluble nutrient) suspended after a given time in a column of liquid of a stated height and is expressed as a percentage of the amount of the ingredient in the original suspension. The water disintegrable granules can be tested for suspensibility as per the CIPAC Handbook, "MT 184 Test for Suspensibility" whereby a suspension of known concentration in CIPAC Standard Water is prepared, placed in a prescribed measuring cylinder at a constant temperature, and allowed to remain undisturbed for a specified time. The top $9/10$ths are drawn off and the remaining $1/10$th is then assayed either chemically, gravimetrically, or by solvent extraction, and the suspensibility is calculated.

According to an embodiment, the water disintegrable granules have a suspensibility of at least 5%. According to an embodiment, the water disintegrable granules have a suspensibility of at least 10%. According to an embodiment, the water disintegrable granules have a suspensibility of at least 20%. According to an embodiment, the water disintegrable granules have a suspensibility of at least 30%. According to an embodiment, the water disintegrable granules have a suspensibility of at least 40%. According to an embodiment, the water disintegrable granules have a suspensibility of at least 50%. According to an embodiment, the water disintegrable granules have a suspensibility of at least 60%. According to an embodiment, the water disintegrable granules have a suspensibility of at least 70%. According to an embodiment, the water disintegrable granules have a suspensibility of at least 80%.

According to an embodiment the water disintegrable granules comprising the water insoluble material or algae or the pesticidal active are polygonal, spherical, oval, or any polyhedral granules, without affecting the superior properties observed. According to an embodiment, the water disintegrable granules are substantially spherical.

According to an embodiment, the agrochemical excipients include surfactants, diluents, binders or binding agents, disintegrating agents, inert fillers, pH stabilizers spreading agents, sticking agents, antifoaming agents, carriers, antimicrobial agents, antifreezing agent, antioxidants, preservatives and agglomeration suppressants. However, those skilled in the art will appreciate that it is possible to utilize additional agrochemically acceptable excipients without departing from the scope of the present invention. The agrochemically acceptable excipients are commercially manufactured and available through various companies.

According to an embodiment, the agrochemical excipients are present in a concentration range of at least 99.9% by weight of the total composition. According to an embodiment, the agrochemical excipients are present in a concentration range of at least 99% by weight of the total composition. According to an embodiment, the agrochemical excipients is present in a concentration range of at least 95% by weight of the total composition. According to an embodiment, the agrochemical excipients are present in a concentration range of at least 90% by weight of the total composition. According to an embodiment, the agrochemical excipients are present in a concentration range of at least 80% by weight of the total composition. According to an embodiment, the agrochemical excipients are present in a concentration range of at least 70% by weight of the total composition. According to an embodiment, the agrochemical excipients are present in a concentration range of at least 60% by weight of the total composition. According to an embodiment, the agrochemical excipients are present in a concentration range of at least 50% by weight of the total composition. According to an embodiment, the agrochemical excipients are present in a concentration range of at least 40% by weight of the total composition. According to an embodiment, the agrochemical excipients are present in a concentration range of at least 30% by weight of the total composition. According to an embodiment, the agrochemical excipients are present in a concentration range of at least 20% by weight of the total composition. According to an embodiment, the agrochemical excipients are present in a concentration range of at least 10% by weight of the total composition. According to an embodiment, the agrochemical excipients are present in a concentration range of at least 5% by weight of the total composition.

According to an embodiment, the surfactants are present in an amount of 0.1% to 85% w/w of the total composition. According to an embodiment, the surfactants are present in an amount of 0.1% to 75% w/w of the total composition. According to an embodiment, the surfactants are present in an amount of 0.1% to 60% w/w of the total composition. According to an embodiment, the surfactants are present in an amount of 0.1% to 50% w/w of the total composition. According to an embodiment, the surfactants are present in an amount of 0.1% to 40% w/w of the total composition. According to an embodiment, the surfactants are present in an amount of 0.1% to 30% w/w of the total composition. According to a further embodiment, the surfactants are present in an amount of 0.1% to 20% w/w of the total composition. According to an embodiment, the surfactants are present in an amount of 0.1% to 10% w/w of the total composition. According to an embodiment, the surfactants are present in an amount of 0.1% to 5% w/w of the total composition.

According to an embodiment, the ratio of the algae to the agrochemically acceptable excipients is 99:1 to 1:99. According to an embodiment, the ratio of algae to the agrochemically acceptable excipients is 90:1 to 1:90. According to an embodiment, the ratio of algae to the agrochemically acceptable excipients is 80:1 to 1:80. According to an embodiment, the ratio of algae to the agrochemically acceptable excipients is 70:1 to 1:70. According to an embodiment, the ratio of algae to the agrochemically acceptable excipients is 60:1 to 1:60. According to an embodiment, the ratio of algae to the agrochemically acceptable excipients is 50:1 to 1:50. According to an embodiment, the ratio of algae to the agrochemically acceptable excipients is 40:1 to 1:40. According to an embodiment, the ratio of algae to the agrochemically acceptable excipients is 30:1 to 1:30. According to an embodiment, the ratio of algae to the agrochemically acceptable excipients is 20:1 to 1:20. According to an embodiment, the ratio of algae to the agrochemically acceptable excipients is 10:1 to 1:10. According to an embodiment, the ratio of algae to the agrochemically acceptable excipients is 5:1 to 1:5.

According to an embodiment, the ratio of algae to the surfactants or binders or disintegrating agents is 50:1 to 1:30. According to another embodiment, the ratio of algae to the surfactant or binder.

According to an embodiment, the ratio of algae to the surfactants or binders or disintegrating agents is 19:1. According to an embodiment, the ratio of algae to the surfactants or binders or disintegrating agents is 18:1. According to an embodiment, the ratio of algae to the surfactants or binders or disintegrating agents is 17:1. According to an embodiment, the ratio of algae to the surfactants or binders or disintegrating agents is 16:1. According to an embodiment, the ratio of algae to the surfactants or binders or disintegrating agents is 15:1. According to an embodiment, the ratio of algae to the surfactants or binders or disintegrating agents is 14:1. According to an embodiment, the ratio of algae to the surfactants or binders or disintegrating agents is 13:1. According to an embodiment, the ratio of algae to the surfactants or binders or disintegrating agents is 12:1. According to an embodiment, the ratio of algae to the surfactants or binders or disintegrating agents is 11:1. According to an embodiment, the ratio of algae to the surfactants or binders or disintegrating agents is 10:1. According to an embodiment, the ratio of algae to the surfactants or binders or disintegrating agents is 9:1. According to an embodiment, the ratio of algae to the surfactants or binders or disintegrating agents is 8:1. According to an embodiment, the ratio of algae to the surfactants or binders or disintegrating agents is 7:1. According to an embodiment, the ratio of algae to the surfactants or binders or disintegrating agents is 6:1. According to an embodiment, the ratio of algae to the surfactants or binders or disintegrating agents is 5:1. According to an embodiment, the ratio of algae to the surfactants or binders or disintegrating agents is 4:1. According to an embodiment, the ratio of algae to the surfactants or binders or disintegrating agents is 3:1. According to According to an embodiment, the ratio of algae to the surfactants or binders or disintegrating agents is 2:1. According to an embodiment, the ratio of algae to the surfactants or binders or disintegrating agents is 1:1. According to an embodiment, the ratio of algae to the surfactants or binders or disintegrating agents is 1:2. According to an embodiment, the ratio of algae to the surfactants or binders or disintegrating agents is 1:3. According to an embodiment, the ratio of algae to the surfactants or binders or disintegrating agents is 1:4. According to an embodiment, the ratio of algae to the surfactants or binders or disintegrating agents is 1:5. According to an embodiment, the ratio of algae to the surfactants or binders or disintegrating agents is 1:6. According to an embodiment, the ratio of algae to the surfactants or binders or disintegrating agents is 1:7. According to an embodiment, the ratio of algae to the surfactants or binders or disintegrating agents is 1:8. According to an embodiment, the ratio of algae to the surfactants or binders or disintegrating agents is 1:9. According to an embodiment, the ratio of algae to the surfactants or binders or disintegrating agents is 1:10. According to an embodiment, the ratio of algae to the surfactants or binders or disintegrating agents is 1:11. According to an embodiment, the ratio of algae to the surfactants or binders or disintegrating agents is 1:11. According to an embodiment, the ratio of algae to the surfactants or binders or disintegrating agents is 1:12. According to an embodiment, the ratio of algae to the surfactants or binders or disintegrating agents is 1:13. According to an embodiment, the ratio of algae to the surfactants or binders or disintegrating agents is 1:14. According to an embodiment, the ratio of algae to the surfactants or binders or disintegrating agents is 1:15. According to an embodiment, the ratio of algae to the surfactants or binders or disintegrating agents is 1:16. According to an embodiment, the ratio of algae to the surfactants or binders or disintegrating agents is 1:17. According to an embodiment, the ratio of algae to the surfactants or binders or disintegrating agents is 1:18. According to an embodiment, the ratio of algae to the surfactants or binders or disintegrating agents is 1:19. According to an embodiment, the ratio of algae to the surfactants or binders or disintegrating agents is 1:20. According to an embodiment, the ratio of algae to the surfactants or binders or disintegrating agents is 1:25. According to an embodiment, the ratio of algae to the surfactants or binders or disintegrating agents is 1:30. According to an embodiment, the ratio of algae to the surfactants or binders or disintegrating agents is 1:35. According to an embodiment, the ratio of algae to the surfactants or binders or disintegrating agents is 1:40. According to an embodiment, the ratio of algae to the surfactants or binders or disintegrating agents is 1:45. According to an embodiment, the ratio of algae to the surfactants or binders or disintegrating agents is 1:50. According to an embodiment, the ratio of algae to the surfactants or binders or disintegrating agents is 1:55. According to an embodiment, the ratio of algae to the surfactants or binders or disintegrating agents is 1:60. According to an embodiment, the ratio of algae to the surfactants or binders or disintegrating agents is 1:65. According to an embodiment, the ratio of algae to the surfactants or binders or disintegrating agents is 1:70. According to an embodiment, the ratio of algae to the surfactants or binders or disintegrating agents is 1:75. According to an embodiment, the ratio of algae to the surfactants or binders or disintegrating agents is 1:80. According to an embodiment, the ratio of algae to the surfactants or binders or disintegrating agents is 1:85. According to an embodiment, the ratio of algae to the surfactants or binders or disintegrating agents is 1:90. According to an embodiment, the ratio of algae to the surfactants or binders or disintegrating agents is 1:95. According to an embodiment, the ratio of algae to the surfactants or binders or disintegrating agents is 1:99. However, the ratios stated herein are only exemplary and those skilled in the art will appreciate.

According to an embodiment, the agrochemical excipients include surfactants, diluents, disintegrants and binders or binding agents. According to an embodiment, the agrochemical excipients comprise at least one of surfactants and binders. According to an embodiment, the surfactants include dispersing agents, wetting agents and emulsifiers. According to a further embodiment, the surfactants which are used in the composition include one or more of anionic, non-ionic, cationic and amphoteric surfactants. However, those skilled in the art will appreciate that it is possible to utilize other surfactants without departing from the scope of the present invention.

The anionic surfactants include one or more of, but not limited to a salt of fatty acid, a benzoate, a polycarboxylate, a salt of alkylsulfuric acid ester, Alkyl ether sulfates, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, sulfonate docusates, a salt of polyoxyethylene alkyl ether sulfuric acid ester, a polyoxyethylene alkylaryl ether sulfate, Alkyl sarcosinates, Alpha olefin sulfonate sodium salt, Alkyl benzene sulfonate or its sodium salt, calcium salt, sodium lauroyl sarcosinate, a Sulfosuccinates, Polyacrylates, Polyacrylates—free acid and sodium salt, salt of polyoxyethylene alkylaryl ether sulfuric acid ester, a polyoxyethylene alkyl ether phosphate, a salt of polyoxyethylene alkylaryl phosphoric acid ester, Sulfosuccinates-mono and other diesters, phosphate esters, Alkyl naphthalene sulfonate-isopropyl and butyl derivatives, Alkyl ether sulfates-sodium and ammonium salts; alkyl aryl ether phosphates, Ethylene oxides and its derivatives, a salt of polyoxyethylene aryl ether phosphoric acid ester, monoalkyl sulphosuccinates, aromatic hydrocarbon sulphonates, 2-Acrylamido-2-methylpropane sulfonic acid, Ammonium lauryl sulfate, Ammonium perfluorononanoate, Docusate, Disodium cocoamphodiacetate, Magnesium laureth sulfate, MBAS assay, Perfluorobutanesulfonic acid, Perfluorononanoic acid, carboxylates, Perfluorooctanesulfonic acid, Perfluorooctanoic acid, Phospholipid, Potassium lauryl sulfate, Soap, Soap substitute, Sodium alkyl sulfate, Sodium dodecyl sulfate, Sodium dodecylbenzenesulfonate, Sodium laurate, Sodium laureth sulfate, Sodium lauroyl sarcosinate, Sodium myreth sulfate, Sodium nonanoyloxybenzenesulfonate, Sodium pareth sulfate, alkyl carboxylates, Sodium stearate, alpha olefin sulphonates, Sulfolipid, naphthalene sulfonate salts, Alkyl naphthalene sulfonate fatty acid salts, Naphthalene sulfonate condensates-sodium salt, fluoro carboxylate, fatty alcohol sulphates, Alkyl naphthalene sulfonate condensates-sodium salt, a naphthalene sulfonic acid condensed with formaldehyde or a salt of alkylnaphthalene sulfonic acid condensed with formaldehyde; or salts, derivatives thereof.

The non-ionic surfactants include one or more of but not limited to polyol esters, polyol fatty acid esters, polyethoxylated esters, polyethoxylated alcohols, ethoxylated and propoxylated fatty alcohols, ethoxylated and propoxylated short-chain alcohols, EO/PO copolymers; di, tri-block copolymers; block copolymers of polyethylene glycol and polypropylene glycol, poloxamers, polysorbates, alkyl polysaccharides such as alkyl polyglycosides and blends thereof, amine ethoxylates, sorbitan fatty acid ester, glycol and glycerol esters, glucosidyl alkyl ethers, sorbitan alkyl esters, sodium tallowate, polyoxyethylene glycol, sorbitan alkyl esters, sorbitan derivatives, fatty acid esters of sorbitan (Spans) and their ethoxylated derivatives (Tweens), and sucrose esters of fatty acids, Alkyl polyglycoside, Cetomacrogol 1000, Cetostearyl alcohol, Cetyl alcohol, Cocamide DEA, Cocamide MEA, Decyl glucoside, Decyl polyglucose, Glycerol monostearate, IGEPAL CA-630, Isoceteth-20, Lauryl glucoside, Maltosides, Monolaurin, Mycosubtilin, Narrow-range ethoxylate, Nonidet P-40, Nonoxynol-9, Nonoxynols, NP-40, Octaethylene glycol monododecyl ether, N-Octyl beta-D-thioglucopyranoside, Octyl glucoside, Oleyl alcohol, PEG-10 sunflower glycerides, Pentaethylene glycol monododecyl ether, Polidocanol, Poloxamer, Poloxamer 407, Polyethoxylated tallow amine, Polyglycerol polyricinoleate, Polysorbate, Polysorbate 20, Polysorbate 80, Sorbitan, Sorbitan monolaurate, Sorbitan monostearate, Sorbitan tristearate, Stearyl alcohol, Surfactin, Triton X-100, Tween 80, polyethylene glycol, glyceryl laureate, lauryl glucoside, nonylphenolpolyethoxyethanols, nonyl phenol polyglycol ether, castor oil ethoxylate, polyglycol ethers, polyadducts of ethylene oxide and propylene oxide, block copolymer of polyalkylene glycol ether and hydroxystearic acid, ethylene oxide propylene oxide block copolymer, tributylphenoxypolyethoxy ethanol, octylphenoxypolyethoxy ethanol, etho-propoxylatedtristyrlphenols, ethoxylated alcohols, polyoxy ethylene sorbitan, a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, Alcohol ethoxylates—C6 to C16/18 alcohols, linear and branched, Alcohol alkoxylates—various hydrophobes and EO/PO contents and ratios, Fatty acid esters—mono and diesters; lauric, stearic and oleic; Glycerol esters—with and without EO; lauric, stearic, cocoa and tall oil derived, Ethoxylated glycerine, Sorbitan esters—with and without EO; lauric, stearic and oleic based; mono and trimesters, Castor oil ethoxylates—5 to 200 moles EO; non-hydrogenated and hydrogenated, Polyethylene glycol—200, 300, 400, 600, 1450, 3350 and 8000, Methyl capped polyethylene glycol—350 and 550, Block polymers—liquid, paste and solid; wide range of EO/PO ratios, Alkyl polyglucosides, Amine oxides—ethoxylated and non-ethoxylated; alkyl dimethyl, Fatty amine ethoxylates—coco, tallow, stearyl, oleyl amines, a polyoxyethylene hydrogenated castor oil or a polyoxypropylene fatty acid ester; salts or derivatives, and mixtures thereof.

Amphoteric or Zwitterionic surfactants include one or more of, but not limited to one or more of betaine, Betaines—coco and lauryl amidopropyl betaines, Coco Alkyl Dimethyl Amine Oxides, Betaines—alkyl dimethyl betaines; C8 to C18. Alkyl dipropionates—sodium lauriminodipropionate, Cocoamidopropyl hydroxy sulfobetaine, imidazolines, phospholipids phosphatidylserine, phosphatidylethanolamine, phosphatidylcholine, and sphingomyelins, Lauryl Dimethylamine Oxide, alkyl amphoacetates and propionates, alkyl Ampho(di)acetates, block copolymer of polyalkylene glycol ether (PEG) and hydroxystearic acid, and diproprionates, lecithin and ethanolamine fatty amides; or salts, derivatives therof.

Cationic surfactants include one or more of, but not limited to Dialkyl dimethyl ammonium chlorides, Alkyl methyl ethoxylated ammonium chlorides or salts, Dodecyl-, Coco-, Hexadecyl-, Octadecyl-, Octadecyl/Behenyl-, Behenyl-, Cocoamidopropyl-, Trimethyl Ammonium Chloride; Coco-, Stearyl-, bis(2-hydroxyethyl)Methyl Ammonium Chloride, Benzalkonium Chloride, Alkyl-, Tetradecyl-, Octadecyl-Dimethyl Benzyl Ammonium Chloride, Dioctyl-, Di(Octyl-Decyl)-, Didecyl-, Dihexadecyl-Distearyl-, Di(Hydrogenated Tallow)-Dimethyl Ammonium Chloride, Di(Hydrogenated Tallow) Benzyl-, Trioctyl-, Tri(Octyl-Decyl)-, Tridodecyl-, Trihexadecyl-Methyl Ammonium Chloride, Dodecyl Trimethyl-, Dodecyl Dimethyl Benzyl-, Di-(Octyl-Decyl) Dimethyl, Didecyl Dimethyl-Ammonium Bromide, quaternised amine ethoxylates, Behentrimonium chloride, Benzalkonium chloride, Benzethonium chloride, Benzododecinium bromide, Bronidox, quaternary ammonium salts Carbethopendecinium bromide, Cetalkonium chloride, Cetrimonium bromide, Cetrimonium chloride, Cetylpyridinium chloride, Didecyldimethylammonium chloride, Dimethyldioctadecylammonium bromide, Dimethyldioctadecylammonium chloride, Domiphen bromide, Lauryl methyl gluceth-10 hydroxypropyl dimonium chloride, Octenidine dihydrochloride, Olaflur, N-Oleyl-1,3-propanediamine, Pahutoxin, Stearalkonium chloride, Tetramethylammonium hydroxide, Thonzonium bromide; salts or derivatives therof.

According to an embodiment the dispersants which are used in the water disintegrable granular composition comprising the water insoluble material or algae or the pesticidal active include one or more of polyvinyl pyrrolidone, polyvinyl alcohol, lignin sulphonates, phenol naphthalene sulphonates, alkali metal, alkaline earth metal and ammonium salts of lignosulfonic acid, lignin derivatives, ligno sulphonates, sodium lignosulfonates naphthalenesulfonic acid, phenolsulfonic acid, dibutylnaphthalene-sulfonic acid, alkylarylsulfonates, alkyl sulfates, alkylsulfonates, fatty alcohol sulfates, fatty acids and sulfated fatty alcohol glycol ethers, polyoxyethylene alkyl ethers, dioctyl sulfosuccinate, lauryl sulfate, polyoxyethylene alkyl ether sulphate, polyoxyethylene styryl phenyl ether sulfate ester salts and the like, alkali metal salts salt thereof, ammonium salts or amine salts, polyoxyethylene alkyl phenyl ether, polyoxyethylene styryl phenyl ether, polyoxyethylene alkyl esters, or polyoxyethylene sorbitan alkyl esters, and the like, mixture of sodium salt of naphthalene sulphonic acid urea formaldehyde condensate and sodium salt of phenol sulphonic formaldehyde condensate ethoxylated alkyl phenols, ethoxylated fatty acids, alkoxylated linear alcohols, polyaromatic sulfonates, sodium alkyl aryl sulfonates, glyceryl esters, ammonium salts of maleic anhydride copolymers, maleic anhydride copolymers, phosphate esters, condensation products of aryl sulphonic acids and formaldehyde, addition products of ethylene oxide and fatty acid esters, salts of addition products of ethylene oxide and fatty acid esters, formalin condensate of naphthalene sulfonate and alkylnaphthalene sulfonate, sulfonates of condensed naphthalene, naphthalene formaldehyde condensates, sodium salt of isodecyl sulfosuccinic acid half ester, polycarboxylates, sodium alkyl benzene sulfonates, sodium salts of sulfonated naphthalene, ammonium salts of sulfonated naphthalene, salts of polyacrylic acids, salts of phenol sulfonic acids and salts of naphthalene sulfonic acids, sodium salts of condensed phenolsulfonic acid as well as the napthalene sulfonate-formaldehyde condensates, sodium naphthalene sulfonate formaldehyde condensates, tristyrylphenol ethoxylate phosphate esters; aliphatic alcohol ethoxylates; alkyl ethoxylates; EO-PO block copolymers; graft copolymers, ammonium salts of sulfonated naphthalene, salts of polyacrylic acids, salts of phenol sulfonic acids and salts of naphthalene sulfonic acids.

Commercially available dispersing agents include "Morwet D425" (sodium naphthalene formaldehyde condensate ex Witco Corporation, USA) "Morwet EFW" Sulfated Alkyl Carboxylate and Alkyl Naphthalene Sulfonate-Sodium Salt "Tamol PP" (sodium salt of a phenolsulphonic acid condensate) "Reax 80N" (sodium lignosulphonate) "Wettol D1" sodium alkylnaphthalene sulphonate (ex BASF). However, those skilled in the art will appreciate that it is possible to utilize different dispersants without departing from the scope of the present invention. The dispersing agents are commercially manufactured and available through various companies.

According to an embodiment the wetting agents which are used in the water disintegrable granular composition comprising the water insoluble material or algae or the pesticidal active include one or more of phenol naphthalene sulphonates, alkyl naphthalene sulfonate, sodium alkyl naphthalene sulfonate, sodium salt of sulfonated alkylcarboxylate, polyoxyalkylated ethyl phenols, polyoxyethoxylated fatty alcohols, polyoxyethoxylated fatty amines, lignin derivatives, alkane sulfonates, alkylbenzene sulfonates, salts of polycarboxylic acids, salts of esters of sulfosuccinic acid, alkylnaphthalenesulphonates, alkylbenzenesulfonates, alkylpolyglycol ether sulfonates, alkyl ether phosphates, alkyl ether sulphates and alkyl sulfosuccinic monoesters. However, those skilled in the art will appreciate that it is possible to utilize different wetting agents without departing from the scope of the present invention. The wetting agents are commercially manufactured and available through various companies.

Emulsifiers that are commercially available include but are not limited to Atlas G5000, TERMUL 5429, TERMUL 2510, ECOTERIC®, EULSOGEN® 118, Genapol®X, Genapol®OX-080, Genapol® C 100, Emulsogen® EL 200, Arlacel P135, Hypermer 8261, Hypermer B239, Hypermer B261, Hypermer B246sf, Solutol HS 15, Promulgen™ D, Soprophor 7961P, Soprophor TSP/461, Soprophor TSP/724, Croduret 40, Etocas 200, Etocas 29, Rokacet R26, CHEMONIC OE-20, Triton™ N-101, Tween 20, 40, 60, 65, 80, Span20, 40, 60, 80, 83, 85, 120, Brij®, Triton™ Atlox 4912, Atlas G5000, TERMUL 3512, TERMUL 3015, TERMUL 5429. TERMUL 2510, ECOTERIC®, ECOTERIC® T85, ECOTERIC® T20, TERIC 12A4, EULSOGEN® 118, Genapol®X, Genapol®OX-080, Genapol® C 100, Emulsogen® EL 200, Arlacel P135, Hypermer 8261, Hypermer B239, Hypermer B261, Hypermer B246sf, Solutol HS 15, Promulgen™ D, Soprophor 7961P, Soprophor TSP/461, Soprophor TSP/724, Croduret 40, Etocas 200, Etocas 29, Rokacet R26, CHEMONIC OE-20, Triton™ N-101, Tween 20, 40, 60, 65, 80 and Span 20, 40, 60, 80, 83, 85, 120 can also be used. However, those skilled in the art will appreciate that it is possible to utilize other emulsifiers or surfactants without departing from the scope of the present invention. The emulsifiers are commercially manufactured and available through various companies.

According to an embodiment, binding agents that can be used in the composition comprising the water insoluble material or algae or the pesticidal active, are water soluble binders. According to an embodiment, illustrative examples of water soluble binding agents which can be used in the water disintegrable granular composition can be any one or more of carbohydrates such as monosaccharides, disaccharides, oligosaccharides and polysaccharides; proteins; lipids; glycolipids; glycoprotein; lipoprotein; and combinations and derivatives of these. The carbohydrate binders can include one or more of glucose, mannose, fructose, galactose, sucrose, lactose, maltose, xylose, arabinose, sorbitol, mannitol, trehalose, raffinose, stachyose, fructo-oligosaccharides, Amylose, amylopectin, modified starches, Cellulose, hemicellulose, pectins, hydrocolloids and mixtures thereof.

The binding agents can also include synthetic organic water soluble polymers such as ethylene oxide polymers or copolymers, propylene oxide copolymer, polyethylene glycols, polyethylene oxides, polyacrylamides, polyacrylates, polyvinyl pyrrolidone, polyalkyl pyrrolidone, polyvinyl alcohol, polyvinylmethyl ether, polyvinyl acrylates, polylactic acid, polyethoxylated fatty acids, polyethoxylated fatty alcohols and latex.

The binding agents can also include corn syrup; celluloses such as carboxymethylcellulose, ethylcellulose, hydroxyethylcellulose, hydroxy-methylethylcellulose, hydroxyethylpropylcellulose, methylhydroxyethyl-cellulose, methylcellulose; starches such as amylose, seagel, starch acetates, starch hydroxyethyl ethers, ionic starches, long-chain alkyl starches, dextrins, amine starches, phosphates starches, and dialdehyde starches; plant starches such as corn starch and potato starch; other carbohydrates such as pectin, amylopectin, xylan, xanthan gum, glycogen, agar, alginic acid, phycocolloids, chitin, gum arabic, guar gum, gum karaya, gum tragacanth and locust bean gum.

The binding agents can also include complex organic substances such as phenyl naphthalene sulphonate, lignin and nitrolignin; derivatives of lignin such as lignosulfonate salts illustratively including calcium lignosulfonate and sodium lignosulfonate and complex carbohydrate-based compositions containing organic and inorganic ingredients such as molasses.

According to further embodiment, the binding agents can also include protein binders which are selected based on solubility and can include one or more of simple proteins, conjugated proteins or derived proteins, water soluble proteins, acidic proteins, basic proteins, or derivatives thereof. According to further embodiment, the suitable protein binders can include one or more of Albumin, Histone, Protamine, Prolamine, Albuminoids, Phosphoprotein, Mucoprotein, Chromoprotein, Lactose, Proteinase, Pyruvate dehydrogenase, Ribonuclease, flavoprotein, Cytochrome C, Cerruloplasmin, Myoglobin, Lysozyme, Proteoses, Peptones, Chymotrypsin, Cytochromo C; Lactate dehydrogenase, Subtilisin, Trypsin, Actin, Myosin, Ricin, Lectin, Collagen, Fibroin, Adrenalin, Elastin; Soy extract, Zein; Ovalbumin and Gamma globulin or derivatives thereof. However, those skilled in the art will appreciate that it is possible to utilize different binding agents without departing from the scope of the present invention.

The binding agent can be present in amounts ranging from 0.1% to 50% by weight of the total dry weight of the water disintegrable granular composition. According to an embodiment, the binding agent is present in an amount ranging from 0.1% to 40% by weight of the total dry weight of the water disintegrable granular composition. According to an embodiment, the binding agent is present in an amount ranging from 0.1% to 30% by weight of the total dry weight of the water disintegrable granular composition. According to an embodiment, the binding agent is present in an amount ranging from 0.1% to 20% by weight of the total dry weight of the water disintegrable granular composition. According to an embodiment, the binding agent is present in an amount ranging from 0.1% to 15% by weight of the total dry weight of the water disintegrable granular composition. According to an embodiment, the binding agent is present in an amount ranging from 0.1% to 10% by weight of the total dry weight of the water disintegrable granular composition.

According to an embodiment, the suspending agents or suspension aid agents which are used in the water disintegrable granular composition include carbohydrates. The carbohydrates include one or more of glucose, mannose, fructose, galactose, sucrose, lactose, maltose, xylose, arabinose, sorbitol, mannitol, trehalose, Raffinose, stachyose, fructo-oligosaccharides, Amylose, amylopectin, modified starches, Cellulose, hemicellulose, pectins, hydrocolloids and mixtures thereof. According to an embodiment, the suspending aid is present in the range of about 0.1% to 50% w/w of the total composition. According to an embodiment, the suspending aid is present in the range of about 0.1% to 30% w/w of the total composition. According to a further embodiment, the suspending aid is present in the range of about 0.1% to 15% w/w of the total composition. According to a further embodiment, the suspending aid is present in the range of about 0.1% to 10% w/w of the total composition. According to a further embodiment, the suspending aid is present in the range of about 0.1% to 5% w/w of the total composition.

According to an embodiment, the disintegrating agents can be selected from, but not limited to one or more of inorganic water soluble salts e.g. sodium chloride, nitrate salts; water soluble organic compounds such as urea, agar, hydroxypropyl starch, carboxymethyl starch ether, tragacanth, gelatin, casein, microcrystalline cellulose, crosslinked sodium carboxymethyl cellulose, carboxymethyl cellulose, and carboxymethyl cellulose calcium, sodium tripolyphosphate, sodium hexametaphosphate, metal stearates, a cellulose powder, dextrin, a methacrylate copolymer, Polyplasdone® XL-10 crosslinked polyvinylpyrrolidone, poly(vinylpyrrolidone), a polyaminocarboxylic acid chelate compound, a sulfonated styrene-isobutylene-maleic anhydride copolymer, salts of polyacrylates of methacrylates, starch-polyacrylonitrile graft copolymer, sodium, potassium bicarbonates/carbonates or their mixtures or salts with acids such as citric and fumaric acid, or salts, derivatives thereof. However, those skilled in the art will appreciate that it is possible to utilize other disintegrating agents without departing from the scope of the present invention. The disintegrating agents are commercially manufactured and available through various companies.

According to an embodiment, the sticking agents include, but not limited to one or more of paraffin, terpene, a polyamide resin, polyacrylate, polyoxyethylene, wax, polyvinyl alkyl ether, an alkylphenol-formalin condensate, fatty acids, latex, aliphatic alcohols, vegetable oils such as cottonseed, or inorganic oils, petroleum distillates, modified trisiloxanes, polyglycol, polyethers, clatharates, a synthetic resin emulsion or salts or derivatives therof. However, those skilled in the art will appreciate that it is possible to utilize other sticking agents without departing from the scope of the present invention. The sticking agents are commercially manufactured and available through various companies.

According to an embodiment, the spreading agents can include, but not limited to one or more of cellulose powder, dextrin, modified starch, a polyaminocarboxylic acid chelate compound, crosslinked poly(vinylpyrrolidone), a copolymer of maleic acid with a styrene compound, a (meth)acrylic acid copolymer, a half ester of a polymer consisting of polyhydric alcohol with dicarboxylic anhydride, a water-soluble salt of polystyrenesulfonic acid, fatty acids, latex, aliphatic alcohols, vegetable oils such as cottonseed, or inorganic oils, petroleum distillates, modified trisiloxanes, polyglycol, polyethers, clatharates or salts or derivatives therof. However, those skilled in the art will appreciate that it is possible to utilize different spreading agents without departing from the scope of the present invention. The spreading agents are commercially manufactured and available through various companies.

According to an embodiment, the preservatives can include but are not limited to one or more of bactericides, anti-fungal agents, biocides, anti-microbial agents. Non limiting examples of preservatives can include one or more of benzoic acid, its esters and salts, para-hydroxybenzoic acid (paraben), its esters and salts, propionic acid and its salts, salicylic acid and its salts, 2,4-hexadienoic acid (sorbic acid) and its salt, formaldehyde and paraformaldehyde, 2-hydroxybiphenyl ether and its salts, 2-zincsulfidopyridine N-oxide, inorganic sulfites and bisulfites, sodium iodate, 1,2-Benzisothiazolin-3-one, chlorobutanol, dehydraacetic acid, formic acid, 1,6-bis(4-amidino-2-bromophenoxy)-n-hexane and its salts, 10-undecylenic acid and its salts, 5-amino-1,3-bis(2-ethylhexyl)-5-methylhexahydropyrimidine, 5-bromo-5-nitro-1,3-dioxane, 2-bromo-2-nitropropane-1,3-diol, 2,4-dichlorobenzyl alcohol, N-(4-chlorophenyl)-N'-(3,4-dichlorophenyl)urea, 4-chloro-m-cresol, 2,4,4'-trichloro-2'-hydroxydiphenyl ether, 4-chloro-3,5-dimethylphenol, 1,1'-methylene-bis(3-(1-hydroxymethyl-2,4-dioximidazolidin-5-yl)urea), poly(hexamethylenediguanide) hydrochloride, 2-phenoxyethanol, hexamethylenetetramine, 1-(3-chloroallyl)-3,5,7-triaza-1-azonia-adamantane chloride, 1(4-chlorophenoxy)-1-(1H-imidazol-1-yl)-3,3-dimethyl-2-butanone, 1,3-bis(hydroxymethyl)-5,5-dimethyl-2,4-imidazolidinedione, benzyl alcohol, octopirox, 1,2-dibromo-2,4-dicyanobutane, 2,2'-methylenebis(6-bromo-4-chlorophenol), bromochlorophene, dichlorophene, 2-benzyl-4-chlorophenol, 2-chloroacetamide, chlorhexidine, chlorhexidine acetate, chlorhexidine gluconate, chlorhexidine hydrochloride, 1-phenoxypropan-2-ol, N-alkyl(C12-C22)trimethylammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxymethylurea, 1,6-bis(4-amidinophenoxy)-n-hexane and its salts, glutaraldehyde, 5-ethyl-1-aza-3,7-dioxabicyclo(3.3.0)octane, 3-(4-chlorophenoxy)propane-1,2-diol, Hyamine, alkyl(C8-C18)dimethylbenzylammonium chloride, alkyl(C8-C18)dimethylbenzylammonium bromide, alkyl(C8-C18)dimethylbenzylammonium saccharinate, benzyl hemiformal, 3-iodo-2-propynyl butylcarbamate, sodium hydroxymethylaminoacetate, cetyltrimethylammonium bromide, cetylpyridinium chloride, and derivatives of 2H isothiazol-3-one (so-called isothiazolone derivatives) such as alkylisothiazolones (for example 2-methyl-2H-isothiazol-3-one, MIT; chloro-2-methyl-2H-isothiazol-3-one, CIT), benzoisothiazolones (for example 1,2-benzoisothiazol-3(2H)-one, BIT, commercially available as Proxel® types from ICI) or 2-methyl-4,5-trimethylene-2H-isothiazol-3-one (MTIT), propionic acid, C1-C4-alkyl para-hydroxybenzoate, an dichlorophene or salts or derivatives thereof. However, those skilled in the art will appreciate that it is possible to utilize different preservatives without departing from the scope of the present invention. The preservatives are commercially manufactured and available through various companies. According to an embodiment, the preservative is present in the amount of 0.1% to 20% w/w. According to an embodiment, the preservative is present in the amount of 0.1% to 10% w/w of the total composition.

According to an embodiment, the carriers used in the water disintegrable granular composition further include, one or more of solid carriers, liquid carriers or fillers. According to another embodiment, the carriers include mineral carriers, plant carriers, synthetic carriers and water-soluble carriers. However, those skilled in the art will appreciate that it is possible to utilize different carriers without departing from the scope of the present invention. The carriers are commercially manufactured and available through various companies.

The solid carriers include natural minerals such as quartz, clay, kaolinite, pyrophyllite, sericite, talc (talc powder, agalmatolite powder, etc.), non-swelling clays, synthetic and diatomaceous silicas, montmorillonite, montromolite, bauxite, hydrated aluminas, perlite, sodium bicarbonate, volclay, vermiculites, limestone, natural and synthetic silicates ex; calcium and magnesium silicates; titanium dioxide, hydroxides, silicates, carbonates and sulfates of calcium, sand, magnesium, aluminum and titanium; aluminum, titanium, magnesium, calcium and zinc oxides; calcium and magnesium carbonates; and charcoal, silicas, mica, china clay, acid clay, attapulgite, diatomaceous earth, calcined aluminas, derivatives thereof; chalk ex. Omya® chalks, fuller's earth, dolomite, kiesulguhr, loess, prophyllites, talc, mirabilite, starch, white carbon, Sericite, slaked lime, inorganic salts such as calcium carbonate, ammonium sulfate, sodium sulfate, potassium chloride, potassium and barium sulphates; derivatives thereof; organic solid carriers such as synthetic silicic acid, starch, cellulose, sulfur powder, urea powder, soybean meal, tobacco powder, flour, wood meal, a vegetable powder, derivatives thereof; plastic carriers such as polyethylene, polypropylene, poly(vinylidene chloride), derivatives thereof; urea, hollow inorganic bodies, hollow plastic bodies, gypsum, fumed silica (white carbon) and derivatives thereof.

Commercially available Silicates are Aerosil brands, Sipemat brands as Sipernat® 50S and CALFLO E, and aerogels Fa. Cabot, kaolin 1777, aluminosilicates, Wessalon® 50S. However, those skilled in the art will appreciate that it is possible to utilize different solid carriers without departing from the scope of the present invention. The solid carriers are commercially manufactured and available through various companies.

The mineral carriers include one or more of kaolin minerals, such as dickite, nacrite, and halloysite; serpentines, such as chrysotile, lizardite, antigorite, and amesite; montmorillonite minerals, such as sodium montmorillonite, calcium montmorillonite, and magnesium montmorillonite; smectites, such as saponite, hectorite, sauconite, and hyderite; micas, such as agalmatolite, muscovite, phengite, sericite, and illite; silicas, such as cristobalite and quartz; hydrated magnesium silicates, such as attapulgite and sepiolite; calcium carbonates, such as dolomite and calcium carbonate fine powder; sulfate minerals, such as gypsum and gypsum; tuff, vermiculite, laponite, pumice, acid clay, and activated clay or derivatives thereof. However, those skilled in the art will appreciate that it is possible to utilize different mineral carriers without departing from the scope of the present invention.

The plant carriers include one or more of alcohols include cellulose, chaff, wheat flour, wood flour, starch, rice bran, wheat bran, and soybean flour. The synthetic carriers include one or more of wet process silicas, dry process silicas, calcined products of wet process silicas, surface-modified silicas, and modified starch (Pineflow, available from Matsutani Chemical industry Co., Ltd.). However, those skilled in the art will appreciate that it is possible to utilize different plant carriers without departing from the scope of the present invention.

The water-soluble carriers include one or more of soluble polymers, such as methyl cellulose, hydroxypropyl cellulose, hydroxypropyl methylcellulose, sodium carboxymethyl cellulose, propylene glycol alginate, polyvinylpyrrolidone, carboxyvinyl polymer, and casein sodium; urea, ammonium sulfate, sucrose, sodium chloride, salt cake, sodium carbonate, potassium carbonate, potassium pyrophosphate, sodium tripolyphosphate, maleic acid, fumaric acid, and malic acid. However, those skilled in the art will appreciate that it is possible to utilize different water soluble carriers without departing from the scope of the present invention. According to an embodiment, the carrier is present in the range of 0.1% to 98% w/w of the composition. According to an embodiment, the carrier is present in the range of 0.1% to 75% w/w of the composition. According to a further embodiment, the carrier is present in the range of 0.1% to 50% w/w of the composition. According to a further embodiment, the carrier is present in the range of 0.1% to 30% w/w of the composition. According to a further embodiment, the carrier is present in the range of 0.1% to 20% w/w of the composition. According to a further embodiment, the carrier is present in the range of 0.1% to 10% w/w of the composition. According to a further embodiment, the carrier is present can be the range of 0.1% to 5% w/w of the composition.

According to an embodiment, the fillers or diluents which can be used in the composition can include but are not limited to one or more of attapulgite, clay, kaolinites, montmorillonite, bauxite, hydrated aluminas, calcined aluminas, diatomaceous earth, chalk, fuller's earth, dolomite, kiesulguhr, loess, prophyllites, talc, vermiculites, limestone, natural and synthetic silicates, titanium dioxide, calcium and magnesium silicates, synthetic and diatomaceous silicas, mica and china clay, fertilizers such as, for example, ammonium, sodium, zinc, magnesium and potassium sulfates, sucrose, aluminum, calcium and zinc oxide, sodium benzoate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins; mineral earths and, bole, loess, talc, chalk, dolomite, limestone, lime, carbonates (calcium, magnesium), sodium acetate, alkali metal and alkali earth phosphates, calcium phosphate, oxides (magnesium, aluminum, calcium and zinc), chlorides (potassium, sodium), microcrystalline cellulose (e.g. Avicel™), polyvinylpyrrolidone, Wessalon® 50S precipitated silica, starches, kaolin, saccharides (dextrose, fructose, lactose, mannitol, sorbitol, sucrose), dextrin, methylcellulose, hydroxy-ethylcellulose, powdered magnesia, charcoal, gypsum, calcium and barium sulfates, pyrophyllite, silicic acid, silicates and silica gels, water-soluble organic substances such as, for example, neopentyl glycol, polyethylene glycol or salts or derivatives thereof. The diluents are water soluble or water insoluble or mixtures thereof. The water-soluble diluents include one or more of salts, surfactants, carbohydrates or derivatives thereof. However, those skilled in the art will appreciate that it is possible to utilize different fillers or diluents without departing from the scope of the present invention. The fillers or diluents are commercially manufactured and available through various companies. According to an embodiment, the filler or diluent can be present in the range of 0.1% to 90% w/w of the composition. According to an embodiment, the filler or diluent can be present in the range of 0.1% to 75% w/w of the composition. According to a further embodiment, the filler or diluent can be present in the range of 0.1% to 50% w/w of the composition. According to a further embodiment, the filler or diluent is present in the range of 0.1% to 30% w/w of the composition. According to a further embodiment, the filler or diluent can be present in the range of 0.1% to 20% w/w of the composition. According to a further embodiment, the filler or diluent is present in the range of 0.1% to 10% w/w of the composition. According to a further embodiment, the filler or diluent can be present in the range of 0.1% to 5% w/w of the composition. According to an embodiment, the fillers are only used optionally in the composition.

According to an embodiment, the water disintegrable granular composition of water insoluble nutrients further comprises one or more of biostimulants, pesticidal actives, water soluble fertilizers and macronutrients.

According to an embodiment, the biostimulants are selected from one or more of microalgae or algae, enzymes, humic acid, fulvic acid, sea weeds, bacteriospores and microbes such as fungi, yeast and viruses. The biostimulants used, are commercially manufactured and available from various manufacturers. However, those skilled in the art will appreciate that it is possible to utilize different biostimulants without departing from the scope of the present invention.

According to an embodiment, the water disintegrable granular composition of one or more algal actives further includes at least one of water insoluble nutrients, biostimulants, pesticidal actives, water soluble fertilizers and macronutrients.

According to an embodiment, the water disintegrable granular composition of one or more pesticides further includes at least one of water insoluble nutrients, biostimulants, algal actives, water soluble fertilizers and macronutrients.

According to an embodiment, the bacteriospores include spores of one or more of *Agrobacterium radiobacter, Azotobacter chrococcum, Azospirillum lippoferum, Azospirillum brasilense, Azospirillum lipoferum, Azospirillum irakense, Azospirillum halopraeferens, Bacillus amyloliquifaciens, Bacillus altitudinis Bradyrhizobium japonicum, Bradyrhizobium elkanii, Bacillus acidiceler, Bacillus acidicola, Bacillus acidiproducens, Bacillus aealius, Bacillus aerius, Bacillus aerophilus, Bacillus agaradhaerens, Bacillus aidingemis, Bacillus akibai, Bacillus alcalophilm, Bacillus altitudmis, Bacillus algicola, Bacillus azotoformans, Bacillus badius, Bacillus atyabhaltai, Bacillus asahti, Bacillus atrophaem, Bacillus cohnii, Bacillus coagulam, Bacillus coahuilemls, Bacillus flexus, Bacillus firmus, Bacillus pseudofirmus, Bacillus thuringenesis, Bacillus subtillus, Bacillus aizawai, Bacillus cereus, Bacillus circulans, B. circuians, Bacillus thermolactis, Bacillus kurstaki, Bacillus lentimorbus, Bacillus licheniformis, Bacillus megaterium, Bacillus mycoides, Bacillus mojavensis, Bacillus mucillagenosus, Bukholderia cepacia, Bacillus horii, Bacillus humi, Bacillus polygoni, Bacillus popillae, Bacillus pumilus, Bacillus sphaericus, Bacillus neahonii, Bacillus mizhmtemis, Bacillus niabensis, Bacillus macirti, Bacillus polymyxa, Bacillus sonoremis, Bacillus sporothenmxlura, Bacillus stratosphericus, Bacillus subterraneus, Bacillus taeamis, Bacillus tequilemis, Bacillus fhermamarcticm, Bacillus thermoamyhvorans, Bacillus thermacloacae, Bacillus thermolactis, Bacillus ihioparans, Pesudomonas fluorescens, Pseudomonas solanacearum, Pseudomonas syringae, Pseudomonas cepacia, Agrobacterium radiobacter, Azotobacter chroococcum Azospirillum lippoferum, Peaenibacillus azotofixans, Peaenibacillus durum, Pasteuria penetrans. Rhizobium leguminosarum, Rhizobium tropici, Bukholderia cepacia, Streptomyces lydicus, Thiobacillus thiooxidans* and *Thiobacillus novellus*. According to an embodiment, the bacteriospores are present in a concentration range of 0.1% to 50% by weight of the total composition. According to an embodiment, the bacteriospores are present in a concentration range of 0.1% to 40% by weight of the total composition. According to an embodiment, the bacteriospores are present in a concentration range of 0.1% to 30% by weight of the total composition. According to an embodiment, the bacteriospores are present in a concentration range of 0.1% to 20% by weight of the total composition. According to an embodiment, the bacteriospores are present in a concentration range of 0.1% to 10% by weight of the total composition. According to an embodiment, the bacteriospores are present in a concentration range of 0.1% to 5% by weight of the total composition. However, those skilled in the art will appreciate that it is possible to use different bacteriospores without departing from the scope of the present invention. The bacteriospores and microbes are commercially manufactured and available through various companies.

According to an embodiment, the pesticidal actives which are included in the water disintegrable granular composition of water insoluble nutrients or algal actives include an antifoulant, an attractant, an insecticide, a fungicide, a herbicide, a nematicide, a pheromone, a defoliant, an acaricide, a plant growth regulator, an algicide, an antifeedant, an avicide, a bactericide, a bird repellent, a biopesticide, a biocide, a chemosterilant, a safener, an insect attractant, an insect repellent, a insect growth regulator, a mammal repellent, a mating disrupter, a disinfectant, a molluscicide, a antimicrobial, a miticide, an ovicide, a fumigant, a plant activator, a rodenticide, a synergist, a virucide, a repellent, a microbial pesticide, a plant incorporated protectant, other miscellaneous pesticidal active, or salts, derivatives and mixtures therefore. According to an embodiment, the pesticidal active is present in a concentration range of 0.1% to 99% by weight of the total composition. According to an embodiment, the pesticidal active is present in a concentration range of 0.1% to 80% by weight of the total composition. According to an embodiment, the pesticidal active is present in a concentration range of 0.1% to 60% by weight of the total composition. According to an embodiment, the pesticidal active is present in a concentration range of 0.1% to 40% by weight of the total composition. According to an embodiment, the pesticidal active is present in a concentration range of 0.1% to 20% by weight of the total composition. According to an embodiment, the pesticidal active is present in a concentration range of 0.1% to 5% by weight of the total composition.

According to further embodiment, the macronutrients are selected from at least one of carbohydrates, fats, proteins, fibres, antioxidants and mixtures thereof. However, those skilled in the art will appreciate that it is possible to use different macronutrients without departing from the scope of the present invention. The macronutrients are commercially manufactured and available through various companies.

According to another embodiment, the water soluble fertilizer is selected from at least one of urea, sulphur based fertilizers, phosphate fertilizer such as MAP, DAP, potash fertilizer, nitrogen fertilizer, NPK fertilizers or derivatives, salts, complexes and mixtures thereof According to an embodiment, the water soluble fertilizers include one or more of ferrous sulphate, magnesium sulphate, manganese sulphate, copper sulphate, sodium molybdate, zinc sulphate, boric acid or derivatives, salts, complexes and mixtures thereof. According to an embodiment, the water soluble fertilizer is present in a concentration range of 0.1% to 85% by weight of the total composition. According to an embodiment, the water soluble fertilizer is present in a concentration range of 0.1% to 75% by weight of the total composition. According to an embodiment, the water soluble fertilizer is present in a concentration range of 0.1% to 60% by weight of the total composition. According to an embodiment, the water soluble fertilizer is present in a concentration range of 0.1% to 45% by weight of the total composition. According to an embodiment, the water soluble fertilizer is present in a concentration range of 0.1% to 25% by weight of the total composition. According to an embodiment, the water soluble fertilizer is present in a concentration range of 0.1% to 10% by weight of the total composition. According to an embodiment, the water soluble fertilizer is present in a concentration range of 0.1% to 5% by weight of the total composition. However, those skilled in the art will appreciate that it is possible to use other water soluble fertilizers without departing from the scope of the present invention.

According to an embodiment, the water insoluble nutrients which are included in the water disintegrable granular composition of pesticidal actives or algal actives include water insoluble fertilizers or micronutrients. According to an embodiment, the water insoluble nutrient comprises a mixture of one or more water insoluble fertilizers and one or more of micronutrients or their salts or derivatives or complexes thereof. According to an embodiment, the water insoluble fertilizer include at least one of a single nutrient fertilizers, multi-nutrient fertilizers, binary fertilizers, compound fertilizers, organic fertilizers, derivatives or mixtures thereof. However, those skilled in the art will appreciate that it is possible to utilize other fertilizers known in the art, without departing from the scope of the invention. According to an embodiment, the water insoluble fertilizer is one or more of nitrogen, phosphorous and potassium fertilizers or sulphur fertilizers, such as elemental sulphur.

According to an embodiment, the water insoluble nutrient in the form of micronutrients include minerals such as Boron, Calcium, Chlorine, Chromium, Cobalt, Copper, Fluorine, Iodine, Iron, Magnesium, Manganese, Molybdenum, Phosphorous, Potassium, Selenium, Silicon, Sodium, Zinc, or salts or derivatives of these minerals.

According to another embodiment, the invention further relates to the process for preparing the water disintegrable granular composition of water insoluble nutrients or the pesticidal actives or the algae. The water disintegrable granular composition is prepared by various techniques such as spray drying, pan pelletizing, agglomeration, extrusion or extrusion followed by spheronisation, etc.

According to an embodiment, the process of preparing the water disintegrable granular composition involves milling a blend of at least one water insoluble nutrient or the pesticidal actives or the algae, water and at least one agrochemically acceptable excipient to obtain a wet mix, for example, in the form of a slurry. The wet mix obtained is then dried to obtain a fine powder or a coarse granule or microgranule, for instance in a spray dryer, or any suitable drying equipment. The powder or the fine granules or microgranules are further subjected to agglomeration in an agglomerator. The agglomerator can include various equipments such as a disc pelletizer or pan granulator, pin agglomerator, spheronizer, or combinations thereof.

The process of agglomeration needs to be controlled in terms of feed rate and sequence of agglomeration equipment used, in order to result in granules possessing desired properties. For e.g. once the material from the spray drier is received, it can be subjected to further agglomeration in a fluid bed dryer, and the material is then fed to a pin agglomerator. Alternatively, the material from the spray drier is dried further in a fluid bed dryer and then fed via a screw or belt conveyor to a pan granulator. Pin agglomerators and disc pelletizers or pan agglomerators are available through various companies, for e.g. Feeco. Water or an aqueous suspension containing a binder may be added at the step of agglomeration, (during pan granulation or during pin agglomeratoring). The speed of the pin agglomerator can be controlled to give soft, low bulk density granules. Typically, the size of ther pellets coming out of the pin agglomerator is upto around 1 mm.

The speed of the pan granulator can be controlled to anywhere between 5 rpm to 100 rpm. Typically, the speed is kept between 5 and 60 rpm. The angle of the pan granulator can be adjusted to increase the size of the granules and subject them to more granulation. Typically, running the pan granulator at lower speeds results in rough, loosely packed granules of lower size. Processing the composition in the pan granulator at higher speeds provides, larger densely packed, almost spherical granules. The larger granules obtained with desired granule size, attrition resistance, hardness, and bulk density can be subjected to further drying in a post fluid bed dryer. The temperature can be kept anywhere between 35 C to 100 C, depending on the composition in the post fluid bed drier. The granules obtained from the granulator can also be dried in open air or air-dried, to remove any residual moisture, if any. However, those skilled in the art will appreciate that it is possible to modify or alter or change the process or process parameters without departing from the scope of the present invention. The water disintegrable granular composition obtained is in a size range of 0.1 mm to 6 mm, preferably 1 mm to 5 mm and includes particles in a size range of from 0.1 micron to 50 microns. The water disintegrable granules obtained have a hardness of at least 1N and a bulk density of less than 1.5 g/ml.

According to another embodiment, the invention relates to the use of the water disintegrable granular composition including the water insoluble nutrient or the algae as at least one of a fertilizer composition, a nutrient composition, a plant strengthener composition, a soil conditioner composition and a yield enhancer composition.

According to yet another embodiment, the invention relates to the use of the water disintegrable granular composition including the pesticidal active ingredient as a plant protectant composition.

According to yet another embodiment, the invention further relates to a method of improving plant health. The method involves treating at least one of a plant, a plant propagation material, a seed, seedling or the surrounding soil with the water disintegrable granular composition comprising: at least one water insoluble nutrient or at least one algae in a concentration range of from 5% to 90% by weight; and, at least one agrochemically acceptable excipient; wherein the granules are in a size range of 0.1 mm to 6 mm, and have a bulk density of less than 1.5 g/ml and a hardness of at least 1N.

According to an embodiment, the invention further relates to a method of fortification of the crops or the plant. The method involves application of the water disintegrable granular composition including one or more water insoluble nutrients or at least one algae in a concentration range of at least 0.1% upto 95% by weight; and, at least one agrochemically acceptable excipient; the composition being in a size range of 0.1 mm to 6 mm, with particles in a size range of from 0.1 micron to 50 microns; and, where the granules have bulk density of less than 1.5 gm/ml and hardness of at least 1 Newton to one or more of the plant, foliage of the plant, plant propagation material, locus of the plant or the plant propogation material, seeds, seedlings, soil and surroundings of the crop.

According to an embodiment, the invention further relates to a method of crop protection involving application of the water disintegrable granular composition including one or more pesticidal active ingredients in a concentration range of at least 0.1% upto 95% by weight; and, at least one agrochemically acceptable excipient the composition being in a size range of 0.1 mm to 6 mm, with particles in a size range of from 0.1 micron to 50 microns; and, where the granules have a bulk density of less than 1.5 gm/ml and hardness of at least 1 Newton to one or more of the plant, foliage of the plant, plant propagation material, locus of the plant or the plant propagation material, seeds, seedlings, soil and surroundings the crop.

The composition is applied through a variety of methods. Methods of applying to the soil includes any suitable method, which ensures that the composition penetrates the soil, for example, broadcasting through a mechanical applicator or by hand, nursery tray application, in furrow application, soil drenching, soil injection, or incorporation into the soil, and such other methods.

The rates of application or the dosage of the composition depends on the type of use, the type of crops, or the specific active ingredients in the composition but is such that the agrochemical active ingredient, is in an effective amount to provide the desired action (such as nutrient uptake plant vigor, crop yield).

Typically, the agricultural granular composition will not release the nutrient until after application to the desired target. Alternatively, the composition may be designed to release the agrochemical nutrient instantly and yet slowly over a period of time.

A. Preparation Examples

The following examples illustrate the basic methodology and versatility of the composition of the invention.

I. Water Disintegrable Granules Containing Different Nutrients and Pesticides

TABLE 1

| Constituents | Sample I | Sample II | Sample III | Sample IV | Sample V |
|---|---|---|---|---|---|
| Iron oxide | 6 | 65 | 80 | 90 | 95 |
| Mancozeb | — | 10 | — | — | — |
| Thiamethoxam | — | — | 8 | — | — |
| Naphthalene sulphonate condensate | 22 | 10 | 5 | 9.8 | 5 |
| Sodium Ligno Sulphonate | 20 | 10 | 5 | — | — |
| Polyvinyl pyrrolidone | — | 0.1 | 0.1 | 0.2 | — |
| Kaolin | 52 | 4.9 | 1.9 | — | — |
| Total | 100 | 100 | 100 | 100 | 100 |

Sample I was prepared by blending 6 parts of iron oxide, 22 parts of naphthalene sulphonate condensate and 20 parts of sodium ligno sulphonate to obtain a blend. The blend obtained was milled to get a powder of less than 50 micron particle size. The powder was mixed with water in a suitable mixing equipment to form a slurry with a solid content of 35% to 75%.

The slurry obtained was wet ground in suitable wet grinding equipment. The wet milled slurry obtained was spray dried at an inlet temperature less than 180° C. and outlet temperature less than 85° C. to get a granular powder with less than 10% moisture. The spray dried powder thus obtained was subjected to agglomeration in a fluid bed dryer, followed by a pin agglomerator and a pan granulator. The speed of the pan granulator was kept at around 35 rpm, to obtain the agricultural granular composition of Sample 1. Water was incorporated at the time of agglomeration. The granules obtained were then further dried in a post fluid bed drier to remove residual moisture, at a temperature around 70 C. The composition had the following particle size distribution: D10 less than 0.7 microns; D50 less than 4 microns and D90 less than 10 microns. The sample had a mean granule size of 3.8 mm. The composition has a bulk density of 1.2 gm/ml, an attrition resistance of 95%, and hardness of 45 N. The sample had a wet sieve retention value of 2.3% on a 75 micron sieve Samples II-V were prepared as per the process of preparation of Sample 1, wherein the samples included Iron oxide and other constituents in concentrations as set forth in Table 1.

II. Water Disintegrable Granules Containing Sulphur 5% to 95% w/w

TABLE 2

| Constituents | Sample I | Sample II | Sample III | Sample IV | Sample V | Sample VI |
|---|---|---|---|---|---|---|
| Sulphur | 5 | 40 | 55 | — | 90 | 95 |
| Azoxystrobin | — | — | — | 13.5 | — | — |
| Zn Oxide | — | — | 9.5 | 30 | — | — |
| Humic Acid | — | — | 9.5 | — | — | — |
| Sodium salt of sulfonated alkylcarboxylate | 22 | — | 12.5 | 25 | 4 | 3 |
| Polyoxyethylene alkyl phenyl ether | — | 8 | — | — | — | — |
| Maltodextrin | 9 | — | — | — | — | — |
| Starch | 2 | 11.5 | — | — | 4 | 2 |
| PVA | 0.2 | — | 0.1 | — | — | 0 |
| China Clay | 61.8 | 40 | 8.4 | 31.5 | 2 | 0 |
| Spirulina | — | — | 5 | — | — | — |
| Total | 100 | 100 | 100 | 100 | 100 | 100 |

Sample I was prepared by blending 5 parts of sulphur active ingredient, 22 parts of Sodium salt of sulfonated alkylcarboxylate, 2 parts of starch, 9 parts of maltodextrin and 61.8 parts of china clay to obtain a blend. The blend obtained was milled to get a powder of less than 50 micron particle size. The powder was mixed with water in a suitable mixing equipment to form a slurry with a solid content of 35% to 75%.

The slurry obtained was wet ground in a suitable wet grinding equipment. The wet milled slurry obtained was spray dried at an inlet temperature less than 140° C. and outlet temperature less than 55° C. to get microgranules or a granular powder with less than 10% moisture. The spray dried powder thus obtained was subjected to agglomeration in a pan granulator to obtain the agricultural granular composition of Sample 1. 0.2 parts of Polyvinyl alcohol was incorporated at the time of agglomeration. The composition had the following particle size distribution: D10 less than 0.7 microns; D50 less than 4 microns and D90 less than 10 microns. The sample had a mean average granule size of 2.8 mm, a bulk density of 1.1 g/c, and a hardness of 45N.

Samples II, V and VI were prepared as per the process of preparation of Sample 1, wherein the samples included Sulphur active ingredient and other constituents in varying concentrations as set forth in Table 1.

Samples III and IV were also prepared as per the process of preparation of Sample 1, wherein the samples included Sulphur plus humic acid and Zinc Oxide plus Azoxystrobin respectively, with other constituents in varying concentrations as set forth in Table 1.

III. Water Disintegrable Granules Containing Sulphur 50%-85% w/w and Iron Oxide/Zinc Oxide 10%-30% w/w.

TABLE 3

| Constituents | Sample I | Sample II | Sample III Weight % | Sample IV | Sample V |
|---|---|---|---|---|---|
| Sulphur | 50 | 55 | 70 | 80 | 85 |
| Iron Oxide | 30 | 3 | — | — | 10 |
| Zinc Oxide | — | 9.5 | 15 | 5 | — |
| Baccillus sp. | — | — | — | 5 | — |
| Phenol formaldehyde condensate | 10 | 15 | 15 | 9.8 | 3.1 |
| Sodium Ligno Sulphonate | 5 | 8 | — | — | 1.9 |
| Polyvinyl pyrrolidone | 0 | 0.1 | — | 0.2 | — |
| Kaolin | 5 | 9.4 | 0 | 0 | — |
| Total | 100 | 100 | 100 | 100 | 100 |

Sample I was prepared by blending 50 parts of sulphur active ingredient, 30 parts of Iron Oxide, 10 parts of phenol formaldehyde condensate and 5 parts of sodium ligno sulphonate to obtain a blend. The blend obtained was milled to get a powder of less than 50 micron particle size. The powder was mixed with water in a suitable mixing equipment to form a slurry with a solid content of 35% to 75%.

The slurry obtained was wet ground in a suitable wet grinding equipment. The wet milled slurry obtained was spray dried at an inlet temperature less than 140° C. and outlet temperature around 80° C. to get microgranules with less than 10% moisture. The spray dried powder or microgranules thus obtained was subjected to agglomeration in a fluid bed dryer and a pin agglomerator to obtain the water disintegrable granular composition of Sample 1. Moisture (water) was incorporated at the time of agglomeration. The composition had the following particle size distribution: D10 less than 0.7 microns; D50 less than 5 microns and D90 less than 20 microns. The composition had an averge granule size of 3 mm, bulk density of 1.15 gm/ml, hardness of 24N, and an attrition resistance of 87%. The composition had a wet sieve retention value of 1.8% on a 75 micron sieve.

Samples II-V were prepared as per the process of preparation of Sample I wherein the samples included Sulphur active ingredient and other constituents in concentrations as set forth in Table 3.

IV. Water Disintegrable Granules Containing Ferrous Sulphate, Copper Sulphate, Manganese Oxide, Boric Acid, Zinc Oxide and Sulphur.

TABLE 4

| Constituents | Sample I | Sample II Weight % | Sample III |
|---|---|---|---|
| Manganese oxide | 3 | — | 8.2 |
| Zinc Oxide | 8.7 | 15.5 | 6.5 |
| Boric acid | 8.8 | 7.5 | 8.5 |
| Sulphur | 50 | — | 35 |
| Ferrous sulphate | 11 | 15 | 8.5 |
| Copper Sulphate | 4 | — | 4 |
| Sodium molybdate | — | — | 0.5 |
| Maltodextrin | 3 | 10.2 | — |
| Sodium Lignosulphonate | 10.6 | 33.2 | 10.6 |
| Polyvinyl pyrrolidone | 0 | 0.2 | — |
| Kaolin | 1.4 | 18.4 | 18.2 |
| Total | 100 | 100 | 100 |

Sample I was prepared by blending 3 parts of manganese oxide, 8.2 parts of zinc oxide, 8.8 parts of boric acid, 50 parts of sulphur, 11 parts of Ferrous sulphate, 4 parts of copper sulphate and 10.6 parts of sodium ligno sulphonate, 3 parts of maltodextrin, 1.4 parts of kaolin, to obtain a blend. The blend obtained was milled to get a powder of less than 50 micron particle size. The powder was mixed with water in a suitable mixing equipment to form a slurry with a solid content of 35% to 75%.

The slurry obtained was wet ground in a suitable wet grinding equipment. The wet milled slurry obtained was spray dried at an inlet temperature less than 185° C. and outlet temperature less than 80° C. to get microgranules or powder with less than 10% moisture. The microgranules or powder thus obtained was subjected to agglomeration in a fluid bed dryer and a pin agglomerator to obtain the water disintegrable granular composition of Sample 1. Moisture (water) was incorporated at the time of agglomeration. The composition had the following particle size distribution: D10 less than 0.7 microns; D50 less than 8 microns and D90 less than 20 microns. The composition had an averge granule size of 1 mm, bulk density of 1.15 gm/ml, hardness of 10 N, and an attrition resistance of 87%. The composition had a wet sieve retention value of 1.8% on a 75 micron sieve.

Samples were prepared as per the process of preparation of Sample I wherein the samples included constituents in concentrations as set forth in Table 4.

V. Water Disintegrable Granules Containing Algae.

TABLE 5

| Constituents | Sample I | Sample II | Sample III | Sample IV | Sample V | Sample VI |
|---|---|---|---|---|---|---|
| Spirulina Sp. | — | 40 | — | — | — | 90 |
| Chlorella vulgaris. | 36.85 | — | 2 | 65- | 80% | — |
| 1,2-Benzisothiazolin-3-one | 0.15 | — | — | 0.85 | — | — |
| 1,2-dibromo-2,4-dicyanobutane | — | — | — | — | 2.1 | 0.5 |
| Maltodextrin | 14.10 | — | — | 11.7 | — | 1.1 |
| Starch | 8.90 | 12.5 | 35 | — | 13.5 | — |
| Naphthalene sulphonate condensate | 12 | 18 | 5 | — | 4.4 | 2.1 |
| Sodium Ligno Sulphonate | 4.2 | 7.7 | 14 | 10 | — | — |
| Polyvinyl alcohol | — | 0.2 | — | 0.1 | — | 0.2 |
| Kaolin | 23.8 | 21.6 | — | 12.35 | — | 6.1 |
| Total | 100 | 100 | — | 100 | 100 | 100 |

Sample I was prepared by blending 36.85 parts of Chlorella vulgaris dry biomass, 0.15 part of 1,2-Benzisothiazolin-3-one 4.10 parts of maltodextrin, 8.90 parts of starch, 12 parts of naphthalene sulphonate condensate, 4.2 parts of sodium ligno sulphonate and 23.8 parts of kaolin, to obtain a blend. The blend obtained was milled to get a powder of less than 50 micron particle size. The powder was mixed with water in a suitable mixing equipment to form a slurry with a solid content of 35% to 75%.

The slurry obtained was wet ground in suitable wet grinding equipment. The wet milled slurry obtained was spray dried at an inlet temperature less than 160° C. and outlet temperature less than 75° C. to get a granular powder with less than 10% moisture. The spray dried powder thus obtained was subjected to agglomeration to obtain the agricultural granular composition of Sample 1. The composition had the following particle size distribution: D10 less than 0.7 microns; D50 less than 4 microns and D90 less than 10 microns. The composition had a wet sieve retention value of 2.8% on a 75 micron sieve.

Samples II-VI were prepared as per the process of preparation of Sample 1, wherein the samples included *Chlorella* Sp. And *Spirulina* Sp. as active ingredient and other constituents in concentrations as set forth in the above table.

VI. Water Disintegrable Granules Containing Thiamethoxam or Azoxystrobin 0.1% to 95% w/w.

TABLE 6

| Constituents | Sample I | Sample II | Sample III | Sample IV |
|---|---|---|---|---|
| Thiamethoxam | — | 40 | 0.9 | — |
| Azoxystrobin | 23 | 12 | — | 70 |
| Zn Oxide | 9.8 | — | 40 | — |
| Urea | — | 5 | 20 | 7 |
| Polyoxyethylene alkyl phenyl ether | 5.5 | — | 2 | — |
| Sodium salt of Lignin Sulphonate | 19.5 | 22 | 20 | — |
| starch | — | 2 | 1 | 9.2 |
| Polyvinyl pyrrolidone | 0.5 | — | 0.2 | — |
| Clay | 41.7 | 19 | 15.9 | 13.8 |
| Total | 100 | 100 | 100 | 100 |

Sample I was prepared by blending 23 parts of azoxystrobin active ingredient, 9.8 parts of Zinc oxide, 5.5 parts of Polyoxyethylene alkyl phenyl ether, 19.5 parts of Sodium lignin sulphonate, and 41.7 parts of clay to obtain a blend. The blend obtained was milled to get a powder of less than 50 micron particle size. The powder was mixed with water in a suitable mixing equipment to form a slurry with a solid content of 35% to 75%.

The slurry obtained was wet ground in a suitable wet grinding equipment. The wet milled slurry obtained was spray dried at an inlet temperature less than 170° C. and outlet temperature less than 85° C. to get a granular powder with less than 100% moisture. The spray dried powder thus obtained was subjected to agglomeration in a pan granulator to obtain the agricultural granular composition of Sample 1. 0.5 parts of Polyvinylpyrrolidone was incorporated at the time of agglomeration. The composition had the following particle size distribution: D10 less than 0.9 microns; D50 less than 6 microns and D90 less than 15 microns. The sample had a mean average granule size of 3.8 mm, a bulk density of 1.2 g/ml, and a hardness of 48N. The composition had a wet sieve retention value of 2.5% on a 75 micron sieve.

Samples II-IV were prepared as per the process of preparation of Sample 1, wherein the samples included active ingredients and other constituents in varying concentrations as set forth in the above Table.

Comparison of the Physical Properties of Water Disintegrable Granules of Water Insoluble Nutrients:

TABLE 7

| Sample | Composition details | Bulk density (g/mL) | Hardness (Newton) | Disintegration time (min) | Attrition Resistance | Granule Size (mm) | Average Particle size (microns) (D50) | Dispersibility (%) | Suspensibility | Wet sieve retentino on a 75 micron sieve (%) | True Density (g/cm3) |
|---|---|---|---|---|---|---|---|---|---|---|---|
| C1 | Sulphur 90% agricultural granules as per embodiment of present invention | 0.92 | 40 N | 10 min | 98% | 1.0-4.00 | 3.37 | 20.4% | 39.8% | 3.1 | 1.95 |
| C2 | Sulphur 90% Water dispersible granules as per embodiment of WO2008084495 | 0.84 | N.A. | N.A. | 49% | 0.1-2.5 | 2.183 | 82% | 85% | 1.3 | 1.98 |
| C3 | 90% Sulphur bentonite pellets | 1.05 | 32 N | 25 min | 99.8% | 2.0-3.0 | 130 | Does not disperse | Nil | N.A. >90% | 2 |
| C4 | Sulfur 70% + Zinc oxide 15% water disintegrable granules as per embodiment of present invention | 1.1 | 51 N | 5 min | 99% | 1.5-4.00 | 4.49 | 46.1% | 20.9% | 1.5 | 1.96 |
| C5 | Sulphur 70% + Zinc oxide 15% WG as per the teachings of WO2012131702 | 0.89 | N.A. 0 | <1 min | 48% | 0.1-2.5 | 4.1839 | 78% | 74% | 2 | 1.87 |
| C6 | 85% MAP and 10% Sulphur water disintegrable granules as per the embodiment of the present invention | 1.09 | 38 N | 30 min | 98% | 1.5-4.00 | 3.49 | 20.4% | 39.8% | 3.6 | 2.2 |
| C7 | 85% MAP and 10% Sulphur | 1.8 | 34 N | 48 mins | 87% | 0.1-2.5 | 114.4 | Does not Disperse | N.A. Does not | 10.2 | 2.9 |

TABLE 7-continued

| Sample | Composition details | Bulk density (g/mL) | Hardness (Newton) | Disintegration time (min) | Attrition Resistance | Granule Size (mm) | Average Particle size (microns) (D50) | Dispersibility (%) | Suspensibility | Wet sieve retentino on a 75 micron sieve (%) | True Density (g/cm3) |
|---|---|---|---|---|---|---|---|---|---|---|---|
| | pellets as per the embodiment of WO2016183685 | | | | | | | | suspend | | |
| C8 | 55% Sulphur + 9.5% Zinc oxide + 3% Iron oxide water disintegrable granules prepared as per the embodiment of the present invention | 1.01 | 34 N | 35 mins | 98% | 1.5-4.00 | 4.45 | 46.1% | 84.2% | 2.8 | 1.97 |
| C9 | 55% Sulphur + 9.5% Zinc oxide + 3% Iron oxide water dispersible granules teachings of WO2012131702 | 0.89 | N.A. | N.A. | 43% | 0.1-2.5 | 4.253 | 59.4% | 67.9% | 1.8 | 1.95 |
| C10 | 55% Sulphur + 9.5% Zinc Oxide + 3% Iron oxide + 2.5% silicone dioxide based water disintegrable granules as per the embodiment of the present invention | 1.129 | 24.1 N | 22 mins | 98% | 1.5-4.00 | 3.47 | 31% | 58.8% | 3.3 | 2.1 |
| C11 | 55% Sulphur + 9.5% Zinc Oxide + 3% Iron oxide + 2.5% silicone dioxide based water dispersible granules teachings of WO2012131702 | 0.82 | N.A. | N.A. | 48% | 0.1-2.5 | 4.253 | 58.7% | 66.56% | 1.3 | 1.98 |
| C12 | 55% Sulphur + +9.5% Humic Acid + 9.5% ZnO + Spirulina 5% water disintegrable granules as per embodiment of present invention | 0.89 | 1.5 | 8 mins | 74% | 3.5-6.00 | 25.5 | 20% | 32% | 6.3 | 1.87 |
| C13 | Sulfur 50% + Iron oxide 30% water disintegrable granules as per embodiment of present invention | 1.09 | 68 N | 130 min | 96.9% | 1.5-4.00 | 5.49 | 48.1% | 15% | 1.5 | 2.15 |
| C14 | Zinc Oxide 15.5% + Boric acid 7.5% + Ferrous sulphate 15% + water disintegrable granules as per embodiment of present invention | 1.16 | 38.1 N | 26 mins | 98% | 2.5-5.00 | 12 | 32% | 44% | 3.1 | 2.4 |
| C15 | Zinc Oxide 15.5% + Boric acid 7.5% + Ferrous sulphate 15% liquid suspension | | N.A. | N.A. | NA | NA | 11.2 | 67.7% | 71.65% | 1.75 | |

TABLE 7-continued

| Sample | Composition details | Bulk density (g/mL) | Hardness (Newton) | Disintegration time (min) | Attrition Resistance | Granule Size (mm) | Average Particle size (microns) (D50) | Dispersibility (%) | Suspensibility | Wet sieve retentino on a 75 micron sieve (%) | True Density (g/cm3) |
|---|---|---|---|---|---|---|---|---|---|---|---|
| C16 | Sulphozinc (65% Sulphur + 18% Zinc Oxide Bentonite Pellets) | 1.02 | 24 N | 22 mins | 97% | 2.0-3.0 | 135 | 7.4% | N.A. Does not suspend | N.A. Very high, over 90% | 2.9 |

From table 7, it can be seen that the sample C1 Sulphur 90% water disintegrable granule, prepared as per the embodiment of present invention, possess a hardness of 40N as compared to the Sample C2 with 90% Sulphur water dispersible granules, prepared as per the embodiment of the WO2008084495 application which has no hardness, and exhibits an attrition resistance of as low as 49%, typically when granule size is around 0.5 mm to 2.5 mm.

Figure 5:
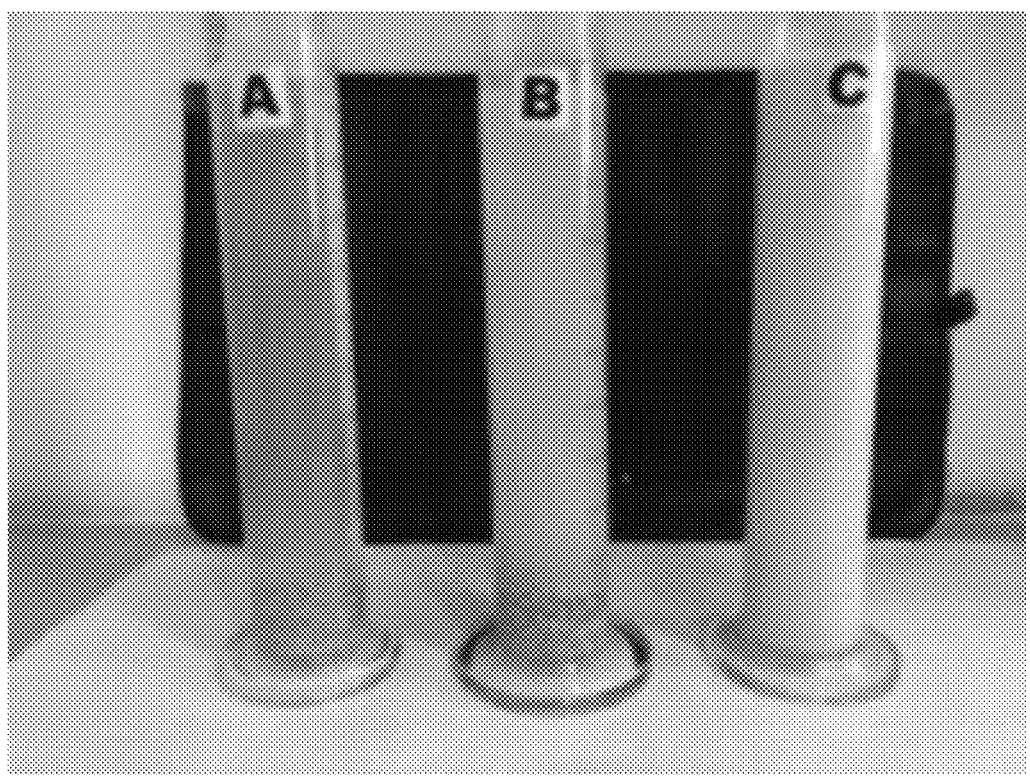
Figure 6:
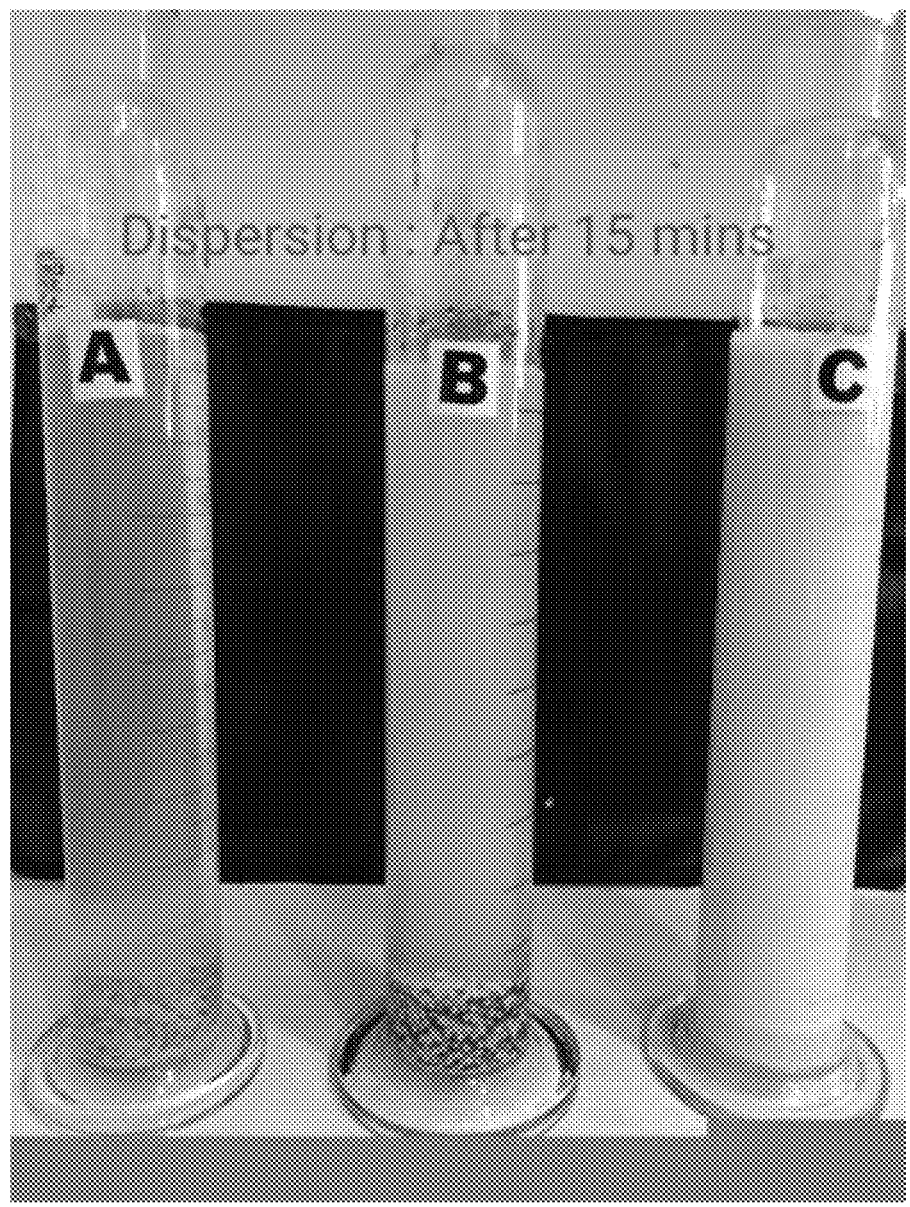
Figure 7:
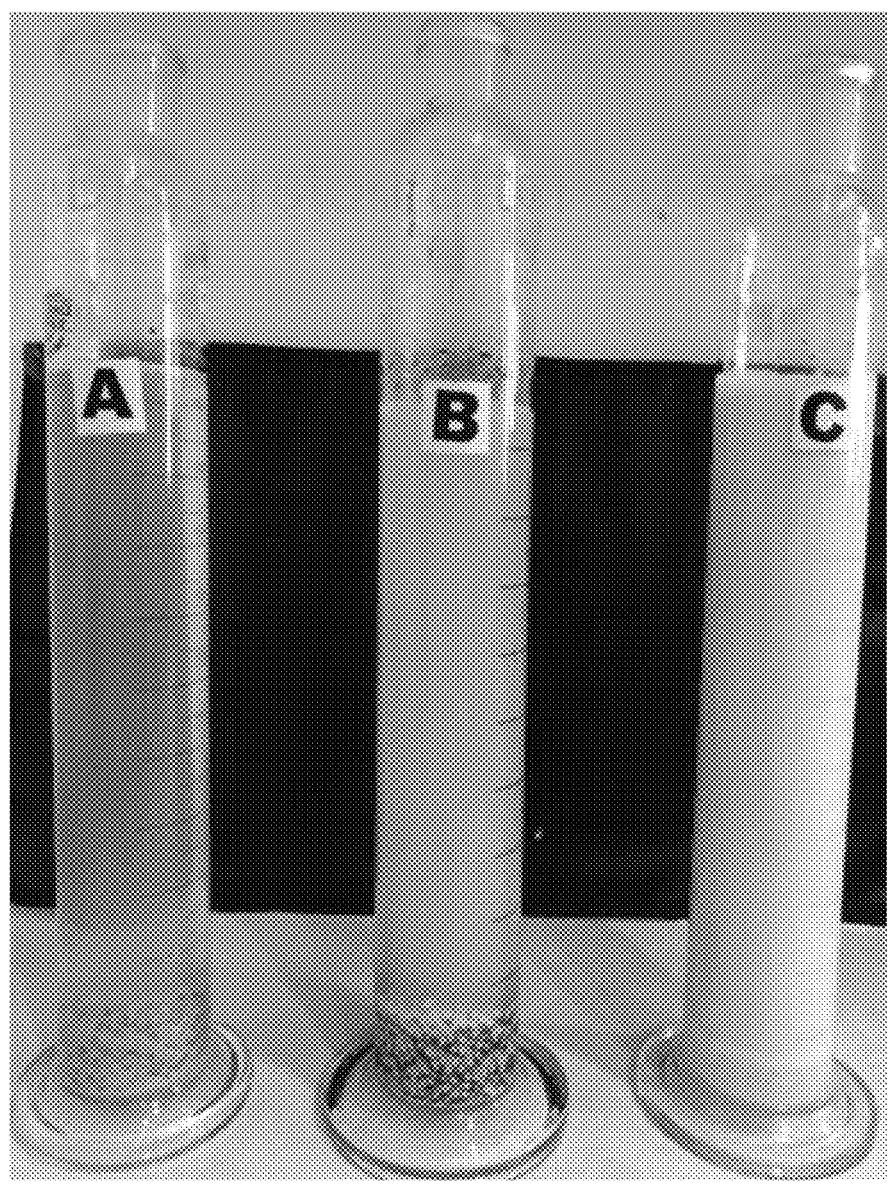
Figure 8:
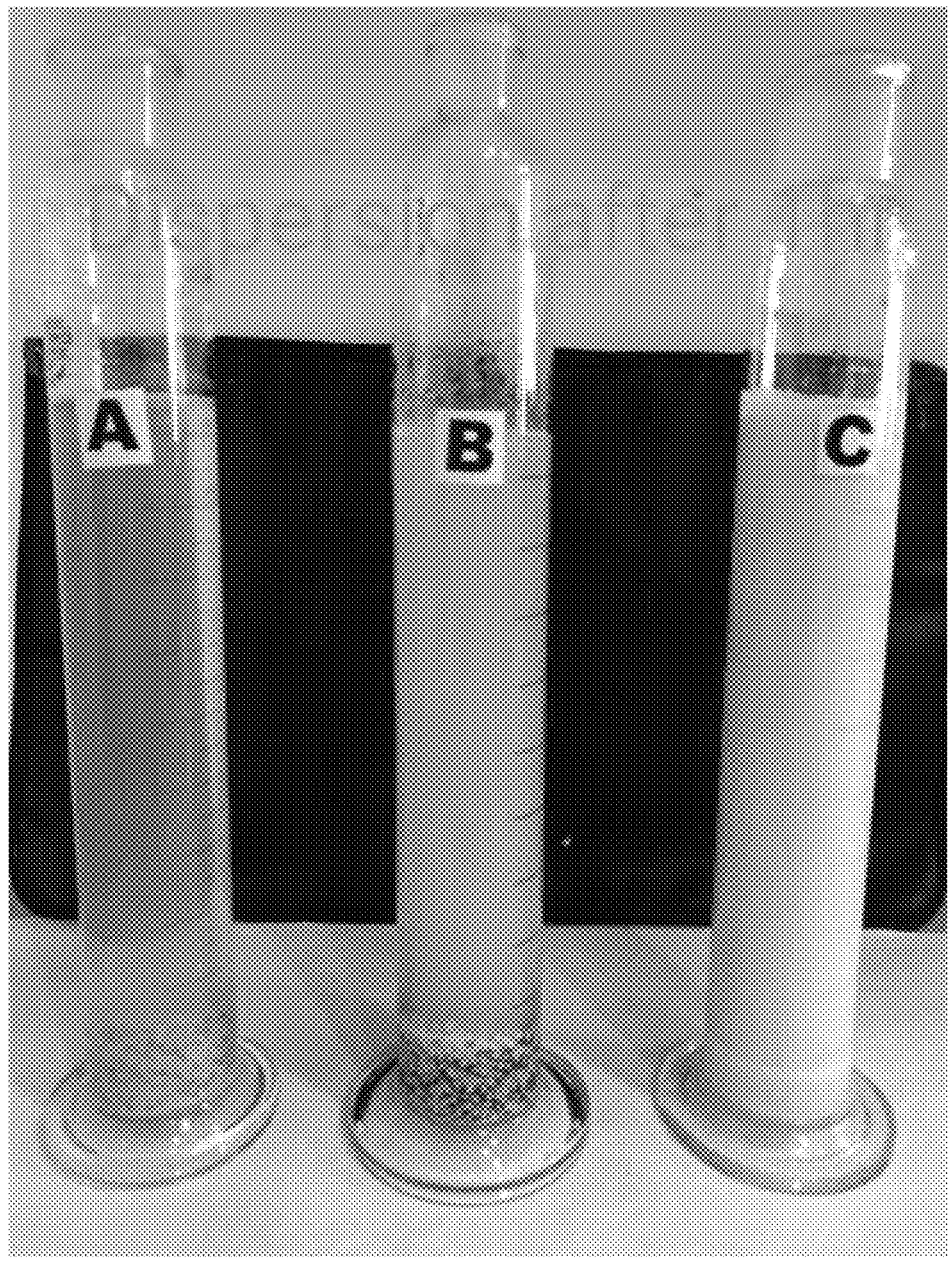
Figure 9:
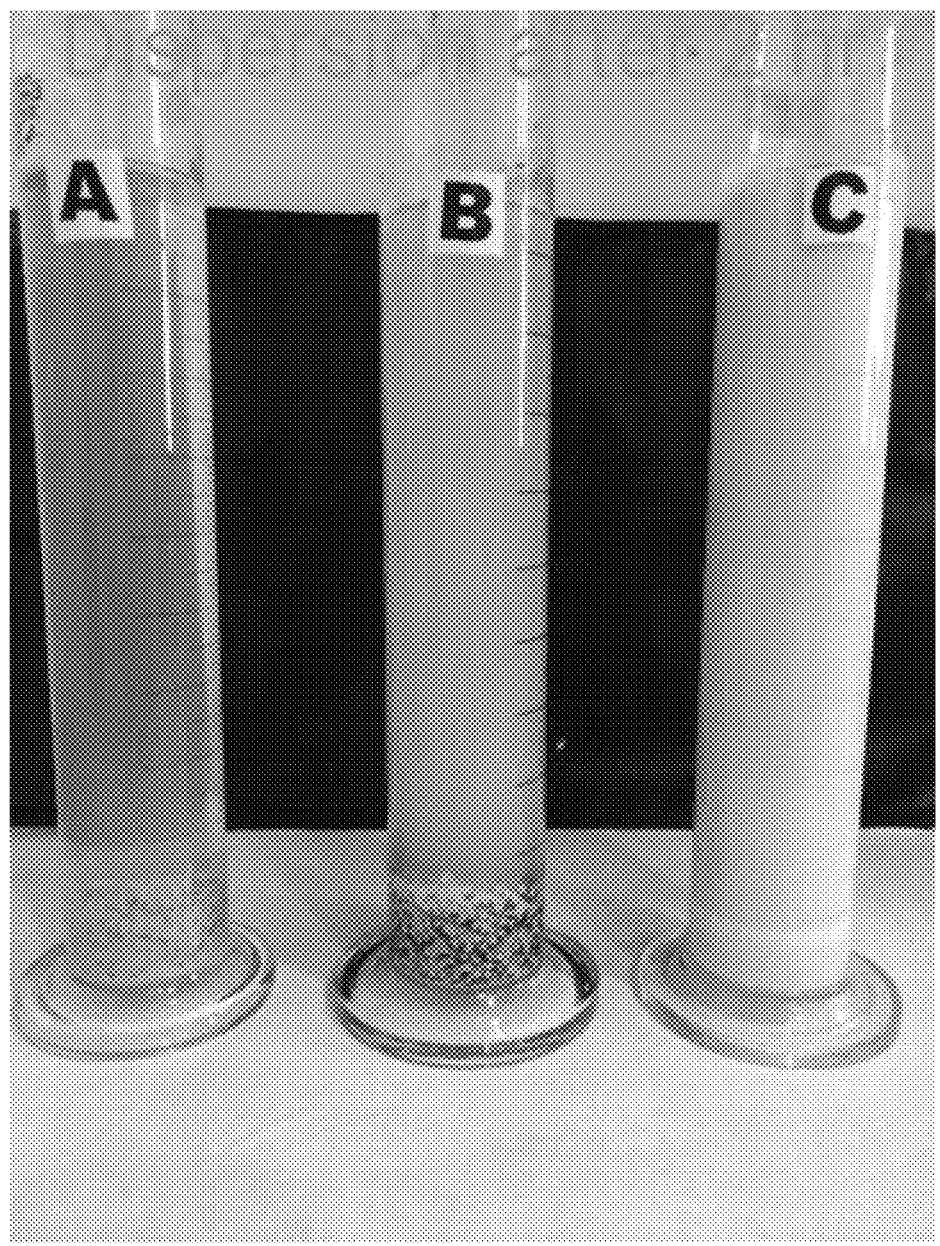
Figure 10:
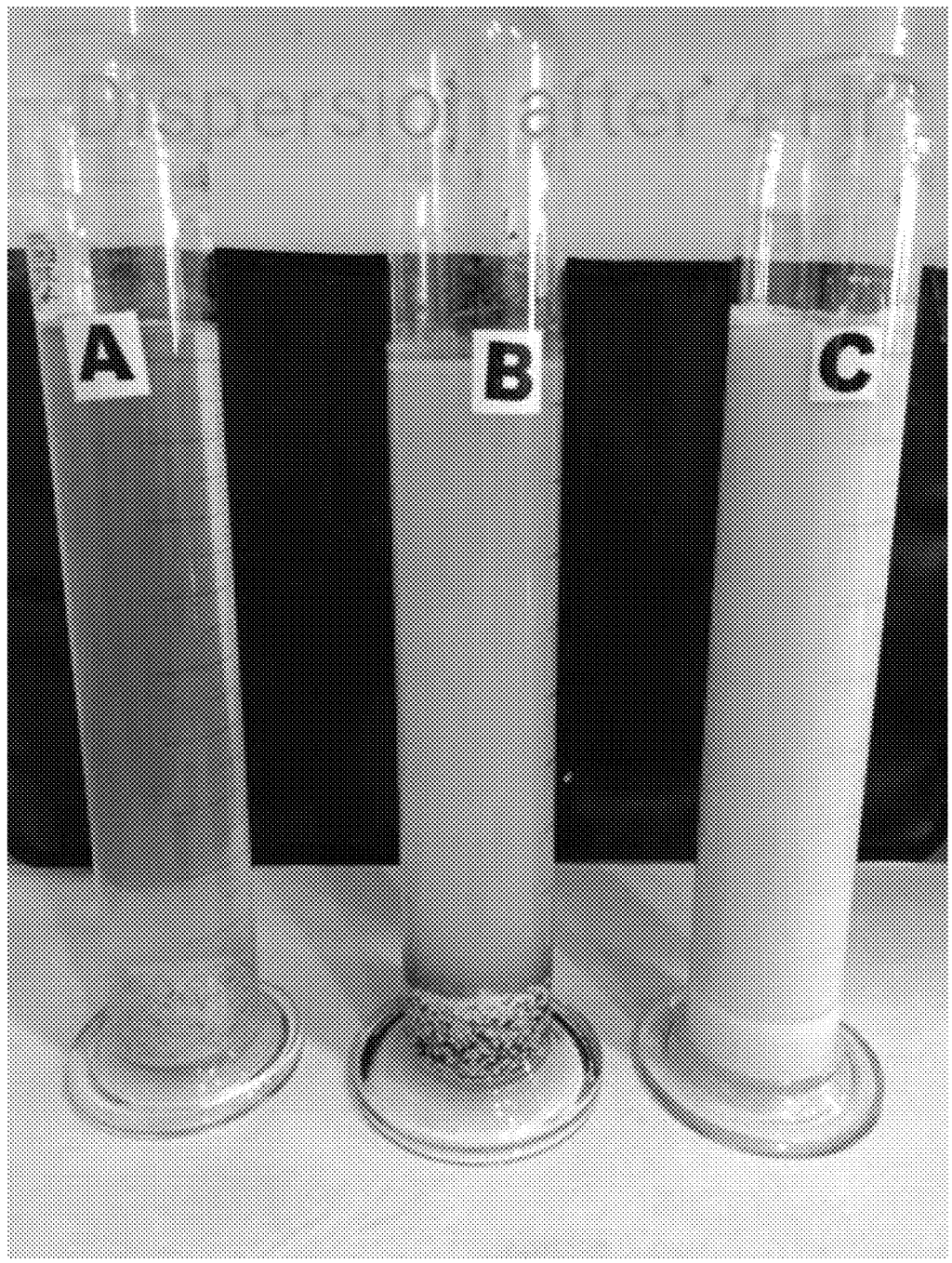

50 grams of each composition, C1, C2 and C3 were added to columns containing 500 ml of water and were kept without stirring. FIG. 5 shows the comparison between the 3 compositions C1 (column B) Sulphur 90 Granular composition according to an embodiment of the present invention, C2 (Column C) Sulphur 90 water dispersible granules according to WO2008084495, and C3 (Column A) sulphur bentonite granules. As can be seen, C2 disperses entirely and instantaneously upon contact with water.

FIG. 6-11 show the slow release and dispersion of the composition of the present invention C1, over 15 mins, 30 mins, 1 hour, 2 hours, 4 hours and 24 hours. It is observed that C3, prior art granules, do not disintegrate or disperse and barely releases the nutrient, and the column is practically a clear solution, even after 24 hours.

It can be further observed that while the sample C3 with 90% Sulphur bentonite pellets has similar hardness and attrition resistance as that of sample C1 with 90% Sulphur water disintegrable granules, these prior art pellets have a very high particle size, a very poor dispersibility and no suspensibility at all as leading to their poor field performance as can be seen from the tables below. While it is seen that these prior art pellets have a relatively low disintegration time, they are disintegrating only due to mechanical stirring. If left alone, as can be seen from FIG. 5-11, these bentonite granules, when applied to a column of water, without stirring, do not disintegrate for several hours, or even days. The problem is much more severe when such compositions are applied to soil. These prior art compositions suffer and lead to environmental waste and damage, as soils may not have sufficient moisture, and these prior art pellets do not auto-disintegrate or disperse as needed.

Also, the compositions C1, C4, C6, C8, C10, C12, C13, C14, C15, as per the embodiments of the present invention exhibit a superior hardness as compared to the samples prior art waater dispersible granular forms, which have no hardness. The compositions, according to embodiments of the present invention, also disperse and disintegrate slowly over a period of time, where the prior art water dispersible granular forms disperse instantaneously.

It is also seen that while the sample C16 with Sulphozinc 65% Sulphur+18% Zinc Oxide Bentonite Pellets) has comparable hardness and attrition resistance as that of sample C1 with Sulfur 70%+Zinc oxide 15% water disintegrable granules, these pellets have a very poor dispersibility and no suspensibility which can be attributed to their poor field performance as can be seen from the table below.

It is also observed that the sample C6 with 85% MAP (mono ammonium phosphate) and 10% Sulphur water disintegrable granules as per the embodiment of the present invention shows a bulk density of 1.09 g/ml as compared to the Sample C7 prepared as per the teachings of WO2016183685 which also contains 85% MAP and 10% Sulphur, however in the form of pellets, which exhibits a bulk density of as high as 1.8 g/ml. The prior art composition (sample C7) is formed through the process of extrusion and hard press in a Kahl pellet mill. The Sample C7 also exhibits a higher disintegration time and practically no dispersibility and no suspensibility as compared to the sample C6 as per the embodiments of the present invention.

Field Studies:

Efficacy of Various Treatments on Groundnut Growth and Development

Trials were laid in Kanpur, (Idar) village, Dist.-Sabarkantha, India, to evaluate various compositions for treatment of Groundnut GG-24 variety. The plot size was 228 m². All the recommended agronomic practices were followed. Compositions were applied by manual broadcasting. Observations for Plant height, Number of branches/plant, Number of pods/plant, yield and were made before and after 30 days, 60 days and 90 days of application. Final oil content was measured and recorded in terms of percentage values. Plant Height was recorded from 10 selected plants from each plot per replication. Number of Branches were recorded from 10 selected plants from each plot per replication. Number of pods were counted from 10 selected plants from each plot per replication. Yield was recorded from each plot and converted in to t/ha. Observations were also made to record the uptake of sulphur and zinc content in the plants at 30, 60 and 90 days after application. The observations were recorded as shown below:

TABLE 8

| Treatment No. | Composition details | Dose kg/acre | Plant height (cm) 30 DAA | Plant height (cm) 60 DAA | Plant height (cm) 90 DAA | Number of branches/plant 30 DAA | Number of branches/plant 60 DAA | Number of branches/plant 90 DAA | Number of pods/plant 60 DAA | Number of pods/plant 90 DAA | Yield (kg/ha) At harvest | Straw yield (kg/ha) |
|---|---|---|---|---|---|---|---|---|---|---|---|---|
| 1 | Sulfur 70% + Zinc oxide 15% water disintegrable granules (as per the embodiment of present invention) | 4 | 32.5 | 37.5 | 39.2 | 27.30 | 33.60 | 35.5 | 21.10 | 22.30 | 3016.12 | 2.091 |
| 2 | Sulfur 70% + Zinc oxide 15% water dispersible granules as per the teachings of WO2012131702 | 4 | 27.5 | 34.40 | 34.80 | 18.60 | 29.40 | 31.30 | 18.70 | 20.60 | 2833.33 | 1.943 |
| 3 | Sulphozinc (65% Sulphur + 18% Zinc Oxide Bentonite Pellets) | 8 | 24.3 | 29.1 | 29.5 | 14.2 | 25.2 | 26.5 | 15.1 | 17.1 | 2632.33 | 1.611 |
| 4 | 90% Sulphur Bentonite Pastilles + 33% ZnSO4 | 6 + 6 | 18.1 | 30.20 | 34.30 | 14.20 | 28.40 | 27.90 | 19.20 | 19.10 | 2146.67 | 1.301 |
| 5 | Untreated control | — | 11.6 | 22.70 | 23.1 | 9.20 | 19.7 | 21.5 | 15.10 | 15.20 | 1706.67 | 1.005 |

Available Sulphur and Zinc Content to Plant

TABLE 8A

| | | | Plant sample | | | | | |
|---|---|---|---|---|---|---|---|---|
| | | | Sulphur content (%) | | | Zinc content (ppm) | | |
| Sr. No. | Treatment | Dose (kg/acre) | 30 DAA | 60 DAA | 90 DAA | 30 DAA | 60 DAA | 90 DAA |
| 1 | Sulfur 70% + Zinc oxide 15% water disintegrable granules (as per embodiment of present invention) | 4 | 0.62 | 0.72 | 0.65 | 32.23 | 38.17 | 52.85 |
| 2 | Sulfur 70% + Zinc oxide 15% water dispersible granules as per WO2012131702 | 4 | 0.51 | 0.60 | 0.56 | 26.38 | 33.83 | 46.33 |
| 3 | 90% Sulphur Bentonite Pastilles + 33% ZnSO$_4$ | 10 + 10 | 0.43 | 0.51 | 0.49 | 21.72 | 32.83 | 42.50 |
| 4. | Sulphozinc (65% Sulphur + 18% Zinc Oxide Pellets) | 8 | 0.37 | 0.48 | 0.39 | 23.23 | 29.27 | 43.35 |
| 5 | Control | — | 0.32 | 0.38 | 0.29 | 21.62 | 27.17 | 42.33 |

It was observed from the above table that treatment 1 with Sulfur 70%+Zinc oxide 15% water disintegrable granules prepared as per the embodiment of the present invention not only showed an increased plant height at 30 days, 60 days and 90 days after application but also demonstrated increased number of branching and pegging per plant as compared to the treatment 2 with Sulfur 70%+Zinc oxide 15% water dispersible granules prepared as per the embodiments of WO2012131702. It was observed that the plant height with Treatment 1 was 12.64% higher and the number of branches per plant was 13.4% higher, as compared to Treatment 2, both at 90 days after application, even with the same amount of sulphur and zinc oxide applied in both treatments.

It was observed from the above table that treatment 1 with Sulfur 70%+Zinc oxide 15% water disintegrable granules as per the embodiment of the present invention showed a 12.8% and an 8% increase in the number of groundnut pods per plant at 60 days and 90 days after application, respectively, as compared to the treatment 2 with Sulfur 70%+Zinc oxide 15% water dispersible granules as per the embodiment of WO2012131702. Treatment 1 also show an enhancement in the total plant yield and straw yield as compared to Treatment 2. It is surprising to observe that application of treatment 1 in fact shows a 6.45% increase in the plant yield and a 7.6% increase in the straw yield at harvest as compared to treatment 2. This surprising result can be attributed to the fact that groundnut has a requirement for zinc upto 75 days after sowing, and the composition of the present invention (treatment 1), provided sulphur and zinc instantly as well as continuously to which led to greater pod development and a higher yield.

It is observed that the Treatment 2 with water dispersible granular composition of Sulphur and Zinc as per the teachings of WO2012131702, provides for only an instant availability actives whereas the surprisingly improved branching, number of pods per plant or significant improvement in the yield with the water disintegrable granular composition of Treatment 1, as per the embodiment of the present invention is attributed to the immediate and sustained availability of the nutrients for the entire duration of the crop life cycle. The surprising results are therefore attributed to the improved hardness of the water disintegrable granular composition of the present invention along with the reasonable dispersibility and suspensibility, there by allowing immediate as well as sustained release of nutrients by the composition of Treatment 1 (Sample C4 of Table 7) as compared to the composition of Treatment 3 (Sample C5 of Table 7).

It was further observed that the increase in the number of groundnut pods per plant and the overall yield with the composition of Treatment 1 containing Sulfur 70%+Zinc oxide 15% water disintegrable granules (as per embodiment of present invention) was found to be surprisingly higher even when the composition of Treatment 1 was applied at a dosage as low as 4 kgs per acre, as compared to the composition of Treatment 3 with Sulphozinc (65% Sulphur+18% Zinc Oxide Bentonite Pellets), when treatment 3 was applied at a dosage as high as 8 kgs per acre. It can be said that the particle size, low wet sieve retention value and dispersibility of the water disintegrable granular composition of Treatment 1 (Sample C4 of Table 7) as compared to the composition of Treatment 2 (Sample C5 of Table 7) was responsible for this surprising result.

It was further observed that the increase in the number of groundnut pods per plant and the overall yield with the composition of Treatment 1 containing Sulfur 70%+Zinc oxide 15% water disintegrable granules (as per embodiment of present invention) was found to be unexpectedly higher even when the composition of Treatment 1 was applied at a dosage as low as 4 kgs per acre, as compared to the composition of Treatment 5 which includes a composition 90% Sulphur Bentonite Pastilles+33% $ZnSO_4$ wherein 90% Sulphur Bentonite Pastilles were applied at a dosage of 6 kg/acre and 33% $ZnSO_4$ was applied at a dosage of 6 kg/acre.

It can be seen from the above table that treatment 1 with Sulfur 70%+Zinc oxide 15% Zinc water disintegrable granules (as per embodiment of present invention shows a significantly higher zinc and sulphur content in groundnut at 30 days, 60 days and 90 days after application as compared to the treatment 2 with Sulfur 70%+Zinc oxide 15% water dispersible granules prepared as per the teachings of WO2012131702. Application of treatment 1 in fact shows a 16% increase in the sulphur content and an increase of 14% in the zinc content at 90 days after application as compared to Treatment 2. The results are unexpected and surprising when the composition of Treatment 2 also contains the same concentration of Sulphur and Zinc and the difference is attributed to the slow but continuous availability of nutrients to the crop at adequate stages, from the composition of the present invention. The surprising results are further attributed to the improved form of the present invention whereby the water disintegrable granules exhibit improved attrition resistance and hardness as compared to the water dispersible granules of treatment 2 which easily crumble to fine dust particles post packaging and transportation as can be seen from FIG. 2, thereby resulting in their poorer efficacy. It was also once again observed that the Treatment 2 with water dispersible granular composition of Sulfur 70%+Zinc oxide 15% water dispersible granules as per WO2012131702 application provides for an instant uptake of actives and the nutrients are not available during later crop stages, whereas the water disintegrable granular composition (Treatment 1) of the invention provides for an instant and sustained availability of the nutrients for the entire duration of the crop life cycle thereby showing surprising results over the prior art compositions.

It was further observed that the plant uptake of sulphur and zinc is even higher with the composition of Treatment 1, as compared to the composition of Treatment 4 with Sulphozinc (65% Sulphur+18% Zinc Oxide Bentonite Pellets) when treatment 4 was applied at higher dosages. The improved particle size and enhanced suspensibility and dispersibility of the water disintegrable granular composition of Treatment 1 (Sample C4 of Table 7) as compared to the composition of Treatment 4 (Sample C16 of Table 7) leads to the improved uptake of sulphur and zinc with Treatment 1 as can be seen from the above table.

Efficacy of Various Treatments on Groundnut Yield and Yield Parameters

TABLE 8B

| Sr. no. | Treatments | Dose kg/acre | Plant height (cm) | | | Number of branches/plant | | | No. of pods/plant | | Total plant weight (kg/sqm) | Yield (kg/ha) | Straw yield (kg/ha) |
| --- | --- | --- | --- | --- | --- | --- | --- | --- | --- | --- | --- | --- | --- |
| | | | 30 DAA | 60 DAA | 90 DAA | 30 DAA | 60 DAA | 90 DAA | 60 DAA | 90 DAA | | At harvest | |
| 1 | 90% Sulphur water disintegrable granules as per the embodiment of present invention | 3 | 21.7 | 36.2 | 38.8 | 15.5 | 32.1 | 33.2 | 20.3 | 21.20 | 1.669 | 2598.33 | 140.3 |
| 2 | Sulphur 90% Water | 3 | 17.4 | 32.60 | 34.00 | 13.60 | 28.80 | 30.60 | 18.80 | 19.80 | 1.471 | 2320.00 | 1.239 |

TABLE 8B-continued

| Sr. no. | Treatments | Dose kg/acre | Plant height (cm) 30 DAA | Plant height (cm) 60 DAA | Plant height (cm) 90 DAA | Number of branches/plant 30 DAA | Number of branches/plant 60 DAA | Number of branches/plant 90 DAA | No. of pods/plant 60 DAA | No. of pods/plant 90 DAA | Total plant weight (kg/sqm) | Yield (kg/ha) At harvest | Straw yield (kg/ha) |
|---|---|---|---|---|---|---|---|---|---|---|---|---|---|
| | dispersible granules as per embodiment of WO2008084495 | | | | | | | | | | | | |
| 3 | 90% Sulphur Bentonite Pastilles | 8 | 15.6 | 30.2 | 33.6 | 11.7 | 29.3 | 28.4 | 16.90 | 18.20 | 1.350 | 2136.67 | 1.146 |
| 4 | Untreated control | — | 11.6 | 22.70 | 23.1 | 9.20 | 19.7 | 21.5 | 15.10 | 15.20 | 1.277 | 1706.67 | 1.005 |

TABLE 8C

| Sr. No. | Treatment | Dose (kg/acre) | PLANT SAMPLE Sulphur content (%) 30 DAA | PLANT SAMPLE Sulphur content (%) 60 DAA | PLANT SAMPLE Sulphur content (%) 90 DAA |
|---|---|---|---|---|---|
| 1 | Sulphur 90% water disintegrable granules prepared as per embodiment of present invention | 3 | 0.45 | 0.57 | 0.44 |
| 2 | Sulphur 90% Water dispersible granules prepared as per embodiment of WO2008084495 | 3 | 0.40 | 0.50 | 0.40 |
| 3. | 90% Sulphur Bentonite Pastilles | 8 | 0.36 | 0.42 | 0.36 |
| 4 | Control | — | 0.32 | 0.38 | 0.29 |

It was seen from the above table that treatment 1 with Sulphur 90% water disintegrable granules as per the embodiment of the present invention shows an increased plant height at 30 days, 60 days and 90 days after application increased number of branching and pegging per plant, as well as a significant increase in the number of groundnut pods per plant at 60 days and 90 days after application as compared to the treatment 2 with Sulphur 90% Water dispersible granules as per embodiment of the WO2008084495 application. It was observed that the plant height with Treatment 1 was 11.4% and 14.11% higher at 60 days and 90 days after application as compared to treatment 2. The results are surprisingly good and unexpected, as the composition of treatment 2 also contains the same concentration ie. 90% of Sulphur and has a similar particle size distribution as that of the agricultural granular composition of Treatment 1.

Treatments 1 also showed an enhanced increase in the total plant weight, plant yield and straw yield as compared to Treatment 2. It is surprising to observe that application of treatment 1 in fact shows a 13.46% increase in plant weight, a 11.99% increase in the overall yield and a 13.23% increase in the straw yield at harvest as compared to treatment 2. It can be said that the Treatment 2 with water dispersible granular composition of Sulphur as per the embodiment of WO2008084495 provides for an immediate uptake of actives and the effect is not prolonged, whereas the water disintegrable granular composition (Treatement 1) of the present invention provide for sustained availability of the nutrients for the entire duration of the crop life cycle thereby showing surprising results, such as higher yields, over the prior art compositions.

It was further observed that the increase in the number of groundnut pods per plant and the overall yield with the composition of Treatment 1 as per embodiment of present invention was found to be unexpectedly higher even when the composition of Treatment 1 was applied at a dosage as low as 4 kgs per acre, as compared to the composition of Treatment 4 which includes a 90% Sulphur Bentonite Pastilles applied at a dosage as high as 8 kgs/acre. The selected particle size distribution and enhanced suspensibility and dispersibility of the water disintegrable granular composition of Treatment 1 (Sample C1 of Table 7) as compared to the composition of Treatment 3 (Sample C3 of Table 7) attributes to the improved field efficacy with Treatment 1 as can be seen from the above table in terms of plant height, number of branches or pods per plant as well as the yield as compared to that of Treatment 3.

It can be seen from the above table that treatment 1 with Sulphur 90% water disintegrable granules as per the embodiment of the present invention show a significantly higher sulphur content in groundnut at 30 days, 60 days and 90 days after application as compared to the treatment 2 with Sulphur 90% Water dispersible granules as per embodiment of the WO2008084495 application. It was seen that after treatment 1 there was a 12%, 14% and 10% increase in the sulphur content at 30 days, 60 days and 90 days after application respectively, as compared to Treatment 2.

It was further observed that the increase in the uptake of sulphur with the composition of Treatment 1 as per embodiment of present invention was found to be unexpectedly higher even when the composition of Treatment 1 was applied at a dosage as low as 3 kgs per acre, as compared to the composition of Treatment 4 which includes a 90% Sulphur Bentonite Pastilles applied at a dosage as high as 8 kgs/acre. The improved particle size distribution and enhanced suspensibility and dispersibility of the water disintegrable granular composition of Treatment 1 (Sample C1 of Table 7) as compared to the composition of Treatment 3 (Sample C3 of Table 7) leads to the improved uptake of Sulphur with Treatment 1 as can be seen from the above table.

The higher sulphur content in the plant samples, at 30, 60 and 90 days in treatment 1, confirm the instant and sustained availability of the nutrients, as per the embodiments of the pending application throughout the entire crop duration, as compared to the prior art compositions.

Efficacy of Various Treatments on Groundnut Oil Content

TABLE 8D

| Treatment No. | Composition details | Dose kg/acre | Groundnut oil Content in % |
|---|---|---|---|
| 1 | Zinc Oxide 15.5% + Boric acid 7.5% +Ferrous sulphate 15% + water disintegrable granules as per embodiment of present invention | 2 | 52.85 |

TABLE 8D-continued

| Treatment No. | Composition details | Dose kg/acre | Groundnut oil Content in % |
|---|---|---|---|
| 2 | Zinc Oxide 15.5% + Boric acid 7.5% + Ferrous sulphate 15% liquid micronutrient suspension | 2 | 48.89 |
| 3 | Untreated control | — | 42.2 |

It can be seen from the above table that treatment 1 with Zinc Oxide 15.5%+Boric acid 7.5%+Ferrous sulphate 15% water disintegrable granules as per an embodiment of the present invention showed a significant increase of 12.7%% in the groundnut oil content as compared to the treatment 2 with Zinc Oxide 15.5%+Boric acid 7.5%+Ferrous sulphate 15% liquid micronutrient. The results are particularly surprising and can be attributed to the form of the composition of the present invention which instantaneously and continuously provides nutrients to the crop at the adequate stages as against the composition of Treatment 2 which has reduced availability of the nutrients during later stages to the crops and in turn the lower efficacy as can see from the above table.

Efficacy of Various Treatments on Paddy Yield and Yield Parameters

Field trials were conducted for evaluation of different treatments at Mahij (Bareja) village on Bodi (Punjab-S) variety of paddy. The plot size was 7.5×3.5=26.25 sqm. All the recommended agronomic practices were followed. Granules of the compositions according to the embodiments of the invention, and prior art, were applied by manual broadcasting. Observations for Plant height, Number of tillers/plant, Leaf colour, Root length, Panicle length were made after 30 days, 60 days and 85 days of application No. of grains/panicle, biological yield, grain yield and straw yield were measured. Sulphur and zinc content in the soil as well as the uptake of sulphur and zinc by the plants was measured. Panicle length was recorded from 10 selected panicles from each plot per replication. Biological yield, grain yield and straw yield was recorded from each plot per replication and converted in to t/ha.

The observations were recorded as shown below:

TABLE 9

| Sr. no. | Treatments | Dose kg/acre | Panicle length (cms) 60 DAA | Panicle length (cms) 85 DAA | Biological yield (t/ha) At harvest | Grain yield (t/ha) At harvest | Straw yield (t/ha) At harvest |
|---|---|---|---|---|---|---|---|
| 1 | Sulfur 70% + Zinc oxide 15% water disintegrable granules (as per embodiment of present invention) | 4 | 18.75 | 20.52 | 9.50 | 3.69 | 6.11 |
| 2 | Sulfur 70% + Zinc oxide 15% water dispersible granules prepared as per the embodiment of WO2012131702 | 4 | 17.70 | 18.10 | 8.20 | 3.38 | 5.52 |
| 3 | Sulphozinc - Sulphur 65% and Zinc 18% pastilles | 8 | 15.45 | 17.15 | 7.20 | 2.66 | 4.54 |
| 4 | 90% Sulphur Bentonite Pastilles + 33% $ZnSO_4$ | 10 + 10 | 17.70 | 17.00 | 7.47 | 2.84 | 4.64 |
| 5 | 85% MAP and 10% Sulphur water disintegrable granules as per the embodiment of the present invention | 4 | 17.85 | 19.72 | 10.75 | 3.02 | 4.87 |
| 6 | 85% MAP and 10% Sulphur pellets as per the embodiment of WO2016183685 | 4 | 14.48 | 16.45 | 7.89 | 2.65 | 4.21 |
| 7 | Untreated control | — | 14.35 | 14.48 | 6.30 | 2.39 | 4.01 |

It can be seen from the above table that treatment 1 with Sulfur 70%+Zinc oxide 15% water disintegrable granular composition as per the embodiment of the present invention showed a significant increase in the panicle length of paddy at 60 days and at 85 days after application respectively as compared to the treatment 2 with Sulfur 70%+Zinc oxide 15% water dispersible granules prepared as per the embodiment of WO2012131702. Treatment 1 also showed a good increase in the biological yield and straw yield in paddy as compared to Treatment 2. In fact, treatment 1 surprisingly showed a 13.37% increase in the panicle length at 85 days after application as compared to Treatment 2. Treatment 1 also showed a 15.85% increase in the biological yield and around 9-10% increase in the grain yield and straw yield as compared to the yield obtained with treatment 2. It can be said that the composition of the present invention is providing an adequate release of nutrients and making it available to the crop at the right stages.

Furthermore, it was observed that Treatment 3 with Sulphozinc containing Sulphur 65% and Zinc 18% pastilles, known in the art, showed a poor increase in the panicle length as well as the yield as compared to Treatment 1, even when the composition of Treatment 3 was applied at 8 kgs per acre which is twice the dosage at which the composition of treatment 1 has been applied.

The increase in the panicle length and the yield with the composition of treatment 1 comprising Sulfur 70%+Zinc oxide 15% agricultural granular composition (as per embodiment of present invention) was found to be unexpectedly high even when the composition of Treatment 1 was applied at a dosage as low as 4 kgs per acre as compared to the composition of Treatment 4 which includes a tank mix composition of 90% Sulphur Bentonite Pastilles+33% $ZnSO_4$ wherein 90% Sulphur Bentonite Pastilles were applied at a dosage of 10 kg/acre and 330% $ZnSO_4$ was applied at a dosage of 10 kg/acre.

It was further observed that the increase in the panicle length and the yield observed with the composition of Treatment 5 with the composition of 85% MAP and 10% Sulphur water disintegrable granules as per the embodiment of the present invention was found to be unexpectedly high as compared to the composition of Treatment 6 which includes 85% MAP and 10% Sulphur pellets as per the embodiment of WO2016183685. In fact, Treatment 5, showed a 13.96% increase in the grain yield and a 15.67% increase in the straw yield as compared to the composition of Treatment 6 prepared as per the embodiment of WO2016183685. The results are surprising when the composition of treatment 5 includes the same concentration of actives as that of the composition of Treatment 6 except for the composition of Treatment 5 being in a water disintegrable granular form whereby the composition exhibits lower bulk density and lower true density over the composition of Treatment 6 (prior art). Composition of treatment 5 according to an embodiment of the invention, is more loosely packed and able to release nutrients more gradually, oweing to a lower bulk density and a lower true density.

Efficacy of Various Treatments on Maize Yield and Other Plant Parameters

Field trial was conducted for the evaluation of different treatments at Laxmanpura (Idar) village for treatment of maize Kohinoor Delux (Bisco bio science). The plot size was 54 $m^2$. All the recommended agronomic practices were followed. Single sprays of each treatment were applied with the help of knapsack sprayer. Observations for Plant height, leaf colour, Number of ears/plant, ear length, Number of kernel row/ear, kernel/row, ear weight, grain weight, plant weight and yield were made before and after 30 days and 60 days of application. Assessments were tabulated as follows:

It can be seen from the above table that treatment 1 with 55% Sulphur+9.5% Zinc oxide+3% Iron Oxide based water disintegrable granules as per the embodiment of the present invention at a dose of around 10 kg per ha, showed a significant increase in the total plant weight, grain yield and silage yield in maize as compared to the treatment 3 with the same composition in a water dispersible granular form at a same dosage of application. In fact, the grain yield increase was observed to be 10.79% higher with Treatment 2 as compared to that of Treatment 4. It was also seen that the ear length was 15.8% higher with treatment 2 as compared to that of Treatment 4.

Further treatment 2 with 55% Sulphur+9.5% Zinc+3% Iron+2.5% silicone dioxide based water disintegrable granules as per the embodiment of the present invention at a dose of around 10 kg per ha in maize as compared to treatments 4 with the same composition in a water dispersible granular form at same dosages of application. Treatment 3 showed a 13% increase in the ear length and a 9.84% increase in the grain yield as compared to that of Treatment 6.

Treatments 3 and 4, while providing instantaneous release and conversion of nutrients for uptake, do not provide nutrients over a longer period of time. The surprising results of treatment 1 and 2, according to an embodiment of the invention, are attributed to the form, including hardness and a fine particle size, in particular, which as a result provides an immediate and sustained release of nutrients over the crop cycle.

The superior results observed were due to an immediate-cum-continous release mechanism of the water disintegrable granular compositions which disintegrate first and then releases the actives and makes the constituents readily available to the plants for a longer duration of the crop life cycle. On the other hand, the prior art water dispersible granular compositions disperse readily but releases the actives only for a short term period as compared to the water disintegrable granular compositions which provided for a sustained long term release leading to surprising yield enhancement.

Comparison of the Physical Properties of Water Disintegrable Granules of Algal Actives:

TABLE 10

| Treatments | Dose g/ha | Ear length (cm) | Total plant weight (kg/sqm) | 100 kernel weight (gm) | Grain yield (q/ha) | Silage yield (q/ha) |
|---|---|---|---|---|---|---|
| 55% Sulphur + 9.5% Zinc oxide + 3% Iron oxide based water disintegrable granules as per the embodiment of the present invention | 10910 | 26.13 | 2.67 | 28.31 | 115.47 | 157.87 |
| 55% Sulphur + 9.5% Zinc oxide + 3% Iron oxide + 2.5% silicone dioxide based water disintegrable granules as per the embodiment of the present invention | 10910 | 27.18 | 2.78 | 27.99 | 111.47 | 166.53 |
| 55% Sulphur + 9.5% Zinc oxide + 3% Iron oxide based water dispersible granules as per teachings of WO2012131702 | 10910 | 22.56 | 1.82 | 24.45 | 104.22 | 149.21 |
| 55% Sulphur + 9.5% Zinc oxide + 3% Iron oxide + 2.5% silicone dioxide based water dispersible granules as per teachings of of WO2012131702 | 10910 | 24.15 | 1.92 | 20.56 | 101.43 | 151.24 |
| Control | — | — | 1.93 | 22.01 | 97.87 | 94.73 |

TABLE 11

| Composition | Bulk Density g/ml | Hardness | Disintegration time (mins) | Attrition Resistance | Granule size mm | Avg Particle size | Dispersibility % | Suspensibility % | Wet Sieve | True density |
|---|---|---|---|---|---|---|---|---|---|---|
| C21 (Spirulina 50% granules as per an embodiment of the invention) | 0.46 | 22.6 N | 20 mins | 89% | 1.5-4.00 | 12.5 | 70 | 25 | 1.9 | 1.41 |
| C22 Chlorella 50% granules as per an embodiment of the invention | 0.86 | 30.1 N | 85 mins | 0.72 | 2.5-5 | 15.16 | 30.2 | 41.5 | 2.5 | 1.86 |
| C23 Pure Spirulina Powder | 0.57 | NA | NA | NA | .1 mm | 50-100 | 75.1 | 66.8 | 5.3 | 1.34 |
| C24 Pure Chlorella Powder | 0.58 | NA | NA | NA | 0.1 | 50-120 | 57.5 | 33.6 | 8.5 | 1.21 |
| C25 Spirulina 50% coated granules as per WO2016113665 | 1.6 | 9 N | 115 mins | 0.62 | 2.5-6 | >100 microns | does not disperse | NA | 80 | 2.7 |

From the above table, it can be seen that the sample C21 with *Spirulina* 50% and C22 with *Chlorella* 50% water disintegrable granules prepared as per the embodiment of present invention, exhibits a surprisingly higher attrition resistance of 89% and 72% and hardness of 22.6 N and 30.1N as compared to Sample C23 which is *Spirulina* powder (commercial product) and C25 which *Chlorella* Powder (commercial product) which has no hardness and attrition resistance at all.

Further it was observed that Sample C25 which is granules of 50% *Spirulina* prepared as per WO2016113665, wherein the *Spirulina* is used as first coating material to form deformable core along with coat of aluminum silicate over a zeolite granule (substrate), and an exterior coating (micronized silica), showed hardness of 9 N, attrition resistance of only 62%, wet sieve retention of 80% (on 75 microns sieve), and does not disperse or suspend at all, whereas *Spirulina* 50% water disintegrable granules prepared as per the embodiment of present invention showing hardness of 22.6N, attrition resistance of 89%, wet sieve retention of 1.9% (on 75 microns sieve) and a good dispersibility and suspensibility. While applying the disintegration tests, the granules of the prior art are to be stirred and hence these slowly break down. However, similar to bentonite granules, (Sample A in FIGS. 5 and 6), these prior art granules (Sample C25) will not disperse or suspend over several hours which in turn leads to poor field performace as compared to water disintegrable granules of the invention.

Field Studies:

Trials were laid in Choriwad (Idar) village, Dist.-Sabarkantha, India, to evaluate various compositions for treatment of Maize Hightech variety (Sona company). The plot size was 3828 m2. All the recommended agronomic practices were followed. Granules of the compositions according to the embodiment, commercially available algal products and prior art, were applied by manual broadcasting. Observations for Plant height (after 30 days, 60 days and 90 days of application), number of kernel/row, ear weight, grain weight, plant weight, kernel weight and yield were made. Assessments were made as follows:

Plant Height was recorded from 10 selected plants from each plot per replication. Number of ears was recorded at harvest time from 15 selected plants from each plot per replication. Ear weight was recorded from 15 selected plants from each plot per replication. Number of Kernels were counted from 15 selected plants from each plot per replication. Grain weight was recorded from 15 selected plants from each plot per replication. Total plant weight was recorded from one sqm area from each plot per replication. 100 kernel weight was recorded from 100 kernel from each plot per replication. Grain yield was recorded from one sqm area from each plot per replication and converted in to q/ha and compared with untreated control.

Shelling % was calculated by below formula $$\text{Shelling \%} = \frac{\text{Grain weight}}{\text{Ear weight}} \times 100$$

TABLE 12

EFFICACY OF VARIOUS TREATMENTS ON MAIZE GROWTH AND DEVELOPMENT

| Treatment no | Composition details | Formulation Dose gm or ml/ha | Plant height (cm) 30 DAA | Plant height (cm) 60 DAA | Plant height (cm) 90 DAA | Ear weight (gm) | No. of kernel/row | Grain weight (gm)/Ear | Shelling % |
|---|---|---|---|---|---|---|---|---|---|
| T1 | C21 (Spirulina 50% Granules as per an embodiment of the invention) | 3000 | 199.80 | 230.03 | 255.07 | 168.13 | 34.88 | 135.60 | 80.65 |
| T2 | C22 (Chlorella 50% granules as per embodiment of present invention) | 3000 | 198.13 | 229.50 | 254.17 | 167.63 | 34.07 | 134.88 | 80.46 |

TABLE 12-continued

EFFICACY OF VARIOUS TREATMENTS ON MAIZE GROWTH AND DEVELOPMENT

| Treatment no | Composition details | Formulation Dose gm or ml/ha | Plant height (cm) 30 DAA | Plant height (cm) 60 DAA | Plant height (cm) 90 DAA | Ear weight (gm) | No. of kernel/row | Grain weight (gm)/Ear | Shelling % |
|---|---|---|---|---|---|---|---|---|---|
| T3 | C23 (Spirulina powder (commercial product)) | 1500 | 195.45 | 227.43 | 252.15 | 164.24 | 33.27 | 131.03 | 79.77 |
| T4 | C24 (*Chlorella* powder-Commercial product) | 1500 | 194.33 | 226.78 | 250.97 | 163.75 | 32.58 | 130.41 | 79.63 |
| T5 | C25 (Spirulina 50% coated granules as per WO2016113665) | 3000 | 192.21 | 227.56 | 248.98 | 162.9 | 32.19 | 130.11 | 79.87 |
| T6 | WSF (19-19-19) | 7500 | 196.53 | 226.80 | 250.60 | 165.86 | 32.93 | 131.35 | 79.19 |
| T7 | Control | — | 190.33 | 219.23 | 246.53 | 159.92 | 31.87 | 128.14 | 80.12 |

It was observed from the above table that treatments 1 and 2 with water disintegrable granules prepared as per the embodiment of the present invention not only showed an increased plant height at 30 days, 60 days and 90 days after application but also demonstrated increased ear weight, number of kernels, grain weight and percentage shelling as compared to the treatments 3, 4 and 5 with *Spirulna* powder (Commercial product), *Chlorella* powder (commercial product) and *Spirulina* 50% granules prepared as per WO2016113665. The poor results observed with the compositions of treatments 5 which contain the same concentration of algae as that of Treatments 1, can be a result of the poor dispersibility, suspensibility and high varying particle size of these compositions as can be seen from Table 11, eventually resulting in the reduced and short term availability of these nutrients to the crops leading to reduction in efficacy.

Also, it was also observed that treatment 1 (at 3000 g/ha) and 2 (at 3000 g/ha) showed improved growth as compared to chemical fertilizer WSF (19-19-19) at 7500 g/ha.

TABLE 13

EFFICACY OF VARIOUS TREATMENTS ON MAIZE YIELD AND YIELD PARAMETERS

| Treatment no | Composition details | Formulation Dose gm or ml/ha | Total plant weight (kg/sqm) | 100 kernel weight (gm) | Grain yield (q/ha) |
|---|---|---|---|---|---|
| T1 | C21 (Spirolina 50% Granules as per an embodiment of the invention) | 2250 | 2.624 | 27.80 | 141.35 |
| T2 | C22 (*Chlorella* 50% granules as per embodiment of present invention) | 3000 | 2.538 | 26.59 | 142.38 |
| T3 | C23 (Spirulina powder (commercial product)) | 1500 | 2.469 | 25.86 | 136.60 |
| T4 | C24(*Chlorella* powder-Commercial product) | 1500 | 2.421 | 23.68 | 134.52 |
| T5 | C25 (Spirulina 50% coated granules as per WO 2016 113665) | 3000 | 2.402 | 24.93 | 133.9 |
| T6 | WSF (19-19-19) | 7500 | 2.417 | 25.87 | 136.45 |
| T7 | Control | — | 2.242 | 23.02 | 128.95 |

It was observed from the above table that treatments 1 and 2 with water disintegrable granules prepared as per the embodiment of the present invention showed percentage yield improvement of 3.4% and 5.8%% as compared to treatments 3 and 4 with *Spirulina* powder (Commercial product), *Chlorella* powder (commercial product) respectively. Treatment 1 also gave a 5.5% higher yield over treatment 5, surprisingly.

Comparison of Physical Properties of Pesticidal Actives:

TABLE 14

| Sample | Composition details | Bulk density (g/mL) | Hardness (Newton) | Disintegration time (min) | Attrition Resistance | Granule Size (mm) | Average Particle size (microns) (D50) | Dispersibility (%) | Suspensibility | Wet sieve retentino on a micron sieve (%) | True Density (g/cm3) |
|---|---|---|---|---|---|---|---|---|---|---|---|
| C26 | 0.4% Chlorantraniliprole water disintegrable granules as per embodiment of present invention | 1.2 | 32.4 | 12 | 95 | 2.5-4.00 | 45 | 42.2 | 36.1 | 19 | 2.2 |
| C27 | 0.4% Chlorantraniliprole GR (prior art sand granules) | 1.04 | N.A. too fine | Does not disintegrate | 99 | 2.0-3.0 | 250-840 microns | 1.38% | 0.8% | 35 | 2.57 |
| C28 | Carboxin 37.5% + Thiram 37.5% water disintegrable granules as per embodiment of present invention | 0.90 | 30.3 | 9 | 88 | 2.5-4.5 | 11 | 48.2 | 39.8 | 5.1 | 1.92 |
| C29 | Carboxin 37.5% + Thiram 37.5% WP (Vitavax) | 1.4 | N.A | N.A | 5.5 | N.A. | 7 | 41.5 | 31.6 | 1.9 | 1.85 |

Bioefficacy of Water Disintegrable Granular Compositions Comprising the Pesticidal Actives:

The trials were conducted in Karnal district of Haryana state in India on paddy, to evaluate the effectiveness of 0.4% Chlorantraniliprole water disintegrable granules as per embodiment of present invention in varying dosages. The experiments were also conducted using 0.4% Chlorantraniliprole GR (prior art sand granules) for comparison as well as an untreated control. The treatments were carried out following the randomized block design and keeping all the agronomic practices uniform for all the treatments.

The treatments were carried out by broadcasting the compositions on 30th day after transplanting of the paddy. Both the applications and their efficacy were evaluated. To avoid intermixing of treatments, about 20 to 30 cm thick false bund boundaries were prepared all around plots having the treatments of granular insecticides.

The treatments applied were as indicated in the table below:

TABLE 15

| Sr. No. | Treatments | Dose L or kg/ha | 15 DAA | 30 DAA | 45 DAA | 60 DAA | Mean |
|---|---|---|---|---|---|---|---|
| 1 | Chlorantriniliprole 0.4% granules according to an embodiment of the invention | 10 | 0 | 4.13 | 5.9 | 13.64 | 7.59 |
| 2 | Chlorantriniliprole 0.4% prior art granules | 10 | 0 | 5.09 | 7.53 | 17.86 | 10.16 |
| 3 | Untreated control | — | 0 | 7.08 | 9.8 | 48.38 | 21.75 |

*DAA—Days after Application
*Mean—The mean is calculated based on the average of the % plants affected by stem borer at 15 DAA, 30 DAA, 45 DAA and 60 DAA It was observed that the application of 0.4% Chlorantraniliprole water disintegrable granules as per the embodiment of present invention at 10 kg per hectare (Treatment 1) was highly effective (% plant affected by stem borer with treatment 1 had mean value of 7.59%) in controlling the stem borer as compared to the prior art 0.4% Chlorantraniliprole GR composition (Treatment 2) (% plant affected by stem borer with treatment 2 had a mean value of 10.16%) at same dosages at 30, 45, and 60 Days after application.

The inventors have for the first time determined that the combination of finely selected properties of low bulk density, high mechanical strength or hardness, fine particle size distribution within a granule size, is leading to compositions which not only provide immediate but a continuous and sustained release and effect over the crops, when applied to the soil. The composition can be tailored to meet the needs of specific crops and is thus useful for releasing agrochemical actives immediately and also over a sustained period of time. The composition not only provides for a slow release of the water insoluble nutrient or algae or pesticide but can also ensure a complete conversion of active to a form for uptake, thereby eliminating any leaching and pollution of underground waters or rivers. The composition ensures uniform application via broadcasting or mechanical applicators, and allows simultaneous application of all different kinds of fertilizers along with the composition of the present invention, and thereby can exhibit surprising efficacy on field application, as compared to conventional formulations. Because of its ease of application, the composition is highly economical to the end user.

From the foregoing it will be observed that numerous modifications and variations can be effectuated without departing from the true spirit and scope of the novel concepts of the present invention. It is to be understood that no limitation with respect to the specific embodiments illustrated is intended or should be inferred.

We claim:

1. A water disintegrable granular composition comprising: at least one agrochemical active, wherein the agrochemical active comprises any one of a water insoluble nutrient or an algae or a pesticidal active, in a concentration range of 0.1% to 95% by weight of the total composition; and, at least one agrochemically acceptable excipient; wherein the water disintegrable granular composition is in a size range of 0.1 mm to 6 mm, comprising particles in a size range of from 0.1 micron to 50 microns; and, wherein the water disintegrable granular composition has a bulk density of less than 1.5 gm/ml and a hardness of at least 1 Newton.

2. The water disintegrable granular composition of claim 1, wherein the water disintegrable granular composition has an attrition resistance of at least 50%.

3. The water disintegrable granular composition of claim 1, wherein the water disintegrable granular composition has a wet sieve retention value on a 75 micron sieve of less than 30%.

4. The water disintegrable granular composition of claim 1, wherein the composition has a wet sieve analysis on a 75 micron sieve of less than 10%.

5. The water disintegrable granular composition of claim 1, wherein the composition has a true density of less than 2.5 g/ml.

6. The water disintegrable granular composition of claim 1, wherein the composition has an attrition resistance of at least 70%.

7. The water disintegrable granular of claim 1, wherein the composition has a disintegration time of less than 200 minutes.

8. The water disintegrable granular composition of claim 1, wherein the composition has a disintegration time of less than 100 minutes.

9. The water disintegrable granular composition of claim 1, wherein the composition has a dispersibility of at least 10%.

10. The water dispersible granular composition of claim 1, wherein the composition has a suspensibility of at least 10%.

11. The composition of claim 1, wherein the composition has a granule size of 1 mm to 6 mm.

12. The water disintegrable granular composition of claim 1, wherein the composition comprises granules which are substantially spherical.

13. The water disintegrable granular composition of claim 1, wherein the water insoluble nutrient comprises elemental Boron, Calcium, Chlorine, Chromium, Cobalt, Copper, Fluorine, Iodine, Iron, Magnesium, Manganese, Molybdenum, Phosphorous, Potassium, Selenium, Silicon, Sodium, Zinc, or salts or derivatives thereof.

14. The water disintegrable granular composition of claim 1, wherein the water insoluble nutrients comprises at least one of elemental sulphur, elemental boron, Boron carbide, Boron nitride, Aluminum oxide, Aluminum dodecaboride, aluminum hydroxide, bauxite, calcitic limestone, Calcium oxalate, Chromium oxide, Cobalt oxide, Cobalt sulphide, Cobalt molybdate, Cobalt carbonate, Copper oxalate, Copper oxide, Copper Sulphide, Copper hydroxide, Cupric sulphide, Copper phosphate, Copper molybdate, Fluorine oxide, Fluorine molybdate, Iron oxide, Iron sulphide, Magnesium oxide, Magnesium hydroxide, Magnesium phosphate tribasic, Magnesium molybdate, Magnesium carbonate, Manganese oxide, Manganese molybdate, Molybdenum acetate, Molybdenum disulphide, Selenium sulphide, Silicon nitride, Zinc sulphide, Zinc oxide, Zinc carbonate, Zinc phosphate, Zinc molybdate, basic slag, elemental chromium, chromium phosphate, iron sucrate, cobalt phosphide, cobalt cyanide, elemental nickel, nickel oxide, nickel oxyhydroxide, nickel carbonate, nickel chromate, nickel hydroxide, millerite, nickel selenide, nickel phosphide, elemental copper, insoluble copper cyanide, chalcocite, copper selenide, copper phosphide, covellite, copper arsenate, elemental silver, elemental zinc, zinc chromate, zinc pyrophosphate, tin hydroxide, tin oxide and tin sulfide, their salts, derivatives and combinations thereof.

15. The water disintegrable granular composition of claim 1, wherein the agrochemically acceptable excipients comprise one or more of surfactants, binders, diluents, disintegrating agents, fillers, sticking agents and pH stabilizers.

16. The water disintegrable granular composition of claim 1, where the composition further comprises one or more of a water insoluble nutrient, algae, microbes, biostimulants, biofertilizers, pesticidal actives, water soluble fertilizers, macronutrients and micronutrients.

17. The water disintegrable granular composition of claim 1 wherein the agrochemically acceptable excipients is selected from at least one of surfactant, dispersant or binder.

18. The water disintegrable granular composition of claim 1, wherein the ratio of algae to agrochemically acceptable excipients is 99:1 to 1:99.

19. The water disintegrable granular composition of claim 1, wherein the algae comprise one or more of green algae, red algae, golden algae, brown algae, golden-brown algae, blue algae or blue-green algae, Asian tuen shaped flat algaes or sea weeds or their derivatives, species and mixtures thereof.

20. The water disintegrable granular composition of claim 19, wherein the algae comprise one or more of Cyanobacteria, Phaeophyceae, Ochrophytes, Glaucophytes, Rhodoplasts, Rhodophytes, Chloroplasts, Ochrophytes, Chrysophyta, Raphidiophyceae, Eumastigophyceae, Xanthophyceae, Synurophytes, Silicoflagellata, Sarcinochrysophyceae, Heterokonts, Crytophytes, Haptophytes, Euglenophytes, Chlorophytes, Charophytes, Land Plants, Embrophyta Or Chlorarachniophytes or their derivatives, species and mixtures thereof.

21. The water disintegrable granular composition of claim 1, wherein the algae comprises *Chlorella* Sp.

22. The water disintegrable granular composition of claim 1, wherein the algae comprises *Spirulina* Sp.

23. The water disintegrable granular composition of claim 1, wherein the pesticidal active comprises at least one of antifoulants, attractants, insecticides, fungicides, herbicides, nematicides, pheromones, defoliants, acaricides, plant growth regulators, algicides, antifeedant, avicides, bactericides, bird repellents, biopesticides, biocides, chemosterilants, safeners, insect attractants, insect repellents, insect growth regulators, mammal repellents, mating disrupters, disinfectants, molluscicides, antimicrobials, miticides, ovicides, fumigants, plant activators, rodenticides, synergists, virucides, repellents, microbial pesticides, plant incorporated protectants or salts, derivatives and mixtures therefor.

24. A process for the preparation of water disintegrable granule composition, the process comprising:
    milling a blend of at least one agrochemical active, wherein the agrochemical active comprises any one of a water insoluble nutrient or an algae or a pesticidal active, at least one agrochemically acceptable excipient and water to obtain a wet mix;
    drying the wet mix to obtain a microgranule;
    agglomerating the microgranule in an agglomerator to obtain a water disintegrable granular composition in a size range of 0.1 mm to 6 mm, comprises particles in a size range of from 0.1 micron to 50 microns; and, wherein the water disintegrable granular composition has a bulk density of less than 1.5 gm/ml and a hardness of at least 1 Newton.

25. A method of fortification of crops and plants, the method comprising applying to one or more of the plant, foliage of the plant, plant propagation material, locus of the plant or the plant propagation material, seeds, seedlings, soil and surroundings of the crop, a water disintegrable granular composition comprising: at least one agrochemical active in a concentration range of at least 0.1% upto 95% by weight, wherein the agrochemical active comprises any one of a water insoluble nutrient or an algae or a pesticidal active; and, at least one agrochemically acceptable excipient; wherein the water disintegrable granular composition is in a size range of 0.1 mm to 6 mm, comprises particles in a size range of from 0.1 micron to 50 microns; and, wherein the water disintegrable granular composition has a bulk density of less than 1.5 gm/ml and hardness of at least 1 Newton.

* * * * *